United States Patent
Czollner et al.

(10) Patent No.: US 6,638,925 B2
(45) Date of Patent: Oct. 28, 2003

(54) BENZAZEPINE DERIVATIVES, MEDICAMENTS CONTAINING THE SAME AND THEIR USE TO PREPARE MEDICAMENTS

(75) Inventors: Laszlo Czollner, Neufeld (AT); Johannes Frohlich, Vienna (AT); Ulrich Jordis, Vienna (AT); Bernhard Kuenburg, Vienna (AT)

(73) Assignee: Sanochemia Ltd., Valetta (MT)

( * ) Notice: Subject to any disclaimer, the term of this patent is extended or adjusted under 35 U.S.C. 154(b) by 0 days.

(21) Appl. No.: 09/242,339

(22) PCT Filed: Apr. 21, 1997

(86) PCT No.: PCT/AT97/00074
§ 371 (c)(1),
(2), (4) Date: Feb. 11, 1999

(87) PCT Pub. No.: WO97/40049
PCT Pub. Date: Oct. 30, 1997

(65) Prior Publication Data
US 2003/0092700 A1 May 15, 2003

(30) Foreign Application Priority Data
Apr. 19, 1996 (AT) ................................. 716/96

(51) Int. Cl.[7] ................. A61K 31/55; C07D 491/10; C07D 491/14
(52) U.S. Cl. ................. 514/212.02; 514/212.04; 514/213.01; 540/519; 540/543; 540/576
(58) Field of Search ................. 540/519, 543, 540/576; 514/212.02, 212.04, 213.01

(56) References Cited

U.S. PATENT DOCUMENTS

| | | | |
|---|---|---|---|
| 3,947,445 A | 3/1976 | Henry et al. | 260/268 |
| 5,336,675 A | * 8/1994 | Snorrason | 514/215 |
| 5,428,159 A | 6/1995 | Shieh et al. | 540/581 |
| 6,043,359 A | * 3/2000 | Czollner et al. | 540/581 |

FOREIGN PATENT DOCUMENTS

| | | |
|---|---|---|
| EP | 0 236 684 | 9/1987 |
| EP | 0 345 808 | 12/1989 |
| EP | 648 771 | * 4/1995 |
| EP | 0 653 427 | 5/1995 |
| NL | 8800350 | 9/1989 |
| WO | WO 88/08708 | 11/1988 |
| WO | WO 95/27715 | 10/1995 |
| WO | WO 96/12692 | 5/1996 |

OTHER PUBLICATIONS

P. Remuzon, "Fluoronaphthyridines as Antibacterial Agents.", J. Med. Chem., 1992, vol. 35, pp. 2898–2909.

* cited by examiner

*Primary Examiner*—Bruck Kifle
(74) *Attorney, Agent, or Firm*—Young & Thompson

(57) ABSTRACT

New derivatives of benzazepine, particularly of benzofuro [3a,3,2,ef][2]benzazepin of the general formula (I)

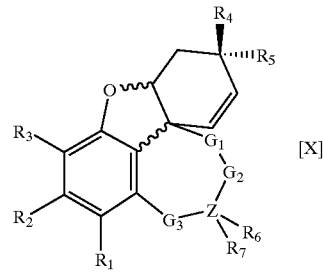

Formula (I)

and new compounds of the general formula (III)

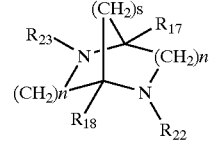

Formula (III)

Drugs, containing compounds of formulas (I) and/or (III), which can be used successfully for the treatment of Alzheimer's disease and related dementia conditions, as well as for the treatment of Langdon-Down syndrome, are also described.

3 Claims, No Drawings

BENZAZEPINE DERIVATIVES, MEDICAMENTS CONTAINING THE SAME AND THEIR USE TO PREPARE MEDICAMENTS

The invention relates to new compounds and drugs containing the new compounds as active, pharmaceutical ingredients.

Likewise, the invention relates to the use of the new compounds for the preparation of drugs for the treatment of Alzheimer's disease and related dementia conditions, as well as for the treatment of Langdon-Down Syndrome (mongolism, trisomy 21).

The acid addition salt of galanthamine, which has the chemical structure

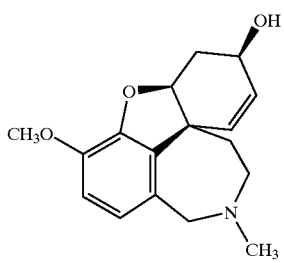

as well as some of its analog, are known as active pharmaceutical ingredients having an inhibitory effect on the synaptic enzyme, acetylcholine esterase. Galanthanine is therefore used pharmacologically for paralysis symptoms resulting from polio mellitus and for different diseases of the nervous system.

Galanthamine and some of its derivatives are also used for the symptomatic treatment of Alzheimer's disease and related dementia conditions (EP 236 684 B1).

Chemically, galanthamine is an alkaloid of the morphine group, which can be obtained from snowdrops (*Galanthus woronowii, G. nivalis* etc.) and other Amaryllidaceae.

Aside from obtaining galanthamine from plant sources, chemical methods of synthesizing galanthamine and its analogs, including its acid addition salts, have also become known (WO 95/27715).

The Down syndrome is attributed to a tripling of chromosome 21, that is, the patients have a set of 47 chromosomes instead of 46. This can be demonstrated relatively simply cytologically. Trisomy 21 is associated with moderate to severe mental impairment and a series of symptoms of physical dysmorphism. A causative treatment is not possible at the present time. The existing impairment can be influenced by selective therapeutic measures. However, a distress usually remains.

The new inventive compounds are new benzazepine derivatives, particularly derivatives of benzofuro[3a, 3, 2, ef] [2] benzazepine.

They are compounds of the general formula (I)

Formula (I)

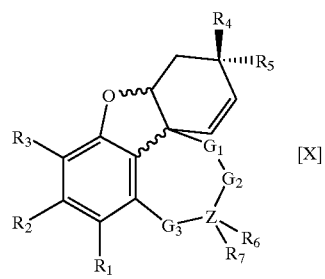

in which $R_1$, $R_2$ either are the same or different and represent hydrogen, F, Cl, Br, I, CN, NC, OH, SH, $NO_2$, $SO_3H$, $NH_2$, $CF_3$ or a lower ($C_1$–$C_6$), optionally branched, optionally substituted (Ar) alkyl or (Ar) alkoxy group or an amino group, which is substituted by one or two or different lower ($C_1$–$C_6$), optionally branched, optionally substituted (Ar) alkyl or (Ar) alkyl carbonyl or (Ar) alkoxy carbonyl or a COOH, COO(Ar) alkyl, CONH, CON(Ar) alkyl group or represents —$(CH_2)_n$—Cl, —$(CH_2)_n$—Br, —$(CH_2)_n$—OH, —$(CH_2)_n$—COOH, —$(CH_2)_n$—CN, —$(CH_2)_n$—NC, in which it is also possible to define $R_1$–$R_2$ jointly as —CH=CH—CH=CH—, —O—, $(CH_2)_n$—O—, with n=1 to 3.

$R_3$=$R_1$, particularly OH and $OCH_3$ and furthermore $R_2$–$R_3$ can jointly form: —O—$(CH_2)_n$—O—, with n=1 to 3

$R_4$, $R_5$: either are both hydrogen or, alternatively, any combination of hydrogen or an (Ar) alkyl, (Ar) alkenyl, (Ar) alkinyl with S—$R_8$, wherein $R_8$ is hydrogen or a lower ($C_1$–$C_{10}$), optionally branched, optionally substituted (Ar) alkyl group

SO—$R_8$, $SO_2R_8$

OH, O-protective group (such as TMS, TBDMS)

O—CS—N—$R_8$ (thiourethanes)

O—CO—N—$R_9$, wherein $R_9$ has the following meaning:

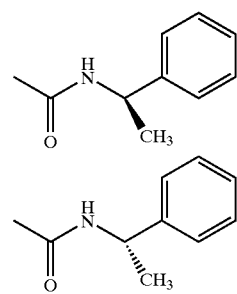

O—CO—$R_5$ (ester, $R_8$ see above), in particular, also esters with the substitution pattern of amino acids such as

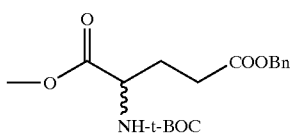

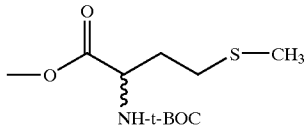

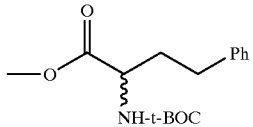

Furthermore: $R_4$, $R_5$=jointly hydrazone (=N—NH—$R_{10}$, =N—N($R_{10}$, $R_{11}$), Oximes (=N—O—$R_{11}$), wherein $R_{10}$ is hydrogen, a lower ($C_1$–$C_6$), optionally branched, optionally substituted (Ar)-alkyl or (Ar)-alkyl carbonyl or (Ar)-alkyl carbonyloxy group as well as a sulfonic acid group, such as a tosyl and mesyl group and $R_{11}$ is hydrogen, a lower ($C_1$–$C_6$), optionally branched, optionally substituted (Ar)-alkyl or (Ar)-alkyl carbonyl group, as well as a sulfonic acid group, such as a tosyl and mesyl group.

as well as substituents of the type

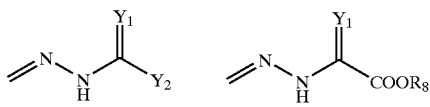

$Y_1$, $Y_2$=O, S, NH or N—$R_{10}$ (excess valences in each case are —H)

wherein, in the event that $R_4$=H, $R_5$ can also be OH and, in the event that $R_5$=H, $R_4$ can also be OH.

$G_1$, $G_2$: jointly or separately have the meaning:

—C($R_{13}$, $R_{14}$)—, wherein $R_{13}$, $R_{14}$ can be hydrogen, OH, a lower, optionally branched, optionally substituted (Ar)-alkyl, aryl, (Ar)-alkoxy or aryloxy group or jointly an alkyl spiro group ($C_3$ to $C_7$ spiro ring).

Furthermore, $G_1$ and $G_2$ jointly represent

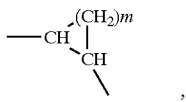

with m=1 to 7

$G_3$: represents $CH_2$ or =CO $R_6$ represents a group —$(G_4)_p$—$(G_5)_q$—$G_6$ with p, q=0 to 1, in which $G_4$ satisfies the following definition —$(CH_2)_r$—, —C($R_{15}$,$R_{16}$)—$(CH_2)_r$—, with R=1 to 6 and $R_{15}$, $R_{16}$=hydrogen, lower, optionally branched or optionally substituted (Ar)-alkyl, cycloalkyl, aryl groups —O— or —$NR_{15}$

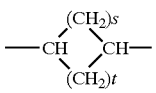

with s=1 to 4, t=0 to 4

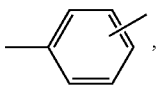

that is an ortho, meta or para disubstituted aromatic

wherein $G_7$=$NR_{15}$, O or S, $G_5$ can be identical with or different from $G_4$ and, in the event that P=1, additionally represents —S—, $G_6$ fulfills the following definition:

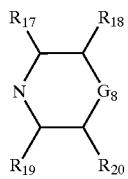

with $R_{17}$, $R_{18}$, $R_{19}$ and $R_{20}$ individually or jointly are the same or different, hydrogen, lower, optionally branched, optionally substituted (Ar)-alkyl, cycloalkyl or aryl groups, wherein $R_{17}$ and $R_{18}$ and $R_{19}$ and $R_{20}$ can jointly form a cycloalkyl group (with a ring size of 3–8)

$G_8$=O, S, NH, $NR_{21}$—$(CH_2)_n$—, $R_{21}$=CHO, $COOR_{17}$ or a heteroaryl group, which is unsubstituted or substituted identically or differently by one or several F, Cl, Br, I, $NO_2$, $NH_2$, OH, alkyl, alkyloxy, CN, NC or $CF_3$, CHO, COOH, COOalkyl, $SO_3H$, SH or S-alkyl groups, (heteroaryl being, in particular, 2-pyridyl, 4-pyridyl, 2-pyrimidinyl) or a methyl group, which is substituted by 1–3 phenyl groups, which are unsubstituted or substituted identically or differently by one or more F, Cl, Br, I, $NO_2$, $NH_2$, alkyl, alkyloxy, CN, NC or $CF_3$ groups, Furthermore, $G_6$ can be:

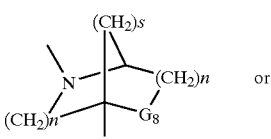

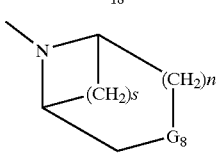 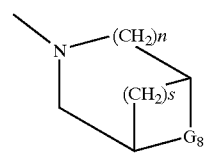

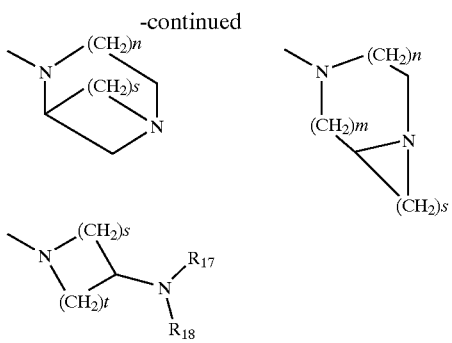

—CHO, COOR$_{17}$, —CONR$_{17}$ a lower, optionally branched, optionally substituted (Ar)-alkyl, (Ar)-alkenyl, (Ar)-alkinyl, cycloalkyl or aryl groups, —O—R$_{17}$, —NR$_{17}$R$_{18}$, phthalamido, —CN or —NC.

R$_7$ is identical with R$_6$ or represents —O—$^{(-)}$ (N-oxide) or a free electron pair (e-pair), wherein R$_6$ and R$_7$ can also form a common ring, 3 to 8 carbon atoms in size and

[X] exists only if, and represents an ion of a pharmacologically usable inorganic or organic acid, when R$_5$ and R$_6$ are present and the nitrogen atoms thus carries a positive charge.

Z=N or N$^+$ in the event that R$_6$ and R$_7$ are present jointly and R$_7$ is not O$^-$.

A special case of the new compounds of the general formula (I) are the compounds of the general formula (II)

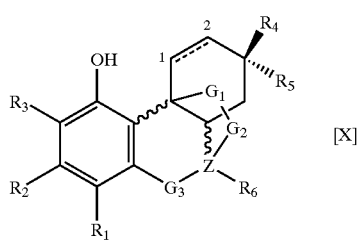

formula (II)

wherein the groups have the meanings described for formula (I). This formula arises formally out of formula (I), in that the bond from C$_1$ to the furan oxygen is broken and, instead, a bond between C$_1$ and Z is formed directly.

Furthermore, the invention comprises the new, substituted, bridged bases of the general formula (III) and their synthesis, and particularly to 2,5-diazabicyclo [2.2.1] heptane:

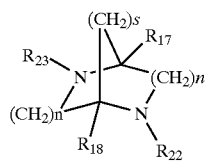

formula (III)

wherein R$_{22}$ is a (hetero) aryl group, which is unsubstituted or substituted identically or differently by one or several F, Cl, Br, I, NO$_2$, NH$_2$, OH, alkyl, alkoxy, CN, NC or CF$_3$, CHO, COOH, COOalkyl, SO$_3$H, SH or S-alkyl groups or a methyl group, which is substituted by two phenyl groups, which are substituted identically or differently by one or more F, Cl, Br, I, NO$_2$, NH$_2$, OH, alkyl, alkoxy, CN, NC or CF$_3$, CHO, COOH, COOalkyl, SO$_3$H, SH or S-alkyl groups, R$_{17}$, R$_{18}$, n, s having the meanings given for the general formula (I) and R$_{23}$=—(G$_5$)$_q$—(G$_4$)$_p$—G$_9$ wherein G$_4$ and G$_5$ have the meanings given for the general formula (I) and G$_9$ is defined as:

Hydrogen, F, Cl, Br, I, OH, O-ts, O-ms, O-triflate, COOH, COCl CHO, —O—R$_{17}$, —NR$_{17}$R$_{18}$, phthalimido, —CN or —NC or by other groups suitable for nucleophilic substitutions, addition reactions, condensation reactions, etc.

Examples of these types of compounds are:

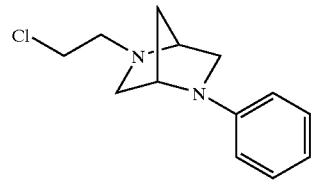

sample a

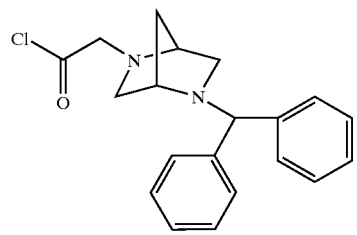

sample b

These compounds of the general formula (III) represent not only a pharmaceutically interesting class of compounds, but also find use as substitutents in a plurality of basic compounds. The compound 105 to 109 represent the compounds.

The inventive drugs can be used successfully for the treatment of Alzheimer's disease and related dementia conditions, as well as for the treatment of Langdon-Downs syndrome.

The invention likewise relates to the use of the compounds used above for the preparation of drugs for the treatment of Alzheimer's disease and related dementias, as well as for the treatment of Langdon-Downs syndrome.

Particularly preferred pursuant to the invention are the compounds named in the survey below. In the survey, the ACHE inhibition values (IC$^{50}$, that is, the 50% inhibition concentration) of the inventive compounds, which are one of the factors, which determine the effectiveness, are also given.

The inhibition of acetylcholine esterase was determined by a modified method of Ellmann (reference 44), human serum from a pool of 10 test subjects being used as serum.

Method: 520 µL of solution of the test substance (concentrations of 10$^{-4}$ to 10$^{-7}$ and, in exceptional cases, up to 10$^{-9}$ moles/liter were used) in 0.02 M tris (hydroxymethyl)aminomethane solution, buffered with HCl to a pH of 7.8 and 400 µL of m-nitrophenol solution (Sigma Diagnostics, Art. 420—4) were incubated in the semi-micro cuvette at 37° C. with 40 µL of cholinesterase solution (Sigma Diagnostics, Art. 420-MC, diluted 1:15 with water) and 160 µL of serum and the change in the absorption was measured over 5 minutes against a comparison sample in a Beckmann DU-50 spectrophotometer with a kinetics program. The values were given as a percentage of the comparison sample and the inhibiting concentration (IC$^{50}$) was calculated from the course of the curve.

Survey of the New Compounds of the Type of the General Formula:

| Subst. Nr. | Chir. | R₁ | R₂ | R₃ | R₄ | R₅ | R₆ | R₇ | Z | [X] | G₃ | IC₅₀ in μMol |
|---|---|---|---|---|---|---|---|---|---|---|---|---|
| Gal *HBr | (−) | H | H | CH₃ | OH | H | CH₃ | H | N⁺ | Br⁻ | CH₂ | 6 |
| 1 | (+/−) | Br | H | CH₃ | OH | H | CH₃ | — | N | — | CH₂ | 10 |
| 2 | (+/−) | Br | H | CH₃ | H | OH | CH₃ | — | N | — | CH₂ | 4 |
| 3 | (−) | Br | H | CH₃ | OH | H | CH₃ | — | N | — | CH₂ | 5 |
| 4 | (+/−) | Br | H | CH₃ | OH | H | H | — | N | — | CH₂ | 3 |
| 5 | (−) | Br | H | CH₃ | OH | H | H | — | N | — | CH₂ | >150 |
| 6 | (+) | Br | H | CH₃ | OH | H | H | — | N | — | CH₂ | |
| 7 | (+/−) | br | H | CH₃ | H | OH | CHO | — | N | — | CH₂ | |
| 8 | (+/−) | Br | H | CH₃ | —O—CH₂—CH(CH₃)—O— | | CHO | — | N | — | CH₂ | |
| 9 | (+/−) | Br | H | CH₃ | —O—CH₂—CH(CH₃)—O— | | CH₃ | — | N | — | CH₂ | |
| 10 | (+/−) | H | H | CH₃ | —O—CH₂—CH₂—O— | | CH₃ | — | N | — | CH₂ | |
| 11 | (+/−) | Br | H | CH₃ | —O—CH₂—CH₂—O— | | H | — | N | — | CH₂ | |
| 12 | (+/−) | Br | H | CH₃ | —O—CH₂—CH₂—O— | | CH₂—Ph | — | N | — | CH₂ | |
| 13 | (+/−) | Br | H | CH₃ | =O | | H | — | N | — | CH₂ | |
| 14 | (+/−) | Br | H | CH₃ | =O | | CH₃ | — | N | — | CH₂ | |
| 15 | (+/−) | Br | H | CH₃ | O—CH₂—CH₂—OH | H | [PhCH(CH₃)NHC(O)O—] | — | N | — | CH₂ | 50 |
| 16 | (+/−) | Br | H | CH₃ | | | | — | N | — | CH₃ | |
| 17 | (−) | H | H | CH₃ | OH | H | CH₃ | — | N | — | CH₂ | 70 |

-continued
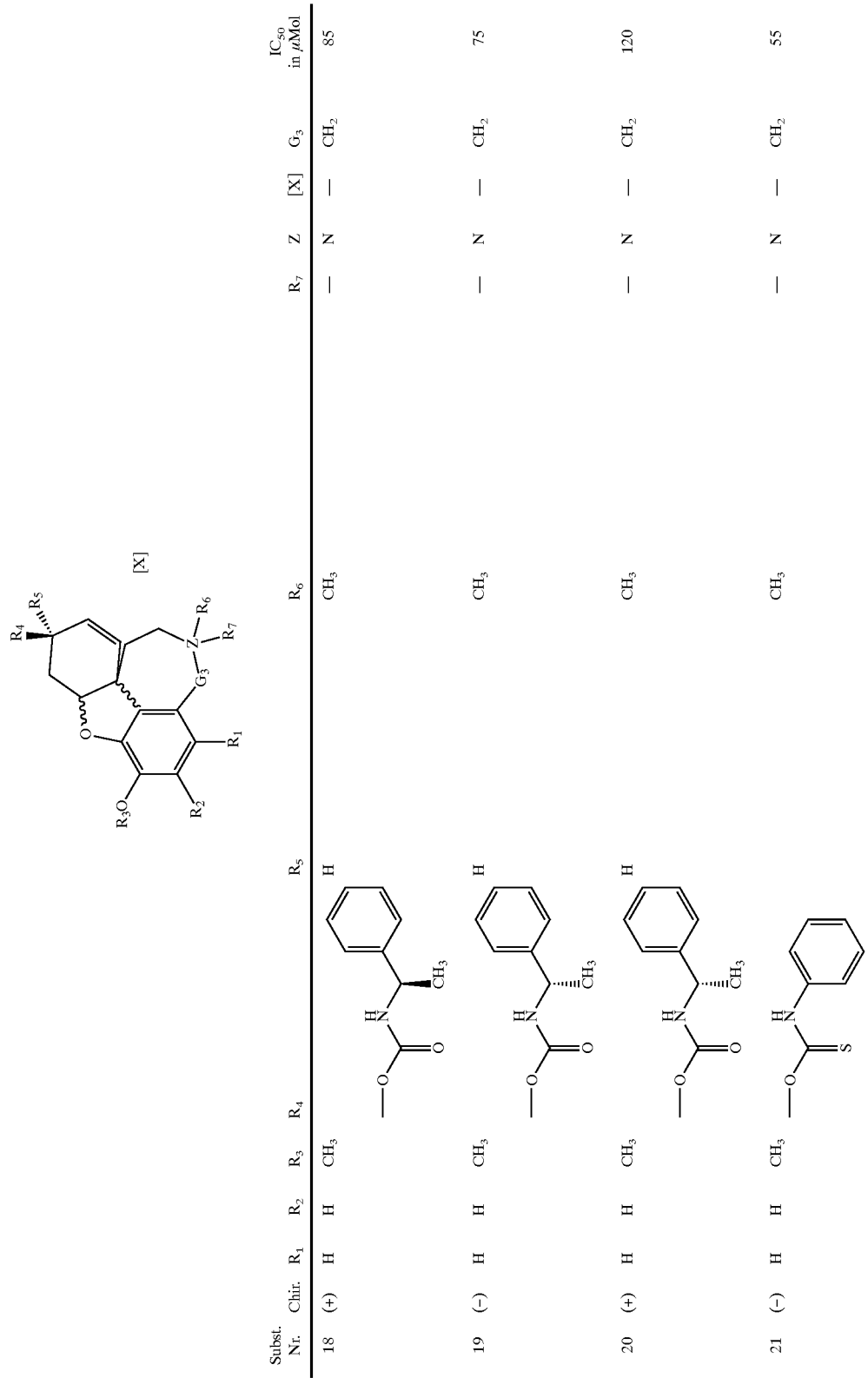
| Subst. Nr. | Chir. | R1 | R2 | R3 | R4 | R5 | R6 | R7 | Z | [X] | G3 | IC50 in μMol |
|---|---|---|---|---|---|---|---|---|---|---|---|---|
| 18 | (+) | H | H | CH3 | —O—C(=O)—NH—*CH(CH3)(C6H5) | H | CH3 | — | N | — | CH2 | 85 |
| 19 | (−) | H | H | CH3 | —O—C(=O)—NH—*CH(CH3)(C6H5) | H | CH3 | — | N | — | CH2 | 75 |
| 20 | (+) | H | H | CH3 | —O—C(=O)—NH—*CH(CH3)(C6H5) | H | CH3 | — | N | — | CH2 | 120 |
| 21 | (−) | H | H | CH3 | —O—C(=S)—NH—C6H5 | H | CH3 | — | N | — | CH2 | 55 |

-continued
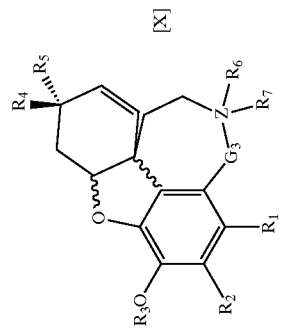
| Subst. Nr. | Chir. | R$_1$ | R$_2$ | R$_3$ | R$_4$ | R$_5$ | R$_6$ | R$_7$ | Z | [X] | G$_3$ | IC$_{50}$ in μMol |
|---|---|---|---|---|---|---|---|---|---|---|---|---|
| 22 | (+) | H | H | CH$_3$ | CH$_3$ | —O—C(=S)—NH—Ph | CH$_3$ | — | N | — | CH$_2$ | 35 |
| 23 | (−) | H | H | CH$_3$ | CH$_3$ | —O—C(=S)—NH—C$_4$H$_9$ | CH$_3$ | — | N | — | CH$_2$ | 25 |
| 24 | (+) | H | H | CH$_3$ | CH$_3$ | —O—C(=S)—NH—C$_4$H$_9$ | CH$_3$ | — | N | — | CH$_2$ | 85 |
| 25 | (−) | H | H | CH$_3$ | H | —O—C(=O)—CH$_2$—NH-t-BOC | CH$_3$ | — | N | — | CH$_2$ | 45 |
| 26 | (−) | H | H | CH$_3$ | H | —O—C(=O)—CH(NH-t-BOC)—CH$_2$—COOBr | CH$_3$ | — | N | — | CH$_2$ | |

-continued
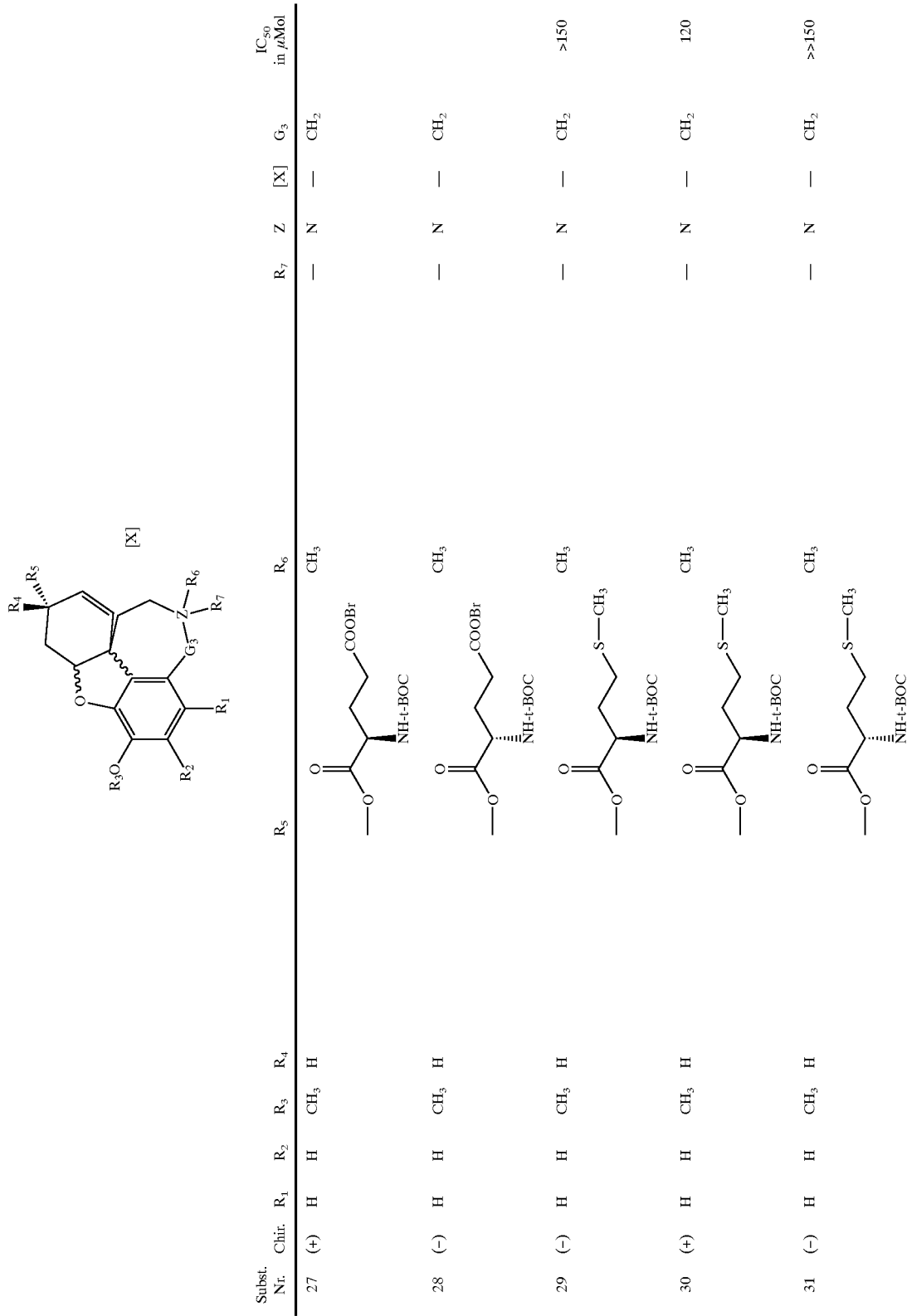
| Subst. Nr. | Chir. | R1 | R2 | R3 | R4 | R5 | R6 | R7 | Z | [X] | G3 | IC50 in μMol |
|---|---|---|---|---|---|---|---|---|---|---|---|---|
| 27 | (+) | H | H | CH3 | H | ![COOBr, NH-t-BOC methyl ester] | CH3 | — | N | — | CH2 | |
| 28 | (−) | H | H | CH3 | H | ![COOBr, NH-t-BOC methyl ester] | CH3 | — | N | — | CH2 | |
| 29 | (−) | H | H | CH3 | H | ![S-CH3, NH-t-BOC methyl ester] | CH3 | — | N | — | CH2 | >150 |
| 30 | (+) | H | H | CH3 | H | ![S-CH3, NH-t-BOC methyl ester] | CH3 | — | N | — | CH2 | 120 |
| 31 | (−) | H | H | CH3 | H | ![S-CH3, NH-t-BOC methyl ester] | CH3 | — | N | — | CH2 | >>150 |

-continued

| Subst. Nr. | Chir. | R1 | R2 | R3 | R4 | R5 | R6 | R7 | Z | [X] | G3 | IC50 in μMol |
|---|---|---|---|---|---|---|---|---|---|---|---|---|
| 32 | (−) | H | H | CH3 | H | methyl ester of N-Boc-phenylalanine (—O—C(=O)—CH(CH2Ph)—NH-t-BOC) | CH3 | — | N | — | CH2 | 100 |
| 33 | (+/−) | Br | H | CH3 | —O—C(=O)—NH—Ph | H | CH3 | — | N | — | CH2 | |
| 34 | (+/−) | Br | H | CH3 | —O—C(=O)—NH—CH(CH3)Ph | H | CH3 | — | N | — | CH2 | |
| 35 | (+/−) | Br | H | CH3 | OH | H | n-Pentyl | — | N | — | CH2 | |
| 36 | (+/−) | Br | H | CH3 | O-TBDMS | H | H | — | N | — | CH2 | |
| 37 | (+/−) | Br | H | CH3 | O-TMS | H | CH3 | — | N | — | CH2 | |
| 38 | (+/−) | Br | H | CH3 | O-TBDMS | H | CH3 | — | N | — | CH2 | |
| 39 | (+/−) | H | H | CH3 | O-TBDMS | H | CH3 | — | N | — | CH2 | |
| 40 | (+/−) | Br | H | CH3 | OH | Ethylenglykolketyl | CH2—Ph | — | N | — | CH2 | |
| 41 | (+/−) | Br | H | CH3 | OH | =O | Allyl | — | N | — | CH2 | |
| 42 | (+/−) | H | H | CH3 | OH | =O | Allyl | — | N | — | CH2 | |
| 43 | (+/−) | Br | H | CH3 | OH | H | CH2—Ph | — | N | — | CH2 | |
| 44 | (+/−) | Br | H | CH3 | OH | =O | CH2—Ph | — | N | — | CH2 | |
| 45 | (+/−) | H | H | CH3 | OH | H | CH2—Ph | — | N | — | CH2 | |
| 46 | (+/−) | H | H | CH3 | OH | =O | CH2—Ph | — | N | — | CH2 | |
| 47 | (+/−) | H | H | CH3 | OH | =O | CH2—Ph | — | N | — | CH2 | |

-continued

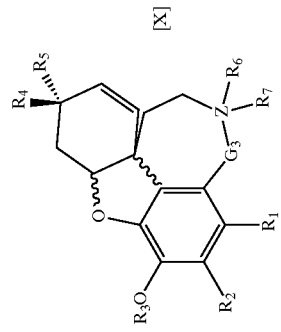

| Subst. Nr. | Chir. | $R_1$ | $R_2$ | $R_3$ | $R_4$ | $R_5$ | $R_6$ | $R_7$ | Z | [X] | $G_3$ | $IC_{50}$ in μMol |
|---|---|---|---|---|---|---|---|---|---|---|---|---|
| 48 | (+/−) | Br | H | $CH_3$ | O—$COCH_3$ | H | $COCH_3$ | — | N | — | $CH_2$ | insol. |
| 49 | (+/−) | Br | H | $CH_3$ | OH | H | n-Hexyl | — | N | — | $CH_2$ | insol. |
| 50 | (+/−) | Br | H | $CH_3$ | OH | H | Propargyl | — | N | — | $CH_2$ | 20 |
| 51 | (+/−) | Br | H | $CH_3$ | OH | H | $CH_2COOEt$ | — | N | — | $CH_2$ | insol. |
| 52 | (+/−) | Br | H | $CH_3$ | OH | H | $CH_2CN$ | — | N | — | $CH_2$ | |
| 53 | (+/−) | Br | H | $CH_3$ | OH | H | $CH_2CONH_2$ | — | N | — | $CH_2$ | |
| 54 | (+/−) | Br | H | $CH_3$ | OH | H | 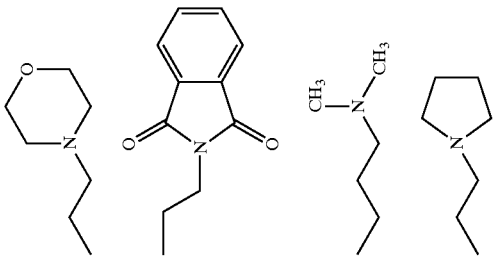 | — | N | — | $CH_2$ | 3 |
| 55 | (+/−) | Br | H | $CH_2$ | OH | H | | — | N | — | $CH_2$ | |
| 56 | (+/−) | Br | H | $CH_2$ | OH | H | | — | N | — | $CH_2$ | |
| 57 | (+/−) | Br | H | $CH_3$ | OH | H | | — | N | — | $CH_2$ | |

-continued

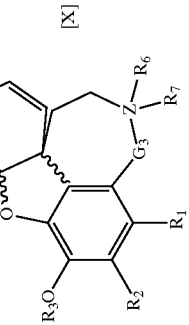

| Subst. Nr. | Chir. | R$_1$ | R$_2$ | R$_3$ | R$_4$ | R$_5$ | R$_6$ | R$_7$ | Z | [X] | G$_3$ | IC$_{50}$ in μMol |
|---|---|---|---|---|---|---|---|---|---|---|---|---|
| 58 | (+/−) | Br | H | CH$_3$ | OH | H | CO—CH$_3$ | — | N | — | CH$_2$ | 0.2 |
| 59 | (+/−) | Br | H | CH$_3$ | OH | H | CO—COOEt | — | N | — | CH$_2$ | |
| 60 | (+/−) | Br | H | CH$_3$ | OH | H | CO—(CH$_2$)$_2$—COOCH$_3$ | — | N | — | CH$_2$ | insol. |
| 61 | (+/−) | Br | H | CH$_3$ | OH | H | COOCH$_3$ | — | N | — | CH$_2$ | insol. |
| 62 | (+/−) | Br | H | CH$_3$ | OH | H | t-BOC | — | N | — | CH$_2$ | |
| 63 | (+/−) | Br | H | CH$_3$ | OH | H | CO—C$_{15}$H$_{31}$ | — | N | — | CH$_2$ | >150 |
| 64 | (+/−) | Br | H | CH$_3$ | OH | H | Ethyl | — | N | — | CH$_2$ | |
| 65 | (+/−) | Br | H | CH$_3$ | OH | H | CO—(CH$_2$)$_2$—COOH | — | N | — | CH$_2$ | |
| 66 | (+/−) | Br | H | CH$_3$ | OH | H | CO—COOH | — | N | — | CH$_2$ | |
| 67 | (+/−) | Br | H | CH$_3$ | OH | H | CH$_2$—CH$_2$—OH | — | N | — | CH$_2$ | |
| 68 | (+/−) | Br | H | CH$_3$ | OH | H | CH$_2$—CH$_2$—OH | — | N | — | CH$_2$ | |
| 69 | (+/−) | H | H | CH$_3$ | OH | H | CH$_2$—CH$_2$—NH$_2$ | — | N | — | CH$_2$ | |
| 70 | (+/−) | Br | H | CH$_3$ | OH | H | CH$_2$—COOH | — | N | — | CH$_2$ | |
| 71 | (+/−) | Br | H | CH$_3$ | OH | H | CO—C$_{15}$H$_{31}$ | — | N | — | CH$_2$ | |
| 72 | (−) | Br | H | CH$_3$ | OH | H | CH$_2$CN | — | N | — | CH$_2$ | |
| 73 | (+/−) | Br | H | CH$_3$ | OH | H | | — | N | — | CH$_2$ | |
| 74 | (+/−) | H | H | CH$_3$ | OH | H | | — | N | — | CH$_2$ | |
| 75 | (+/−) | H | H | CH$_3$ | | =N—OTs | CH$_3$ | — | N | — | CH$_2$ | insol. |
| 76 | (+) | H | H | CH$_3$ | | =N—OH | CH$_3$ | — | N | — | CH$_2$ | insol. |
| 77 | (−) | H | H | CH$_3$ | | =N—OH | CH$_3$ | — | N | — | CH$_2$ | insol. |
| 78 | (+) | H | H | CH$_3$ | | =N—OCH$_3$ | CH$_3$ | — | N | — | CH$_2$ | >150 |
| 79 | (−) | H | H | CH$_3$ | | =N—OCH$_3$ | CH$_3$ | — | N | — | CH$_2$ | |
| 80 | (+/−) | H | H | CH$_3$ | | =NH | CH$_3$ | — | N | — | CH$_2$ | |
| 81 | (−) | H | H | CH$_3$ | | =N—NH—CH$_3$ | CH$_3$ | — | N | — | CH$_2$ | >150 |
| 82 | (+/−) | H | H | CH$_3$ | | =N—N(CH$_3$)$_2$ | CH$_3$ | — | N | — | CH$_2$ | insol. |

-continued

| Subst. Nr. | Chir. | $R_1$ | $R_2$ | $R_3$ | $R_4$ | $R_5$ | $R_6$ | $R_7$ | Z | [X] | $G_3$ | $IC_{50}$ in μMol |
|---|---|---|---|---|---|---|---|---|---|---|---|---|
| 83 | (+/−) | H | H | $CH_3$ | $CH_3$ | =N—HN—$(CH_2)_2$—OH | $CH_3$ | — | N | — | $CH_2$ | >150 |
| 84 | (+/−) | H | H | $CH_3$ | $CH_3$ | =N—NH—CHO | $CH_3$ | — | N | — | $CH_2$ | >150 |
| 85 | (+/−) | H | H | $CH_3$ | $CH_3$ | =N—NH-tBOC | $CH_3$ | — | N | — | $CH_2$ | >150 |
| 86 | (+/−) | H | H | $CH_3$ | $CH_3$ | =N—NH-pTs | $CH_3$ | — | N | — | $CH_2$ | insol. |
| 87 | (+/−) | H | H | $CH_3$ | $CH_3$ | =N—NH—C(=O)—NH$_2$ | $CH_3$ | — | N | — | $CH_2$ | >150 |
| 88 | (+/−) | H | H | $CH_3$ | $CH_3$ | =N—NH—C(=NH)—NH$_2$ | $CH_3$ | — | N | — | $CH_2$ | >150 |
| 89 | (+/−) | H | H | $CH_3$ | $CH_3$ | =N—NH—C(=O)—COOH | $CH_3$ | — | N | — | $CH_2$ | >150 |
| 90 | (+/−) | H | H | $CH_3$ | $CH_3$ | =N—NH$_2$ | $CH_3$ | — | N | — | $CH_2$ | 40 |
| 91 | (−) | H | H | $CH_3$ | OH | H | N(CH$_3$)(CH$_3$)(propyl) | $CH_3$ | $N^+$ | Br$^-$ | $CH_2$ | 8 |
| 92 | (−) | H | H | $CH_3$ | OH | H | pyrrolidinyl-propyl | $CH_3$ | $N^+$ | Cl$^-$ | $CH_2$ | 2 |

-continued

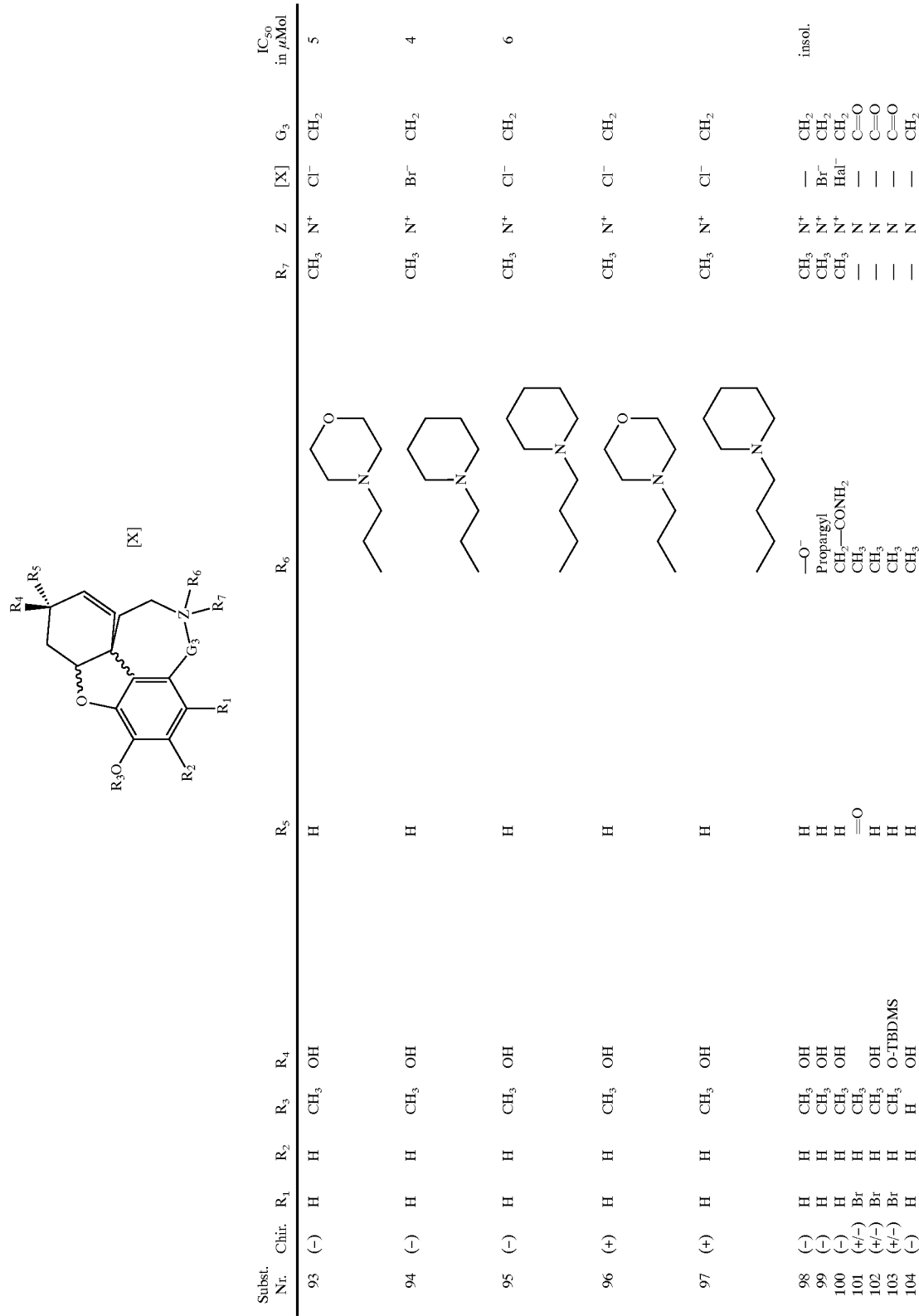

| Subst. Nr. | Chir. | $R_1$ | $R_2$ | $R_3$ | $R_4$ | $R_5$ | $R_6$ | $R_7$ | Z | [X] | $G_3$ | $IC_{50}$ in μMol |
|---|---|---|---|---|---|---|---|---|---|---|---|---|
| 93 | (−) | H | H | $CH_3$ | OH | H | morpholine-propyl | $CH_3$ | $N^+$ | $Cl^-$ | $CH_2$ | 5 |
| 94 | (−) | H | H | $CH_3$ | OH | H | piperidine-propyl | $CH_3$ | $N^+$ | $Br^-$ | $CH_2$ | 4 |
| 95 | (−) | H | H | $CH_3$ | OH | H | piperidine-butyl | $CH_3$ | $N^+$ | $Cl^-$ | $CH_2$ | 6 |
| 96 | (+) | H | H | $CH_3$ | OH | H | morpholine-butyl | $CH_3$ | $N^+$ | $Cl^-$ | $CH_2$ | |
| 97 | (+) | H | H | $CH_3$ | OH | H | piperidine-butyl | $CH_3$ | $N^+$ | $Cl^-$ | $CH_2$ | |
| 98 | (−) | H | H | $CH_3$ | OH | H | —$O^-$ | $CH_3$ | $N^+$ | — | $CH_2$ | insol. |
| 99 | (−) | H | H | $CH_3$ | OH | H | Propargyl | $CH_3$ | $N^+$ | $Br^-$ | $CH_2$ | |
| 100 | (+/−) | H | H | $CH_3$ | OH | =O | $CH_2$—$CONH_2$ | $CH_3$ | $N^+$ | $Hal^-$ | C=O | |
| 101 | (+/−) | Br | H | $CH_3$ | OH | H | $CH_3$ | — | N | — | — | |
| 102 | (+/−) | Br | H | $CH_3$ | O-TBDMS | H | $CH_3$ | — | N | — | C=O | |
| 103 | (+/−) | H | H | $CH_3$ | O-TBDMS | H | $CH_3$ | — | N | — | C=O | |
| 104 | (−) | H | H | H | OH | H | $CH_3$ | — | N | — | $CH_2$ | |

-continued

| Subst. Nr. | Chir. | R₁ | R₂ | R₃ | R₄ | R₅ | R₆ | R₇ | Z | [X] | G₃ | IC₅₀ in μMol |
|---|---|---|---|---|---|---|---|---|---|---|---|---|
| 105 | (+/−) | Br | H | CH₃ | OH | H | N-butyl-diazabicyclic-N-phenyl | — | N | — | CH₂ | |
| 106 | (+/−) | H | H | CH₃ | OH | H | N-butyl-diazabicyclic-N-phenyl | — | N | — | CH₂ | |
| 107 | (+/−) | Br | H | CH₃ | OH | H | N-propyl-diazabicyclic-N-(4-fluorophenyl) | — | N | — | CH₂ | |

-continued

| Subst. Nr. | Chir. | $R_1$ | $R_2$ | $R_3$ | $R_4$ | $R_5$ | $R_6$ | $R_7$ | Z | [X] | $G_3$ | $IC_{50}$ in µMol |
|---|---|---|---|---|---|---|---|---|---|---|---|---|
| 108 | (+/−) | Br | H | $CH_3$ | OH | H | CH₂C(O)–N-bicyclic-N-CH₂-phenyl | — | N | — | $CH_2$ | |
| 109 | (+/−) | Br | H | $CH_3$ | OH | H | propyl-N-bicyclic-N-CH₂-phenyl | — | N | — | $CH_2$ | |
| 110 | (+/−) | Br | H | $CH_3$ | OH | —O—$CH_2CH_2$—O— | $CH_3$ | — | N | — | $CH_2$ | |
| 111 | (+/−) | Br | H | $CH_3$ | OH | H | $CH_3$ | — | N | — | $CH_2$ | |
| 112 | (+/−) | H | H | $CH_3$ | OH | H | H | — | N | — | $CH_2$ | |
| 117 | (−) | $NO_2$ | H | $CH_3$ | OH | H | $CH_3$ | — | N | — | $CH_2$ | >150 |
| 118 | (−) | $NH_2$ | H | $CH_3$ | OH | H | $CH_3$ | — | N | — | $CH_2$ | 7 |

The general formula (II) is a special case of the general formula (I)

formula (II)

| Pat II Nr. | Chiral | R$_1$ | R$_2$ | R$_3$ | R$_4$ | R$_5$ | G$_3$ | DB* | IC$_{50}$ |
|---|---|---|---|---|---|---|---|---|---|
| 113 | (+/−) | Br | H | CH$_3$ | =O | | CH$_2$ | yes | 5 |
| 114 | (+/−) | Br | H | CH$_3$ | OH | H | CH$_2$ | yes | |
| 115 | (+/−) | H | H | CH$_3$ | OH | H | CH$_2$ | yes | >150 |
| 116 | (+/−) | Br | H | CH$_3$ | OH | H | CH$_2$ | no | 50 |

*DB = double bond
Please note: "Chiral" refers in the whole of the Table to the plurality of the respective educt. The values of the rotation of the products are determined in the experimental part.

The compounds, contained in drugs pursuant to the invention, can be administered in any suitable chemical or physical form, such as an acid addition salt. For example, they can be administered as hydrobromide, hydrochloride, methyl sulfate or methyl iodide.

The inventive drugs can be administered to patients orally or by subcutaneous or intravenous injection or intracerebroventricularly by means of an implanted container.

It may be necessary to start with doses lower than effective ones.

Typical dosing rates when administering drugs containing the active ingredients proposed pursuant to the invention depend on the nature of the compound used and on the condition of the patient. Typically, dosage rates lie in the range of 0.01 to 1.0 mg per day per kg of body weight, depending on the age, the mental condition and other medication of the patient.

The inventive drugs may be present in the following specific formations:

tablets or capsules containing 0.5 to 50 mg parenteral solution containing 0.1 to 30 mg/mL liquid formulation for oral administration in a concentration of 0.1 to 15 mg/mL The inventive compounds can also be a transdermal system, in which 0.1 to 10 mg are released per day.

A transdermal dosing system consists of a reservoir layer, which contains 0.1–30 mg of the active substance as free base or salts, if necessary, together with a penetration accelerator, such as dimethyl sulfoxide, or a carboxylic acid, such as octanoic acid, and a skin-neutral polyacrylate, such as hexyl acrylate/vinyl acetate/acrylic acid copolymer together with a plasticizer, such as isopropyl myristate. The covering is an outer layer, which is impermeable to the active ingredient, such as metal-coated, siliconized polyethylene Band-Aid with a thickness of, for example, 0.35 mm. A dimethylaminomethyl acrylate/methyl acrylate copolymer in an organic solvent, for example, is used to produce an adhesive layer.

Some examples of methods, by means of which inventive compounds can be synthesized, are given below.

EXPERIMENTAL SECTION

General Instructions

Thin-layer chromatography with silica gel 60 F$_{254}$ (Merck, Art. No. 5554).

Abbreviations used:

NH$_4$OH concentrated aqueous ammonia

PE petroleum ether or naptha (40°–60° C.)

p-Ts=p-Tos=p-toluene sulfamide

CE=capillary electrophoresis

Rotations are generally recorded at a concentration of C=0.1.

The melting points are determined by the Kofler method using a microscope with a hot stage; the values are not corrected.

The glass autoclave comes from Büchi (TinyClave, MiniClave).

The water content of the solvent where given is determined by the Karl Fischer method.

The element microanalysis were carried out in the Microanalytical Laboratory at the Institute for Physical Chemistry of the University of Vienna under the direction of Mag. J. Theiner.

NMR spectra were recorded on a Büchi 200 FS FT-NMR spectrometer, CDCl$_3$ or DMSO-d$_6$ being used as solvent.

$^1$H-NMR: measurement frequency 200.13 MHz, internal standard: CDCl$_3$ ($\delta$=7.26 ppm)

or

DMSO-d$_6$ ($\delta$=2.50 ppm)

$^{13}$C-NMR: measurement frequency 50.32 MHz, internal standard: CDCl$_3$ ($\delta$=77.0 ppm)

or

DMSO-d$_6$ ($\delta$=39.5 ppm)

The splittings in the NMR spectroscopy are labeled as follows:

| s = singlet | d = doublet | t = triplet |
|---|---|---|
| q = quartet | m = multiplet | |

Where necessary, the multiplicities of the $^{13}$C spectra were determined by DEPT experiments, the assignments of the $^1$H spectra optionally by COSY experiments. Uncertain assignments were marked with an asterisk.

Experimental Section (+/−) 8-Bromogalanthamine (1), (+/−) 8-Bromo-epigalanthamine (2)

To a suspension of 4.0 g (10.5 mmoles) of bromo-N-formyl narwedine in 60 mL of toluene, 24 mL (36 mmoles) of 1M DIBAL-H solution in toluene is added dropwise at 0° C. The reaction is stirred for one hour at room temperature, the remaining reducing agent is decomposed with water and 20 mL of ammonia are subsequently added. After stirring for 20 minutes at room temperature, the precipitated material is filtered off, the organic phase is separated and the aqueous phase washed with 50 mL of toluene. The combined organic phases are dried over sodium sulfate, filtered and the solvent is removed under vacuum. The residue is separated by means of column chromatography. Yield: 0.9 g (23.3%) of one and 0.8 g (20.7%) of two.

Bromogalanthamine (1) data:

molecular weight $C_{17}H_{19}BrNO_3$: 365.23

IR(KBr): 689.03m; 778.57m; 839.37m; 989.86m; 1050.66s; 1212.43s; 1279.87s; 1434.08s; 14.72s; 1613.99s; 2667.39m; 3370–3778br.

$^1$H-NMR (CDCl$_3$): 6.9 (s, 1 H); 6.06 (m, 2 H); 4.60 (d, 1 H); 4.15, (t, 1 H); 3.92 (d, 1 H); 3.82 (s, 3 H); 3.24 (m, 1 H); 2.98 (dt, 1 H); 2.68 (dd, 1 H); 2.42 (s, 3 H); 2.05 (m, 2 H); 1.60 (dt, 1 H).

$^{13}$C-NMR (CDCl$_3$): 145.32 s; 144.00 s 133.96 s; 127.95 d; 127.68 s; 126.51 d; 115.61 d; 114.22 s; 88.56 d; 61.58 d; 58.56 t; 55.95 q; 53,.6 t; 48.56 s; 42.06 q; 33.47 t; 29.69 t.

Epi-bromogalanthamine (2) data:

molecular weight $C_{17}H_{19}BrNO_3$: 365.23

IR(KBr): 667.95 w; 752m; 836.68m; 1040.31s; 1208.39s; 12.82m; 1435.25m; 1485.72m; 1512.94w; 1558.27w; 1615.19m; 1667.14w; 2943.24w; 3360–3575br.

$^1$H-NMR (CDCl$_3$): 6.85 (s, 1 H); 5.96 (AB, 22); 4.69 (m, 2 H); 4.28 (d, 1 H); 3.90 (d, 1 H); 3.83 (s, 1H); 3.25 (m, 1 H); 2.95 (m, 1 H); 2.85 (dt, 1 H); 2.36 (s 3 H); 2.15 (td, 1 H), 1.69 (m, 2 H).

$^{13}$C-NMR (CDCl$_3$+DMSO-d$_6$): 145.84 s; 143.49 s; 133.89 s; 133.14 d; 126.12 s; 124.35 d; 115.04 s; 113.01 s; 88.26 d; 61.10 d; 57.44 t; 55.58 q; 52.84 t; 47.86 s; 41.20 q; 33.35 t; 31.43 t.

(+/−) Bromogalanthamine (1)

Method 1

To a solution of 2.0 g (5.6 mmoles) of (4) in 20 mL of water, 5 mL of 89% HCOOH and 5 mL of 37% formaldehyde are added and boiled under reflux. After being boiled for 15 minutes, the reaction mixture is diluted with water, the pH is adjusted with 25% ammonia to a value of 9 and the solution is extracted three times with 20 mL of methylene chloride. The combined organic phases are dried with sodium sulfate, filtered and the solvent is evaporated under vacuum. Chromatographic purification of the residue (150 mg of silica gel) CHCl$_3$: MeOH=97:→95:5) results in a colorless foam. Yield: 2.0 g (96.4%)

Method 2

To a suspension of 10 g (26.4 mmoles) of bromo-N-formyl narwedine in 200 mL of THF, 100 mL (100 mmoles) of a 1M solution of L-selectride is added dropwise at 0° C. during a period of 30 minutes. After stirring for 30 minutes at 0° C., the reagent is decomposed with water and the reaction mixture treated with 100 mL of a 25% ammonia solution. After 30 minutes of stirring at room temperature, the solvent is concentrated under vacuum to half its volume, transferred to a separating funnel, treated with 100 mL of 25% ammonia and extracted three times with 200 mL of methylene chloride. The combined organic phases are dried over sodium sulfate, filtered and the solvent is evaporated under vacuum. To the residue, 50 mL of water, 30 mL of 98% HCOOH and 30 mL of a 37% formaldehyde solution are added and the reaction mixture is boiled under reflux. After 15 minutes of boiling, the reaction is neutralized with ammonia and extracted three times with 200 mL of methylene chloride. The combined organic phases are dried over sodium sulfate, filtered and the solvent is evaporated under vacuum. Chromatographic purification of the residue (600 mg of silica gel) CHCl$_3$: MeOH=9:1:→8:2) results in a colorless foam. Yield: 6.4 g (66.2%).

Method of Synthesizing rac., (−) or (+) bromogalanthamine (1,3, III)

Method A

To a solution of 4.00 g (10.8 mmoles) of nivaline in 40 mL of 30% formic acid, 40 mL of 30% hydrogen peroxide solution are added and the reaction mixture is heated rapidly to 100° C. After 20 minutes, the reaction mixture is cooled rapidly to room temperature, made alkaline with concentrated aqueous ammonia and extracted three times with 50 mL of ethyl acetate. The organic phase is washed once with saturated, aqueous sodium chloride solution, dried (sodium sulfate), filtered and evaporated, 2.55 g (64% of the theoretical yield) of colorless crystals with a melting point of 76°–77° C. and a rotation of $\alpha_D^{20}$[CHCl$_3$]=−93° of 3 being obtained. TLC: CHCl$_3$: MeOH=9:1

Method B

A solution of 1.0 g (2.84 mmoles) of rac. N-demethylbromogalanthamine (4) in 1 mL of 37% of formaldehyde, 2 mL of formic acid and 5 mL of water are stirred for 3 hours at 70° C. The solution is allowed to cool, made alkaline with concentrated aqueous ammonia and left to crystallize for 20 hours at 4° C. The precipitate is filtered off, dried at 50° C./20 mm, 0.85 g (82% of the theoretical yield) of colorless crystals of 1, melting at 76° to 77° C. being obtained.

TLC: CHCl$_3$: MeOH=9:1

Method C

See the general procedure for the reduction with L-selectride.

NMR data of (1,3, III)

$^1$H-NMR (CDCl$_3$; δ (ppm)): 1.60 (ddd, 1H, H-9, $J_{(9,9')}$=14.2 Hz); 1.90–2.15 (m, 2H, H-9'/5, $J_{(5,5')}$=15.1 Hz); 2.20 (b, 1H tauscht D$_2$O, OH); 2.45 (s, 3H, NCH$_3$); 2.65 (ddd, 1H, H-5', $J_{(5,5')}$=15.1 Hz); 2.95 (ddd, 1H, H-10, $J_{(10,10')}$=15.6 Hz); 3.25 (ddd, 1H, H-10', $J_{(10,10')}$=15.6 Hz); 3.80 (s, 3H, OCH$_3$); 3.95 (d, 1H, H-12, $J_{(12,12')}$=16.0 Hz); 4.15 (dd, 1H, H-6); 4.30 (d, 1H, H-12', $J_{(12,12')}$=16.0 Hz); 4.60 (b, 1H-4a); 5.95–6.10 (m, 2H, H-7/8); 6.90 (s, 1H, H-2)

$^{13}$C-NMR (CDCl$_3$; δ (ppm)): 29.7 (t, C-5); 33.5 (t, C-9); 42.1 (q, NCH$_3$); 48.6 (s, C-8a); 53.3 (t, C-10); 55.9 (q, OCH$_3$); 58.7 (t, C-12); 61.6 (d, C-6); 88.6 (d, C-4a); 114.2 (s, C-1); 115.6 (d, C-8); 126.5 (t, C-2); 127.6 (s, C-12a); 127.9 (t, C-7); 134.0 (s, C-12b); 144.0 (s, C-3a); 145.3 (s, C-3)

N-Demethylbromogalanthamine (4)

Method A

N-formyl bromonarwedine (50.0 g, 132 mmoles) is suspended in 250 mL of absolute tetrahydrofuran and treated at −25° to −20° C. with 430 mL (430 mmoles) of a 1N solution of L-selectride in tetrahydrofuran. After 3 hours, the reaction mixture is hydrolyzed with a 1:1 solution of ethanol in tetrahydrofuran, concentrated to about 200 mL, treated with 400 mL of ethanol and once again concentrated to 200 mL, in order to remove the borate ester. The residue is taken up in 500 mL of ethanol, treated with 62% aqueous hydrobromic acid until a pH of 1 is reached and stirred for 24 hours at room temperature. The resulting precipitate is filtered off with suction and washed with a little ethanol. After being dried, the precipitate is dissolved in 500 mL of water. The aqueous phase is slowly made alkaline with concentrated aqueous ammonia while being cooled and stirred well, so that the product precipitates. The precipitate is left to crystallize in the refrigerator and then filtered off with suction. By extraction of the filtrate with ethyl acetate, a second fraction of the product is obtained, the total yield being 33.5 g (72% of the theoretical yield) of colorless crystals of 4.

TLC: $CHCl_3$: MeOH-95:5

Method B

See general procedure for reducing with L-selectride.

$^1$H-NMR ($CDCl_3$; δ (ppm)): 1.65–1.85 (m, 2H, H-9/9'), 1.98 (ddd, 1H, H-5); 2.25 (b, 2H tauschen $D_2O$, NH/OH); 2.62 (ddd, 1H, H-5'); 3.05–3.35 (m, 2H, H-10/10'); 3.80 (s, 3H, $OCH_3$); 3.85 (d, 1H, H-12, $J_{(12,12')}$=14.7 Hz); 4.10 (dd, 1H, H-6); 4.48 (d, 1H, H-12', $J_{(12,12')}$=14.7 Hz); 4.56 (b, 1H, H-4a); 5.90–6.05 (m, 2H, H-7/8); 6.85 (s, 1H, H-2)

$^{13}$C-NMR ($CDCl_3$; δ (ppm)): 29.7 (t, C-5); 39.8 (t, C-9); 46.6 (t, C-10); 49.3 (s, C-8a); 52.7 (t, C-12); 56.0 (q, $OCH_3$); 61.7 (d, C-6); 88.4 (d, C-4a); 113.0 (s, C-1); 115.5 (d, C-8); 126.8 (d, C-2); 127.9 (d, C-7); 131.6 (s, C-12a); 134.1 (s, C-12b); 144.0 (s, C-3a); 145.8 (s, C-3)

(+/−) N-Demethyl-bromogalanthamine (4), (+/−) N-Demethyl-epibromogalanthamine (7)

To a suspension of 1.0 g (2.6 mmoles) of bromo-N-formyl narwedine in 5 mL of THF, 3.0 g (11.8 mmoles) of LiAlH (t-BuO)$_3$ in 15 mL of THF is added dropwise at 0° C. over a period of 30 minutes. After being stirred at 0° C. for 30 minutes, the reaction mixture is refluxed. After 22 hours of refluxing, the complex, formed with the reagent, is decomposed with water and the reaction mixture treated with 10 mL of 25% ammonia solution. After 30 minutes of stirring at room temperature, 50% of the solvent is evaporated under vacuum, the remainder is transferred to a separating funnel, mixed with 10 mL of 25% ammonia solution and extracted three times with 20 mL of methylene chloride. The combined organic phases are extracted with sodium sulfate and filtered and the solvent is evaporated under vacuum. Chromatographic purification of the residue (60 g of silica gel) $CHCl_3$: MeOH=95:5→9:1→8:2) results in two products: 300.0 mg (32.2%) of N-demethyl-bromogalanthamine (4) as a colorless foam and 270 mg (29.0%) of N-demethyl-epibromogalanthamine (7) as a colorless foam.

N-demethyl-epibromogalanthamine (7) data:

Molecule: $C_{16}H_{18}BrNO_3$: 352,21

IR(KBr): 781,60w; 834,28w; 976,63w; 1050,28m; 1179, 73m; 1211,87m; 1280,07m; 1435,24m; 1486,10 m; 1616,37 m; 2923,54 w; 3700–2900mbr.

$^1$H-NMR ($CDCl_3$): 6,86 (s, 1H); 5,92 (AB, 2H); 4,56 (m, 2H); 4,50 and 3,82 (AB, 2H); 3,80 (s, 3H); 3,28, (m, 2H) 2,52 (m, 1H); 2,20–1,70 (m, 3H).

$^{13}$C-NMR ($CDCl_3$):146,73s; 143,91s; 134,10s; 132, 17s;132,17d; 131,48d; 126,34d; 115,34d; 112,44s; 88,51d; 62,81d; 56,10q; 52,34t; 49,25s; 46,82t; 40,52t; 32,07t.

(−)-N-Demethylbromogalanthamine (5) and (−)-N-Demethylbromogalanthamine (6)

(−)-N-Demethylbromogalanthamine (5)

To a solution of 10.0 g (28.4 mmoles) of rac. N-demethylbromogalanthamine (4) in 30 mL of methanol, a solution of 4.4 g (11.4 mmoles) of (−)-O,O-di-p-toluoyl tartaric acid in 5 mL of methanol is added dropwise and subsequently rinsed with 1 mL of ethanol. The solution is seeded (without seeding, crystal formation can take several weeks) and allow to stand for 2 days at 4° C. After scratching with a glass rod, the solution is left standing for a further 2 to 5 days at 4° C., scratching with a glass rod being repeated several times. Subsequently, the precipitate itself is filtered off with suction, washed three times with ice cold methanol and taken up in 100 mL of water. The aqueous phase is made alkaline with aqueous ammonia and extracted three times with 60 mL of ethyl acetate. The combined organic phases are washed once with saturated aqueous sodium chloride solution, dried (sodium sulfate, activated charcoal), filtered and evaporated, 1.90 g (38% of the theoretical yield) of colorless crystals with a rotation of $α_D^{20}$ [$CHCl_3$]=−104° (after CE:>99.9%) of 5 being obtained. The methanol mother liquor is evaporated, the residue taken up in 100 mL of water and treated in the same way as the pure salt above, 7.13 g (88% of the theoretical yield) of crude product being recovered, which is used for obtaining 6.

(−)-N-Demethylbromogalanthamine (6)

To a solution of 7.13 g (20.2 mmoles) of recovered (from 5) N-demethylbromogalanthamine (this slightly concentrated product forms crystals more rapidly than racemic (4)) in 10 mL of methanol, a solution of 3.12 g (8.1 mmoles) of (+)-O,O-di-p-toluoyl tartaric acid in 4 mL of methanol is added dropwise, a further 1 mL of methanol being used for rinsing. The solution is seeded with a crystal (without seeding, crystal formation can take several weeks) and treated as in the recovery of 5, 2.02 g (57% of the theoretical yield) of colorless crystals with a rotation of $α_D^{20}$ [$CHCl_3$]=+102° (after CE:>99.9%) of 6

| $C_{16}H_{18}BrNO_3$ * 1.05 $C_{20}H_{18}O_8$ * 1.02 $H_2O$ (JOS 1500) 776.11 g/mol | | |
|---|---|---|
| calculated: | C 57.26 | H 5.05 | N 1.80 |
| found: | C 57.28 | H 5.12 | N 1.82 |

(+/−) Bromo-N-formyl narwedine propylene glycol ketal (8)

Bromo-N-formyl narwedine (100 g) of propylene glycol and 0.5 g of sulfuric acid in 800 mL of toluene (two phases at room temperature) are refluxed with vigorous mechanical stirring (above about 90° C., homogeneous) for 14 hours with removal of water. After cooling, the phases were separated (the toluene phase being the upper phase) the propylene glycol phase was extracted twice with 100 mL of toluene, the combined toluene phases were shaken twice with 200 mL of saturated $NaHCO_3$ solution, dried over sodium sulfate and evaporated: Yield: 115.3 g of a yellowish foam (8) (100% of the theoretical yield, crude), which crystallized overnight. Column chromatography of 1.0 g (60 g of silica gel 60, $CHCl_3$/1–2% MeOH) resulted in 0.80 g of a colorless foam, which crystallized from ethyl acetate. Melting point: 170°–171° C.

| Molecule | $C_{20}H_{22}BrNO_5$: | 436.23 |
|---|---|---|

$^1$H-NMR ($CDCl_3$): 8.12 (d, H), 6.88 (s, H), 5.96–6.17 (m, H) 5.75 (dd, H), 5.68 (d, H/2), 5.10 (d, H/2), 4.53 (b, H) 4.48 (d, H/2), 4.31 (d, H/2), 3.12–4.38 (m, 5H), 3.82 (s, 3H), 2.56–2.80 (m, H), 2.05–2.35 (dd, H) 1.83–2.05 (m, 2H) 1.22–1.47 (m, 3H).

$^{13}$C-NMR (CDCl$_3$): 162.48, 161.72, 147.17, 144.89, 144.64, 132.16, 129.04, 128.51, 128.57, 127.82, 127.70, 127.61, 115.70, 115.48, 127.09, 126.77, 126.5, 113.20, 111.66, 102.38, 102.22, 87.25, 87.07, 73.38, 72.46, 71.67, 71.41, 71.23, 70.55, 70.28, 55.92, 51.52, 46.18, 48.43, 40.77, 39.29, 36.07, 35.97, 34.58, 33.68, 33.44, 33.13, 18.68, 17.59, 17.45.

Comment—NMR, diastereoisomers: Because of the additionally introduced chiral center by means of the (+/−) propylene group, diastereoisomers are formed, which cause signal splitting in addition to that caused by the formyl group.

(+/−) Narwedine-propylene glycol ketal (9)

LiAlH$_4$ (37.5 g) is added under argon into a previously dried, 4 L multi-neck flask, into which 800 mL of THF are then run from a dropping funnel. The temperature rises with vigorous foaming to about 45° C. (depends on the water content of the THF and of the reaction flask).

A suspension of 114 g of (8) (crude) in THF was added dropwise over 15 minutes, the temperature increasing to the refluxing temperature (65°–68° C.). Refluxing with mechanical stirring was now continued for 10 hours, after which the reaction mixture was cooled. 100 mL of water in 100 mL of THF were then added dropwise with cooling.

Removal of 10 mL, making alkaline with ammonia, extraction with ethyl acetate (3×20 mL) and evaporation yielded an oily product (9). Column chromatography (5 g of silica gel 60, CHCl$_3$/3–5% MeOH) of 0.17 g resulted in 0.1 g of colorless foam.

Molecule: (C$_{20}$H$_{25}$NO$_4$): 343.42

$^1$H-NMR (CDCl$_3$): 6.60 (dd, 2H), 6.16 (dt, H), 5.68 (dd, H), 4.55 (m, H), 4.38–4.00 (m, 3H), 3.80 (s, 3H), 3.68–2.95 (m, 4H), 2.78–2.60 (m, H), 2.35 (s, 3H), 2.24–2.02 (m, 2H), 1.62 (bd, H) 1.28 (t, 3H).

$^{13}$C-NMR (CDCl$_3$): 146.59, 143.92, 132.04, 131.90, 129.57, 129.16, 128.86, 128.76, 128.39, 127.44, 126.92, 126.12, 126.02, 121.16, 111.05, 110.90, 110.77, 102.87, 102.73, 87.23, 73.15, 72.24, 71.43, 71.12, 70.44, 70.17, 60.28, 55.59, 55.53, 55.45, 53.83, 47.87, 47.80, 47.75, 41.80, 41.70, 34.84, 33.95, 33.66, 33.37, 18.66, 17.62, 17.43.

Comment—NMR, diastereoisomers: Because of the additionally introduced chiral center by means of the (+/−) propylene group, diastereoisomers are formed, which cause signal splitting in addition to that caused by the formyl group.

N-formyl bromonarwedine ethylene glycol ketal (10)

N-formyl bromonarwedine (10.0 g, 26.5 mmoles) in 20 g of ethylene glycol and 200 mL of toluene are refluxed with 0.1 mL of concentrated sulfuric acid using a water separator. After 24 hours, the toluene phase is decanted off and the ethylene glycol phase boiled out once with toluene. The combined toluene phases are washed twice with saturated, aqueous, sodium hydrogen carbonate solution and evaporated, colorless crystals of 10, melting at 192°–193° C. being obtained quantitatively. EtOAc: MeOH=99:1

$^1$H-NMR (CDCl$_3$; δ (ppm)): 1.75–2.10 (m, 2H, H-9/9'); 2.15 (dd, 1H, H-5, J$_{(5,5')}$=16.5 Hz); 2.65 (dd, 1H, H-5', J$_{(5/5')}$=16.5 Hz); 3.60 (ddd, 1H, H-10); 3.80 (s, 3H, OCH$_3$); 3.90–4.10 (m, 5H, H-10', O—CH$_2$—CH$_2$—O); 4.30 (d, 1H, H-12$_{Conformer\ A}$, J$_{(12,12')}$=17.8 Hz); 4.50 (d, 1H, H-12$_{Conformer\ B}$); 4.55 (b, 1H, H-4a); 5.10 (d, 1H, H-12'$_{Conformer\ A}$, J$_{(12,12')}$=17.8 Hz); 5.65 (d, 1H, H-12'$_{Conformer\ B}$); 5.70 (d, 1H, H-8); 6.10 (t, 1H, H-7); 6.85 (s, 1H, H-2); 8.10, 8.15 (2* s, 1H, CHO$_{Conformer\ A/B}$)

$^{13}$C-NMR (CDCl$_3$; δ (ppm)): 32.9 (t, C-5); 36.0 (t, C-9); 39.3, 40.7 (2* t, C-10$_{Conformer\ A/B}$); 48.4 (s, C-8a); 46.1, 51.4 (2* t, C-12$_{Conformer\ A/B}$); 55.9 (q, OCH$_3$); 64.2, 65.1 (2* t, O—CH$_2$—CH$_2$—O); 86.9, 87.1 (2* s, C-4a$_{Conformer\ A/B}$); 102.0 (s, C-6); 111.6 (d, C-2); 115.4, 115.7 (2* d, C-8$_{Conformer\ A/B}$); 126.4 (s, C-12a); 126.7 (s, C-1); 127.5, 127.7 (2* t, C-7$_{Conformer\ A/B}$); 132.0, 132.1 (2* S, C-12b$_{Conformer\ A/B}$); 144.6, 144.8 (2* S, C-3a$_{Conformer\ A/B}$); 147.1 (s, C-3); 161.6, 162.4 (2* s, CHO$_{Conformer\ A/B}$)

Narwedine ethylene glycol ketal (11)

Method A

To a suspension of 2.0 g (4.74 mmoles) of 10 in 50 mL of absolute tetrahydrofuran, 20 mL of a 0.9 molar lithium aluminum hydride solution in diethyl ether are added dropwise at 0° C. The reaction mixture is subsequently allowed to warm up to room temperature and finally refluxed (boiling point: 52° C.). After 50 hours, the reaction mixture is cooled and hydrolyzed with 3 mL of a 2:1 mixture of tetrahydrofuran and water. After that, 50 mL of water and 50 mL of concentrated aqueous ammonia are added and the aqueous is extracted three times with 50 mL of ethyl acetate. The combined organic phases are washed once with saturated sodium chloride solution, dried (sodium sulfate) and evaporated. By purification with MPLC using EtOAc: MeOH=8:2, 820 mg (52% of the theoretical yield) of colorless crystals of 11, melting at 109°–110° C. are obtained.

TLC: CHCl$_3$: MeOH=9:1

Method B (−) Narwedine (1.0 g, 3.5 mmoles) in 2.0 g of ethylene glycol and 20 mL of toluene are refluxed with 0.05 mL of concentrated sulfuric acid using a water separator. After 24 hours, the toluene phase is decanted off and the ethylene glycol phase boiled out once with toluene. The combined toluene phases are washed twice with saturated, aqueous sodium hydrogen carbonate solution and evaporated, colorless crystals of 11 being obtained quantitatively.

TLC: CHCl$_3$: MeOH=9:1

$^1$H-NMR (CDCl$_3$; δ (ppm)): 1.65 (ddd, 1H, H-9, J$_{(9,9')}$=13.4 Hz); 2.10 (ddd, 1H, H-9', J$_{(9,9')}$=13.4 Hz); 2.15 (dd, 1H, H-5, J$_{(5,5')}$=14.2 Hz); 2.40 (s, 3H, NCH$_3$); 2.65 (dd, 1H, H-5', J$_{(5,5')}$=14.2 Hz); 3.05 (ddd, 1H, H-10); 3.20 (ddd, 1H, H-10'); 3.60 (d, 1H, H-12, J$_{(12,12')}$=16.0 Hz); 3.80 (s, 3H, OCH$_3$); 3.90–4.05 (m, 4H, O—CH$_2$—CH$_2$—O); 4.10 (d, 1H, H-12', J$_{(12,12')}$=16.0 Hz); 4.55 (dd, 1H, H-4a); 5.65 (d, 1H. H-8, J$_{(7,8)}$=9.8 Hz); 6.15 (d, 1H, H-7, J$_{(7,8)}$=9.8 Hz); 6.55, 6.60 (AB, 2H, H-1/2)

$^{13}$C-NMR (CDCl$_3$; δ (ppm)): 33.2 (t, C-5); 33.8 (t, C-9); 41.7 (q, N—CH$_3$); 47.8 (t, C-10); 53.8 (s, C-8a); 55.5 (q, OCH$_3$); 60.2 (t, C-12); 64.0, 65.0 (2* t, O—CH$_2$—CH$_2$—O); 87.1 (d, C-4a); 102.5 (s, C-6); 110.9 (d, C-8); 121.1 (d, C-2); 125.9 (d, C-7); 128.7 (s, C-12a); 128.9 (s, C-12b); 131.8 (d, C-1); 143.8 (s, C-3a); 146.5 (s, C-3)

(+/−) Galanthamine-2-hydroxyethyl ether (12)

To the educt (10) (1.0 g), dissolved in 25 mL of THF and cooled to 0° C., 9 mL of a 1M solution of lithium aluminum hydride in THF were added dropwise over a period of 5 minutes and stirring was continued at 0° C. for 30 minutes. Subsequently, the reaction mixture was refluxed for 48 hours and cooled and 25 mL (25%) ammonia were added dropwise, after which 4 mL of the reaction mixture were extracted with 20 mL of ethyl acetate. The organic phases were dried over sodium sulfate and evaporated. Yield: 0.76 g of a yellowish oil (12) (92.9% of the theoretical yield). Column chromatography (40 g of silica gel 60, $CHCl_3$/2–7% of MeOH) resulted in 0.62 g of colorless foam. Molecular weight ($C_{19}H_{24}NO_4$): 330.40

N-Demethylbromonarwedine ethylene glycol ketyl (13)

N-formylbromonarwedine ethylene glycol ketal (9.0 g, 21.3 mmoles) (10) is suspended in 100 mL of absolute tetrahydrofuran, treated at –15° to at most –10° C. with 28.4 mL (25.6 mmoles) of a 0.9 N solution of lithium aluminum hydride in diethyl ether and stirred at this temperature. After 20 minutes, a further 10 mL of a 0.9 N lithium aluminum hydride solution in diethyl ether are added dropwise and stirred for a further 20 minutes at –15° to –10° C. Subsequently, the reaction mixture is hydrolyzed with 15 mL of 2:1 mixture of tetrahydrofuran and water, the solution is concentrated in a rotary evaporator and the residue taken up in 200 mL of water and extracted three times with 100 mL portions of ethyl acetate. The combined organic phases are washed with a saturated, aqueous sodium chloride solution, dried (sodium sulfate) and evaporated, 6.53 g (78% of the theoretical yield) of colorless crystals of 13 being obtained.

DC: $CHCl_3$: MeOH=95:5 EtOAc: MeOH=9:1

$^1$H-NMR ($CDCl_3$; δ (ppm)): 1.70–1.85 (b, 1H tauscht $D_2O$, NH; 1.80 (dd, 1H, H-9); 1.90 (dd, 1H, H-9'); 2.15 (dd, 1H, H-5, $J_{(5,5')}$=16.0 Hz); 2.65 (dd, 1H, H-5', $J_{(5,5')}$=16.0 Hz); 3.20 (ddd, 1H, H-10); 3.80 (s, 3H, $OCH_3$); 3.85–4.10 (m, 6H, H-10'/12, HO—$CH_2$—$CH_2$—O); 4.50 (d, 1H, H-12', $J_{(12, 12')}$=14.2 Hz); 4.60 (dd, 1H, H-4a); 5.65 (dd, 1H, H-8, $J_{(7,8)}$=9.8 Hz); 6.15 (dd, 1H, H-7, $J_{(7,8)}$=9.8 Hz); 6.85 (s, 1H, H-2)

N-Benzyl-bromonarwedine ethylene glycol ketal (14)

N-demethylbromonarwedine ethylene glycol ketal (250 mg, 0.63 mmoles) (13) is mixed with 63 mg (0.63 mmoles) of triethylamine in 15 mL of absolute tetrahydrofuran and 108 mL (0.63 mmoles) of benzyl bromide are added at room temperature and the mixture is subsequently stirred for 24 hours. The reaction mixture is treated with 50 mL of water and the aqueous phase extracted three times with 20 mL portions of ethyl acetate. The combined organic phases are washed once with saturated, aqueous sodium chloride solution, dried (sodium sulfate) and evaporated, 260 mg (85% of the theoretical yield) of colorless crystals having a melting point of 118° C.–119° C. of 14 being obtained. TLC: EtOAc: MeOH=9:1

$^1$H-NMR ($CDCl_3$; δ (ppm)): 1.65 (ddd, 1H, H-9, $J_{(9,9')}$=14.2 Hz); 2.05–2.30 (m, 2H, H-5, H-9'); 2.65 (dd, 1H, H-5', $J_{(5,5')}$=13.4 Hz); 3.00–3.30 (m, 2H, H-10/10'); 3.70 (s, 2H, $CH_2$—Ph); 3.80 (s, 3H, $OCH_3$); 3.90–4.20 (m, 5H, H-12, O—$CH_2$—$CH_2$—O); 4.35 (dd, 1H, H-12', $J_{(12,12')}$=15.1 Hz); 4.60 (ddd, 1H, H-4a); 5.70 (d, 1H, H-8, $J_{(7,8)}$=9.8 Hz); 6.25 (d, 1H, H-7, $J_{(7,8)}$=9.8 Hz); 6.85 (s, 1H, H-2); 7.25–7.30 (m, 5H, Ph)

$^{13}$C-NMR ($CDCl_3$; δ (ppm)): 33.1 (t, C-5); 33.4 (t, C-9); 48.5 (s, C-8a); 50.7 (t, C-10); 55.8 (q, $OCH_3$); 56.4 (t, C-12); 56.9 (t, $CH_2$—Ph); 64.2, 65.1 (2* t, O—$CH_2$—$CH_2$—O); 87.4 (d, C-4a); 102.3 (s, C-6); 113.6 (s, C-1); 115.6 (d, C-8); 126.6 (s, Ph-1); 127.1 (d, C-7); 128.2, 128.9 (6* d, Ph-2–6, C-2); 133.1 (s, C-12a); 137.9 (s, C-12b); 144.2 (s, C-3a); 146.3 (s, C-2)

N-demethylbromonarwedine (15)

Method A

See general procedure for splitting the ethylene glycol protective group.

Method B

N-formyl bromonarwedine ketal (10) (9.0 g, 21.3 mmoles) are suspended in 100 mL of absolute tetrahydrofuran, treated at –25° to not more than –20° C. with 28.4 mL (25.6 mmoles) of a 0.9N lithium aluminum hydride solution in diethyl ether and stirred at this temperature. After 20 minutes, a further 10 mL (9.0 mmoles) of a 0.9N lithium aluminum hydride solution in diethyl ether are added dropwise and stirred for a further 20 minutes at –25° to –20° C. Subsequently, the reaction mixture is hydrolyzed with 15 mL of a 2:1 mixture of tetrahydrofuran and water and evaporated in a rotary evaporator and the residue is taken up in 200 mL of 2N hydrochloric acid and stirred for 15 minutes. The aqueous phase is treated with 5.71 g (38.1 mmoles) of L-(+)-tartaric acid, made alkaline with concentrated aqueous ammonia and extracted three times with 100 mL of ethyl acetate. The combined organic phases are washed with saturated, aqueous sodium chloride solution, dried (sodium sulfate) and evaporated, 6.53 g (78% of the theoretical yield) of colorless crystals of 15 being obtained.

DC: $CHCl_3$: MeOH=95:5 EtOAc: MeOH=9:1

$^1$H-NMR ($CDCl_3$; δ (ppm)): 1.90–2.15 (m, 2H, H-9/9'); 2.75, 2.95 (AB, 2H, H-5/5', $J_{(5,5')}$=16.0 Hz); 3.10–3.35 (m, 2H, H-10/10'); 3.75 (s, 3H, O—$CH_3$); 3.90 (d, 1H, H-12, $J_{(12,12')}$=16.4 Hz); 4.40 (d, 1H, H-12', $J_{(12,12')}$=16.4 Hz); 4.55 (dd, 1H, H-4a); 5.90 (d, 1H, H-8, $J_{(7,8)}$=10.7 Hz); 6.90 (s, 1H, H-2); 7.05 (d, 1H, H-7, $J_{(7,8)}$=10.7 Hz)

$^{13}$C-NMR ($CDCl_3$; δ (ppm)): 36.3 (t, C-5); 37.0 (t, C-9); 45.6 (s, C-8a); 49.5 (t, C-10); 51.3 (t, C-12); 55.9 (q, $OCH_3$); 87.9 (d, C-4a); 112.5 (s, C-1); 116.0 (d, C-8); 126.6 (d, C-7); 129.6 (s, C-12a); 132.0 (s, C-12b); 143.7 (s, C-3a); 144.8 (d, C-2); 146.6 (s, C-3)

Bromonarwedine (16)

Method A

See general procedure for splitting the ethylene glycol protective group.

Method B

N-formyl bromonarwedine ketal (10) (9.0 g, 21.3 mmoles) are suspended in 100 mL of absolute tetrahyrofuran, treated at –5° to not higher than 0° with 10.0 mL (26.0 mmoles) of a 2.6N lithium aluminum hydride solution in tetrahydrofuran and stirred at this temperature. After 20 minutes, a further 5 mL (13.0 mmoles) of a 2.6N solution of lithium aluminum hydride in tetrahydrofuran are added dropwise and stirred for a further 20 minutes at –5° to 0° C. The solution is subsequently hydrolyzed with 15 mL of a 2:1 mixture of tetrahydrofuran and water and evaporated in a rotary evaporator and the residue is taken up in 200 mL of 2N hydrochloric acid and stirred for 15 minutes. The aqueous phase is treated with 6.4 g (42.9 mmoles) of L-(+)-tartaric acid, made alkaline with concentrated aqueous ammonia and extracted three times with 100 mL of ethyl acetate. The combined organic phases are washed with saturated, aqueous sodium chloride solution, dried (sodium sulfate) and evaporated, 6.21 g (80% of the theoretical yield) of colorless crystals of 16 being obtained.

DC: $CHCl_3$: MeOH=95:5 EtOAc: MeOH=9:1

$^1$H-NMR ($CDCl_3$; δ (ppm)): 1.90 (ddd, 1H, H-9, $J_{(9,9')}$=12.5 Hz); 2.25 (ddd, 1H, H-9', $J_{(9,9')}$=12.5 Hz); 2.45 (s, 3H, $NCH_3$); 2.75 (dd, 1H, H-5, $J_{(5,5')}$=17.8 Hz); 2.95–3.25 (m, 3H, H-5'/10/10'); 3.85 (s, 3H, $OCH_3$); 3.95 (d, 1H, H-12, $J_{(12,12')}$=16.9 Hz); 4.25 (d, 1H, H-12', $J_{(12,12')}$=16.9 Hz);4.70

(dd, 1H, H-4a); 6.05 (d, 1H, H-8, $J_{(7,8)}$=9.8 Hz); 6.95 (s, 1H, H-2); 7.00 (d, 1H, H-7, $J_{(7,8)}$=9.8 Hz)

$^{13}$C-NMR (CDCl$_3$; δ (ppm)): 33.0 (t, C-5); 36.9 (t, C-9); 42.9 (q, NCH$_3$); 49.2 (s, C-8a); 53.5 (t, C-10); 56.1 (q, OCH$_3$); 58.9 (t, C-12); 88.0 (C-4a); 114.0 (s, C-1); 116.3 (d, C-2); 127.2 (d, C-8); 127.9 (s, C-12a); 131.6 (s, C-12b); 143.9 (s, C-3a); 144.4 (d, C-7); 146.5 (s, C-3); 193.9 (s, C-6)

| Splitting Off of The Ethylene Glycol Protective Group (15, 16, Narwedine) | | | | |
|---|---|---|---|---|
| Substance No. | Educt No. | $R_1$ | $R_6$ | empirical weight, molecular weight |
| 15 | 13 | Br | H | |
| Narwedin | 11 | H | CH$_3$ | C$_{17}$H$_{19}$NO$_3$ [285.35] |
| 16 | 110 | Br | CH$_3$ | C$_{17}$H$_{18}$BrNO$_3$ [364.25] |

Educt (5 g) is dissolved in 100 mL of 2N hydrochloric acid and heated to 100° C. for 30 minutes. After cooling, the solution is made alkaline with concentrated aqueous ammonia and the product filtered off with suction and dried at 50° C./20 mm, or extracted with ethyl acetate, dried (sodium sulfate) and evaporated.

TLC: CHCl$_3$: MeOH=9:1

| Substance No | Name | Yield | Melting Point |
|---|---|---|---|
| 15 | Narwedin | 91% colorless crystals quantitative colorless crystals | 173–174° C. |
| Narwedin | Narwedin | | |
| 16 | Bromnarwedin | quantitative colorless crystals | 75–77° C. |

Narwedin $^1$H-NMR (CDCl$_3$; δ (ppm)): 1.85 (ddd, 1H, H-9, $J_{(9,9')}$=14.2 Hz); 2.25 (ddd, 1H, H-9', $J_{(9,9')}$=14.2 Hz); 2.75 (ddd, 1H, H-5, $J_{(5,5')}$=17.8 Hz); 3.05–3.30 (m, 3H, H-5'/10/10'); 3.70 (d, 1H, H-12, $J_{(12,12')}$=12.5 Hz); 3.80 (s, 3H, OCH$_3$); 4.10 (d, 1H, H-12', $J_{(12,12')}$=12.5 Hz); 4.70 (b, 1H, H-4a); 6.00 (d, 1H, H-8, $J_{(7,8)}$=9.8 Hz); 6.60–6.70 (m, 2H, H-1/2); 6.95 (d, 1H, H-7, $J_{(7,8)}$=9.8 Hz)

$^{13}$C-NMR (CDCl$_3$; δ rpm)): 33.3 (t, C-5); 37.3 (t, C-9); 42.5 (q, NCH$_3$); 49.0 (s, C-8a); 54.1 (t, C-10); 56.0 (q, OCH$_3$); 60.7 (t, C-12); 88.0 (d, C-4a); 111.9 (d, C-2); 122.0 (d, C-8); 127.1 (d, C-1); 129.4 (s, C-12a); 130.6 (s, C-12b); 144.0 (d, C-7); 144.4 (s, C-3a); 147.0 (s, C-2); 194.4 (s, C-6)

| General Procedure for Reduction with L-Selectide | | | | |
|---|---|---|---|---|
| Substance No. | Educt No. | $R_1$ | $R_6$ | empirical formula, molecular weight |
| 4 | Bromformyl narwedin | Br | ＼H | C$_{16}$H$_{18}$BrNO$_3$ [352.24] |
| 3 | Bromnarwedin | Br | ＼CH$_3$ | C$_{17}$H$_{20}$BrNO$_3$ [366.26] |
| 42 | 41 | Br | ＼／＝ | C$_{19}$H$_{22}$BrNO$_3$ [392.30] |

| General Procedure for Reduction with L-Selectide | | | | |
|---|---|---|---|---|
| Substance No. | Educt No. | $R_1$ | $R_6$ | empirical formula, molecular weight |
| 45 | 44 | Br | 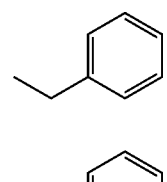 | C$_{23}$H$_{24}$BrNO$_3$ [442.36] |
| 46 | 47 | H | 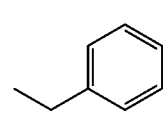 | C$_{23}$H$_{25}$NO$_3$ [363.46] |

Educt (100 mg) is suspended in 5 mL of absolute tetrahydrofuran and treated at −5° to 0° C. with 1.2 equivalents of a 1N solution of L-selectide in tetrahydrofuran. After 30 minutes, the reaction mixture is hydrolyzed with a 1:1 mixture of tetrahydrofuran and water and evaporated to dryness in a rotary evaporator, the residue being taken up in 50 ml of 2N hydrochloric acid and stirred overnight at room temperature. The aqueous phase is washed with 20 mL of diethyl ether and made alkaline slowly with cooling and good stirring with concentrated aqueous ammonia, so that the product precipitates. The precipitate is permitted to crystallize for several days in the refrigerator and then filtered off with suction. By extracting the filtrate with ethyl acetate, a second fraction of product is recovered. The crude product is purified by column chromatography (15 g silica gel, solvent: a 9:1 mixture of chloroform and ethanol).

TLC: CHCl$_3$: MeOH=9:1

| Substance No. | Name | Yield | Melting Point |
|---|---|---|---|
| 4 | (6R)-4a,5,9,10,11,12-Hexahydro-1-brom-3-methoxy-6H-benzafuro[3a,3,2-ef][2]benzazepin-6-ol | 90% colorless crystals | |
| 3 | (6R)-4a,5,9,10,11,12-Hexahydro-1-brom-3-methoxy-11-methyl-6H-benzafuro[3a,3,2-ef][2]benzazepin-6-ol | quantitative colorless crystals | 76–77° C. |
| 42 | (6R)-4a,5,9,10,11,12-Hexahydro-1-brom-3-methoxy-11-(2-propenyl)-6H-benzofuro[3a,3,2-ef][2]-benzazepin-6-ol | 30% | |
| 45 | (6R)-4a,5,9,10,11,12-Hexahydro-1-brom-3-methoxy-11-(phenylmethyl)-6H-benzofuro[3a,3,2-ef][2]-benzazepin-6-ol | 50% | |
| 46 | (6R)-4a,5,9,10,11,12-Hexahydro-3-methoxy-11-(phenylmethyl)-6H-benzofuro[3a,3,2-ef][2]benzazepin-6-ol | 80% | |

| Product | Empirical Formula | R | Method | R |
|---|---|---|---|---|
|  | $C_{24}H_{26}N_2O_4$ [406.48] | (−)-Galanthamin-phenylcarbamate | A |  |
| 17 | $C_{26}H_{29}N_2O_4$ [433.53] | (−)-Galanthamin-R-α-methyl-benzylcarbamate | A |  |
| 19 | $C_{26}H_{29}N_2O_4$ [433.53] | (−)-Galanthamin-S-α-methyl-benzylcarbamate | A |  |
|  | $C_{23}H_{28}N_2O_4$ [456.54] | (−)-Galanthamin-α-naphtylcarbamate | B |  |
|  | $C_{22}H_{30}N_2O_4$ [386.49] | (−)-Galnthamin-n-butylcarbamate | A |  |
| 21 | $C_{24}H_{26}N_2O_3S$ [422.55] | (−)-Galanthamin-phenylthiocarbamate | B |  |
| 23 | $C_{22}H_{30}N_2O_3S$ [402.56] | (−)-Galanthamin-n-butylthiocarbamate | B |  |

(−)-Galanthamine Carbamates and Thiocarbamates

Method A

Isothionate or thioisothianate (1.2 equivalents) is added under argon to a solution of 500 mg (1.74 mmoles) of (−)-galanthamine in 50 mL of absolute tetrahydrofuran and stirred for 24 hours under reflux. The reaction mixture was evaporated and the residue purified by column chromatography (acetone=methanol=9:1), colorless crystals being obtained.

Method B

Sodium hydride (95%, 68 mg, 2.62 mmoles) was added under argon to a solution of 500 mg (1.74 mmoles) of (−)-galanthamine in 15 mL of absolute dimethylformamide and stirred for 30 minutes at room temperature. Subsequently, 1.2 equivalents of isocyanate or thioisocyanate were added dropwise and stirring was continued for a further 3 hours. The reaction mixture was poured into 150 mL of water and extracted twice with 150 mL of ethyl acetate. The organic phases were washed once with 100 mL of water, dried over sodium sulfate and evaporated. The residue was purified by column chromatography (acetone:methanol=9:1), colorless crystals being obtained.

TLC: Toluene: MeOH=4:1

| Product | Yield [% d. Th.] | $*\alpha_D$ (25° C., c = 1) | melting point. [°C.] |
|---|---|---|---|
|  | 94 (Lit.[15]: 80%) | −43.6° | 85–86 (Lit.[15]:85–87) |
|  | 58 (Lit.[15]: 60%) | −56.0° | 199–203 (Lit.[15]:203–204) |
|  | 93 (Lit.[15]: 100%) | −57.0° | 48–51 (Lit.[15]:47–49) |
| 17 | 96 | −45.5° | 74–77 |
| 19 | 99 | −48.1° | 135–136 |
| 21 | 97 | −22.5° | 175–176 |
| 23 | 71 | −48.5° | 165–167 |

| ¹H—NMR [CDCl₃; δ (ppm)]: | | | | |
|---|---|---|---|---|
| Proton | | | | 17 |
| Hₐ-5 | 1.60; m | 1.60; m | 1.58; m | 1.60; m |
| Hₐ-1 | 2.10; m | 2.10; m | 2.10; m | 1.90; m |
| Hᵦ-5 | 2.20; m | 2.18; m | 2.15; m | 2.10; m |
| CH₃—N— | 2.40; s | 2.4; s | 2.40; s | 2.38; s |
| Hᵦ-1 | 2.75; br.d | 2.80; br.d | 2.65; br.d | 2.68; br.d |
| Hᵦ-6 | 3.10; m | 3.08; m | 3.05; m | 3.05; m |
| Hₐ-6 | 3.30; m | 3.30; m | 3.15; m | 3.25; m |
| Hᵦ-8 | 3.70; br.d | 3.68; br.d | 3.65; br.d | 3.65; br.d |
| CH₃—O— | 3.85; s | 3.85; s | 3.85; s | 3.80; s |
| Hₐ-8 | 4.15; br.d | 4.15; br.d | 4.10; br.d | 4.10; br.d |
| H-12a | 4.55; t | 4.59; m | 4.50; t | 4.55; t |
| H-2 | 5.40; t | 5.45; t | 5.23; t | 5.25; t |
| H-3 | 5.95; dd | 6.00; dd | 5.90; dd | 5.85; dd |
| H-4 | 6.30; d | 6.35; d | 6.20; d | 6.25; d |
| H-9 | 6.60; d | 6.60; d | 6.55; d | 6.55; d |
| H-10 | 6.65; d | 6.70; d | 6.60; d | 6.65; d |
| diverse H | 6.95 (s, 1H, —NH—) | 7.35 (s, 1H, —NH—) | 0.9 (t, 3H, CH₃—) | 1,45 (m, 3H, CH₃—) |
| | 7.0–7.3 (m, 5H, Ph) | 7.5–7.9 (m, 7H, Naph) | 1.30 (m, 2H, CH₃—C$\underline{H}$₂—) | 4.48 (m, 1H, —C$\underline{H}$—) |
| | | | 1.42 (m, 2H, (—CH₂C$\underline{H}$₂—)) | 5,20 (s, 1H, —NH—) |
| | | | 3.15 (m, 2H, (—NH—C$\underline{H}$₂—)) | 7,28 (m, 5H, Ar—H) |
| | | | 4.85 (s, 1H, —NH—) | |

| Proton | 19 | 21 | 23 | |
|---|---|---|---|---|
| Hₐ-5 | 1.55; m | 1.60; m | 1.65; m | |
| Hₐ-1 | 2.10; dd | 2.00; m | 2.00; m | |
| Hᵦ-5 | 1.90; m | 2.15; m | 2.10; m | |
| CH₃—N— | 2.40; s | 2.35; s | 2.38; s | |
| Hᵦ-1 | 2.70; br.d | 2.60; m | 2.75; m | |
| Hᵦ-6 | 3.02; m | 3.00; m | 3.05; m | |
| Hₐ-6 | 3.25; m | 3.25; m | 3.50; m | |
| Hᵦ-8 | 3.65; br.d | 3.60; br.d | 3.70; br.d | |
| CH₃—O— | 3.80; s | 3.70; s | 3.80; s | |
| Hₐ-8 | 4.10; br.d | 4.05; br.d | 4.10; br.d | |
| H-12a | 4.55; t | 4.50; t | 4.55; t | |
| H-2 | 5.28; t | 5.90; m | 6.30; t | |
| H-3 | 5.90; dd | 6.00; dd | 5.95; dd | |
| H-4 | 6.20; d | 6.25; d | 6.05; d | |
| H-9 | 6.55; d | 6.50; d | 6.55; d | |
| H-10 | 6.65; d | 6.10; d | 6.65; d | |
| diverse H | 1.50 (d, 3H, CH₃—) | 6.9–7.25 (d, 5H, Ph-H) | 0.90 (t, 3H, CH₃—) | |
| | 4.80 (m, 1H, —NH—C$\underline{H}$—CH₃) | 8.40 (s, 1H, —NH—) | 1.30 (m, 2H, CH₃—C$\underline{H}$₂—) | |
| | 5.20 (s, 1H, —NH—) | | 1.60 (m, 2H, —CH₂—C$\underline{H}$₂—CH₂—) | |
| | | | 3.25 (m, 2H, —NH—C$\underline{H}$₂—) | |

| ¹³C—NMR [CDCl₃; δ (ppm)]: | | | | |
|---|---|---|---|---|
| C-Atom | | | | 17 |
| C-1 | 27.8; t | 27.9; t | 29.1; t | 27.9; t |
| C-5 | 34.1; t | 34.3; t | 34.2; t | 34.2; t |
| CH₃—N— | 41.7; q | 41.9; q | 40.5; q | 41.7; q |
| C-4a | 47.8; s | 47.9; s | 47.7; s | 47.8; s |
| C-6 | 53.6; t | 53.7; t | 53.8; t | 53.6; t |
| CH₃—O | 55.6; q | 55.7; q | 55.5; s | 55.6; s |
| C-8 | 60.3; t | 60.4; t | 60.3; t | 60.3; t |
| C-2 | 63.6; d | 64.0; d | 62.9; d | 63.2; d |
| C-12a | 86.3; d | 86.3; d | 86.3; d | 86.3; d |
| C-3 | 110.9; d | 111.0; d | 110.9; d | 111.0; d |
| C-4 | 118.6; d | 119.0; d | 121.2; d | 121.2; d |
| C-9 | 121.4; d | 120.7; d | 123.4; d | 123.3; d |
| C-10 | 130.4; d | 128.5; d | 129.8; d | 128.3; d |
| C-8a | 132.0; s | 129.2; s | 129.1; s | 129.2; s |
| C-11b | 138.0; s | 132.1; s | 132.1; s | 132.1; s |
| C-11a | 143.7; s | 143.8; s | 143.7; s | 143.6; s |
| C-11 | 146.3; s | 146.4; s | 146.3; s | 146.3; s |
| diverse C | 122.8 (d, Ar—C) | 120.7; 121.4; 123.0; 125.7; | 13.5 (q, C$\underline{H}$₃—CH₂—) | 22.4 (q, CH₃—) |
| | 123.0 (d, Ar—C) | 125.9; 130.6 (d, 6 naphth.C) | 19.7 (t, CH₃—C$\underline{H}$₂—) | 50.6 (d, —NH—CH—) |
| | 128.7 (d, 3 Ar—C) | 126.7 (s, naphth.C-8a) | 27.9 (t, —CH₂—C$\underline{H}$₂—) | 125.8; 127; 129.9; |
| | 129.0 (s, Ar—C) | 132.7 (s, naphth.C-4a) | 40.5 (t, —NH—C$\underline{H}$₂—) | (d, 5 Ar—C) |

-continued

| | ¹³C—NMR [CDCl₃; δ (ppm)]: | | |
|---|---|---|---|
| | 134.0 (s, naphth.C-1) | 156.1 (s, —OC—NH—) | 143.7 (s, Ar—C) |
| C-Atom | 19 | 21 | 23 |
| C-1 | 27.9; t | 27.5; t | 30.9; t |
| C-5 | 34.3; t | 34.1; t | 34.1; t |
| CH₃—N— | 41.8; q | 41.8; q | 41.8; q |
| C-4a | 47.8; s | 47.9; s | 48.0; t |
| C-6 | 53.6; t | 53.6; t | 53.6; t |
| CH₃—O | 55.5; q | 55.0; q | 55.5; q |
| C-8 | 60.3; t | 60.3; t | 60.3; t |
| C-2 | 63.1; d | 71.2; d | 69.7; d |
| C-12a | 86.3; d | 86.1; d | 86.3; d |
| C-3 | 110.9; d | 110.9; d | 110.8; d |
| C-4 | 121.2; d | 120.8; d | 121.3; d |
| C-9 | 123.3; d | 121.5; d | 122.7; d |
| C-10 | 128.3; d | 128.7; d | 129.2; d |
| C-8a | 132.1; s | 130.0; s | 131.0; s |
| C-11b | 143.7; s | 131.3; s | 132.0; s |
| C-11a | 143.9; s | 137.7; s | 143.7; s |
| C-11 | 146.3; s | 143.7; s | 146.3; s |
| diverse C | 22.4 (q, —CH₃) | 100.8–128.7 (d, 5 Ar—C) | 13.6 (t, —CH₃) |
| | 50.6 (d, —NH—CH—CH₃) | 129.1 (s, Ar—C) | 19.9 (t, —CH₂—CH₁₃) |
| | 155.3 (s, —OOC—NH—) | 146.3 (s, OSC—NH—) | 27.8 (t, —CH₂—CH₂—CH₂—) |
| | | | 44.9 (t, —NH—CH₂—CH₂—) |
| | | | 189.1 (s, —OSC—NH—) |

| | | (+)-Galanthamine Carbamates and Thiocarbamates | | |
|---|---|---|---|---|
| Product | Empirical Formula | Name | | R |
| | C₂₄H₂₆N₂O₄ [406.48] | (+)-Galanthamin-phenylcarbamate | | |
| 18 | C₂₆H₂₉N₂O₄ [433.53] | (+)-Galanthamin-R-α-methylbenzylcarbamate | | |
| 20 | C₂₆H₂₉N₂O₄ [433.53] | (+)-Galanthamin-S-α-methylbenzylcarbamate | | |
| 22 | C₂₄H₂₆N₂O₃S [422.55] | (+)-Galanthamin-phenylthiocarbamate | | |
| 24 | C₂₂H₃₀N₂O₃S [402.56] | (+)-Galanthamin-n-butylthiocarbamate | | |

General Procedure

Sodium hydride (95%, 68 mg, 2.62 mmoles) was added under argon to a solution of 500 mg (1.74 mmoles) of (+)-galanthamine in 15 mL of absolute dimethylformamide and stirred for 30 minutes at room temperature. Subsequently, 1.2 equivalents of isocyanate or thioisocyanate were added dropwise and stirring was continued for a further 3 hours. The reaction mixture was poured into 150 mL of water and extracted twice with 150 mL of ethyl acetate. The organic phases were washed once with 150 mL of water, dried over sodium sulfate and evaporated. The residue was purified by column chromatography (acetone:methanol=9:1), colorless crystals being obtained.

TLC: Toluene: MeOH=4:1

| Product | Yield; [% d. Th.] | *$\alpha_D$ (25° C., c = 1) | Melting Point [° C.] |
|---|---|---|---|
|  | 84 | +51.9° | 77–80 |
| 18 | 42 | +55.6° | 53–60 |
| 20 | 47 | +56.5° | 55–57 |
|  | 56 | +43.5° | 195–198 |
|  | 91 | +42.0° | 52–55 |
| 22 | 61 | +10.4° | 75–78 |
| 24 | 73 | +31.2° | 122–125 |

General Procedure (−)-Galanthamine (800 mg, 2.78 mmoles), 1.2 equivalents of t-Boc-amino acid and 876.0 mg (3.34 mmoles) of triphenyl phosphine are added to 50 mL of absolute tetrahydrofuran. After the addition of 581.7 mg (3.34 mmoles) of diethyl azodicarboxylate (DEAD), the reaction mixture was stirred for 3 hours at room temperature. After the reaction, the solution was evaporated and the oily residue was purified by column chromatography, first in ethyl acetate, in order to separate the many by-products with a high $R_f$, and then in acetone. Upon drying in vacuum, the oily product expanded to a foam, from which it then hardened in air.

TLC: acetone: MeOH=9:1

| Product | Yield [% d. Th.] | $\alpha_D$ (25° C., c = 1) | melting point [° C.] |
|---|---|---|---|
| 25 | 93 | −187.3° | 65–66 |
| 26 | 50 | −146.6° | 53–56 |
| 28 | 53 | −140.0° | 63–67 |
| 29 | 78 | −181.7° | 117–119 |
| 31 | 62 | −140.6° | 126–130 |
| 32 | 44 | −159.1° | 67–69 |

(−)-N-tert.-Boc-Amino Acid Epigalanthamine Ester

| Product | Empirical Formula | Name | R |
|---|---|---|---|
| 25 | $C_{24}H_{32}N_2O_6$ [444.55] | (−)-N-t-Boc-Glycin-epigalanthaminester | —CH$_2$—NH—t-Boc |
| 26 | $C_{33}H_{40}N_2O_8$ [592.74] | (−)-N-t-Boc-L-Asparaginsäure-β-benzylester-epigalanthaminester | HN(t-Boc)—CH(—CH$_2$COOBn)— |
| 28 | $C_{33}H_{40}N_2O_8$ [592.74] | (−)-N-t-Boc-D-Asparaginsäure-β-benzylester-epigalanthaminester | HN(t-Boc)—CH(—CH$_2$COOBn)— |
| 29 | $C_{27}H_{38}N_2O_6S$ [518.65] | (−)-N-t-Boc-L-Methionin-epigalanthaminester | HN(t-Boc)—CH(—CH$_2$CH$_2$SCH$_3$)— |
| 31 | $C_{27}H_{38}N_2O_6S$ [518.65] | (−)-N-t-Boc-D-Methionin-epigalanthaminester | HN(t-Boc)—CH(—CH$_2$CH$_2$SCH$_3$)— |
| 32 | $C_{31}H_{38}N_2O_6$ [534.65] | (−)-N-t-Boc-L-Phenylalanin-epigalanthaminester | t-Boc-NH—CH(—CH$_2$C$_6$H$_5$)— |

| | ¹H—NMR [CDCl₃; δ (ppm)]: | | |
|---|---|---|---|
| Proton | 25 | 26 | 28 |
| H_a-5 | 1.65; m | 1.65; m | 1.60; m |
| H_a-1 | 1.85; m | 1.80; m | 1.70; m |
| H_b-5 | 2.18; m | 2.20; m | 2.15; m |
| CH₃—N— | 2.40; s | 2.35; s | 2.40; s |
| H_b-1 | 2.80; m | 2.80; m | 2.70; m |
| H_b-6 | 3.05; m | 3.10; m | 3.10; m |
| H_a-6 | 3.25; m | 3.25; m | 3.25; m |
| H_b-8 | 3.65; br.d | 3.65; br.d | 3.60; br.d |
| CH₃—O— | 3.80; s | 3.85; s | 3.85; s |
| H_a-8 | 4.05; br.d | 4.05; br.d | 4.05; br.d |
| H-12a | 4.55; t | 4.60; t | 4.55; t |
| H-2 | 3.90; d | 4.55; d | 4.50; d |
| H-3 | 5.70; d | 5.60; d | 5.70; d |
| H-4 | 6.15; d | 6.05; d | 6.10; d |
| H-9 | 6.55; d | 6.55; d | 6.55; d |
| H-10 | 6.65; d | 6.65; d | 6.65; d |
| diverse H | 1.45 (s, 9H, 3 × CH₃—) | 1.45 (s, 9H, 3 × CH₃—) | 1.45 (s, 9H, 3 × CH₃—) |
| | 1.80 (t, 2H, —OOC—CH₂—) | 2.90 (m, 1H, -OOC-CH-) | 2.90 (m, 1H, —OOC—CH—) |
| | 5.60 (s, 1H, —NH—COO—) | 3.0 (d, 2H, —CH₂—COOBn) | 3.0 (d, 2H, —CH₂—COOBn) |
| | | 5.10 (s, 2H, —OOC—CH₂Ph) | 5.15 (s, 2H, —OOC—CH₂—Ph) |
| | | 5.60 (s, 1H, —NH—COO—) | 5.60 (s, 1H, —NH—COO) |
| | | 7.30 (m, 5H, Ph-H) | 7.35 (m, 5H, Ph—H) |
| Proton | 29 | 31 | 32 |
| H_a-5 | 1.65; m | 1.65; m | 1.65; m |
| H_a-1 | 1.80; m | 1.80; m | 1.80; m |
| H_b-5 | 1.95; m | 1.95; m | 2.20; m |
| CH₃—N— | 2.10; s | 2.40; s | 2.40; s |
| H_b-1 | 2.85; m | 2.75; m | 2.80; m |
| H_b-6 | 3.05; m | 3.05; m | 3.00; m |
| H_a-6 | 3.25; m | 3.25; m | 3.25; m |
| H_b-8 | 3.65; br.d | 3.60; br.d | 3.60; br.d |
| CH₃—O— | 3.85; s | 3.85; s | 3.85; s |
| H_a-8 | 4.05; br.d | 4.05; br.d | 4.05; br.d |
| H-12a | 4.60; t | 4.60; t | 4.55; t |
| H-2 | 4.40; m | 4.40; m | 4.50; m |
| H-3 | 5.70, d | 5.70; t | 5.50; t |
| H-4 | 6.15; d | 6.15; d | 6.10; d |
| H-9 | 6.55; d | 6.55; d | 6.55; d |
| H-10 | 6.65; d | 6.65; d | 6.65; d |
| diverse H | 1.45 (s, 9H, 3 × CH₃—) | 1.40 (s, 9H, 3 × CH₃—) | 1.40 (s, 9H, 3 × CH₃—) |
| | 2.10 (s, 3H, CH₃—S—) | 2.10 (s, 3H, CH₃—S—) | 3.10 (m, 1H, —OOC—CH—) |
| | 2.20 (m, 2H, —CH₂—C_H₂—S—) | 2.15 (m, 2H, —CH₂—C_H₂—S—) | 5.60 (m, 2H, —CH₂—Ph) |
| | 2.55 (m, 2H, —C_H₂—CH₂—S—) | 2.50 (m, 2H, —C_H₂—CH₂—S—) | 5.10 (s, 1H, —NH—COO—) |
| | 2.60 (m, 1H, —OOC—C_H—CH₂—) | 2.60 (m, 1H, —OOC—C_H—CH₂—) | 6.10–6.30 (m, 5H, Ph—H) |
| | 5.15 (s, 1H, —NH—COO) | 5.15 (s, 1H, —NH—COO) | |

| | ¹³C—NMR [CDCl₃; δ (ppm)]: | | |
|---|---|---|---|
| C-Atom | 25 | 26 | 28 |
| C-1 | 28.1; t | 29.1; t | 28.9; t |
| C-5 | 33.9; t | 33.9; t | 34.1; t |
| CH₃—N— | 41.9; q | 41.8; q | 42.0; q |
| C-4a | 47.9; s | 47.9; s | 48.0; s |
| C-6 | 53.8; t | 53.8; t | 53.9; t |
| CH₃—O— | 55.8; q | 55.8; q | 55.9; q |
| C-8 | 60.2; t | 60.2; t | 60.3; t |
| C-2 | 67.4; d | 68.0; d | 68.0; d |
| C-12a | 87.4; d | 87.4; d | 87.5; d |
| C-3 | 111.1; d | 111.1; d | 111.2; d |
| C-4 | 121.5; d | 121.4; d | 121.5; d |
| C-9 | 126.6; d | 126.5; d | 126.6; d |
| C-10 | 127.4; d | 128.1; d | 128.3; d |
| C-8a | 128.9; s | 129.0; s | 129.1; d |
| C-11b | 132.3; s | 132.3; s | 132.4; s |
| C-11a | 143.7; s | 143.8; s | 143.8; s |
| C-11 | 146.5; s | 146.5; s | 146.6; s |

-continued

| | ¹³C—NMR [CDCl₃; δ (ppm)]: | | |
|---|---|---|---|
| diverse C | 28.1 (q, 3 × CH₃—) | 128.1 (q, 3 × CH₃—) | 28.2 (q, 3 × CH₃—) |
| | 42.4 (t, —OOC—CH₂—NH—) | 36.8 (t, —CH₃—) | 36.9 (t, —CH₂—) |
| | 79.7 (s, —O—C(CH₃)₃) | 50.0 (d, —CH—) | 50.1 (d, —CH—) |
| | 155.6 (s, —OOC—CH₂—NH—) | 66.6 (t, —O—CH₂—Ph) | 66.7 (t, —O—CH₂—Ph) |
| | 169.6 (s, —NH—COO—) | 79.9 (s, —O—C(CH₃)₃) | 80.0 (s, —O—C(CH₃)₃) |
| | | 128.2–128.4 (d, 4 Ar—C) | 128.3–128.5 (d, 5 Ar—C |
| | | 131.8 (d, Ar—C) | 135.4 (s, Ar—C) |
| | | 135.3 (s, Ar—C) | 155.2 (s, —OOC—CH—) |
| | | 155.1 (s, —OOC—CH—) | 170.2 (s, —NH—COO—) |
| | | 170.2 (s, —NH—COO—) | 170.5 (s, —COO—Bn) |
| | | 170.4 (s, —COOBn) | |

| C-Atom | 29 | 31 | 32 |
|---|---|---|---|
| C-1 | 28.1; t | 28.1; t | 28.1; t |
| C-5 | 33.9; t | 34.0; t | 33.9; t |
| CH₃—N— | 41.8; q | 41.9; q | 41.9; q |
| C-4a | 48.0; s | 48.0; s | 47.9; s |
| C-6 | 53.8; t | 53.8; t | 53.8; t |
| CH₃—O— | 55.8; q | 55.8; q | 55.8; q |
| C-8 | 60.2; t | 60.2; t | 60.2; t |
| C-2 | 67.4; d | 67.7; d | 67.5; d |
| C-12a | 87.4; d | 87.3; d | 87.4; d |
| C-3 | 111.1; d | 111.1; d | 111.1; d |
| C-4 | 121.5; d | 121.5; d | 121.4; d |
| C-9 | 126.4; d | 126.6; d | 126.4; d |
| C-10 | 128.4; d | 128.3; d | 128.2; d |
| C-8a | 129.0; s | 129.0; s | 131.7; s |
| C-11b | 132.3; s | 132.3; s | 132.7; s |
| C-11a | 143.8; s | 143.7; s | 143.8; s |
| C-11 | 146.5; s | 146.5; s | 146.5; s |
| diverse C | 15.4 (q, —S—CH₃) | 15.4 (q, —S—CH₃) | 28.1 (q, 3 × CH₃—) |
| | 28.1 (q, 3 × CH₃—) | 28.1 (q, 3 × CH₃—) | 38.4 (t, —CH₂—Ph) |
| | 29.6 (t, —CH₂—CH₂—S—) | 29.8 (t, —CH₂—CH₂—S—) | 54.5 (d, —CH—) |
| | 32.1 (t, —CH₂—CH₂—S—) | 32.1 (t, —CH₂—CH₂—S—) | 79.7 (s, —O—C(CH₃)₃) |
| | 52.8 (d, —CH—) | 52.8 (d, —CH—) | 126.8–131.8 (d, 5 Ar—C) |
| | 79.9 (s, —O—C(CH₃)₃) | 79.8 (s, —O—C(CH₃)₃) | 136.9 (s, Ar—C) |
| | 155.2 (s, —OOC—CH—) | 155.1 (s, —OOC—CH—) | 154.9 (s, —OOC—CH—) |
| | 171.5 (s, —OOC—NH—) | 171.5 (s, —OOC—NH—) | 171.7 (s, —OOC—NH—) |

| | | (+)-N-tert.-Boc-Amino Acid-Epigalanthamine Ester | | |
|---|---|---|---|---|
| Product | Empirical Formula | Name | | R |
| 27 | C₃₃H₄₀N₂O₈ [592.74] | (+)-N-t-Boc-L-Asparaginsäure-β-benzylester-epigalanthaminester | | t-Boc HN⟋⟍COOBn |
| 30 | C₂₇H₃₈N₂O₆S [518.65] | (+)-N-t-Boc-L-Methionin-epigalanthaminester | | t-Boc HN⟋⟍S—CH₃ |

General Procedure (+)-Galanthamine (800 mg, 2.78 mmoles), 1.2 equivalents of t-Boc-amino acid and 876.0 mg (3.34 mmoles) of triphenyl phosphine are added to 50 mL of absolute tetrahydrofuran. After the addition of 581.7 mg (3.34 mmoles) of diethyl azodicarboxylate (DEAD), the reaction mixture was stirred for 3 hours at room temperature. After the reaction, the solution was evaporated and the oily residue was purified by column chromatography, first in ethyl acetate, in order to separate the many by-products with a high $R_f$, and then in acetone. Upon drying in vacuum, the oily product expanded to a foam, from which it then hardened in air.

| Product | Yield [% d. Th.] | $\alpha_D$ (25° C., c = 1) | Melting Point [° C.] |
|---|---|---|---|
| 27 | 75 | +121° | 130–134 |
| 30 | 41 | +117° | 112–115 |

(+)-Bromogalanthamine-Phenyl Carbamate (33)

Crude bromogalanthamine (400 mg, 1.09 mmoles) was dissolved in 50 mL of absolute tetrahydrofuran, treated in an argon atmosphere with 390 mg (3.28 mmoles) of phenyl isocyanate and stirred for 24 hours under reflux. The reaction mixture was evaporated and the residue purified by column chromatography (EE: MeOH=3:2), 450 mg (85% of the theoretical yield) of colorless crystals being obtained.

TLC: EE: MeOH-3:2

$^1$H-NMR [CDCl$_3$; δ (ppm)]: 1.60(m, 1H, H$_a$-5); 2.10(m, 1H, H$_b$-5); 2.35(m, 1H, H$_a$-1); 2.40(s, 3H, N—CH$_3$); 2.70 (br. d, 1H, H$_b$-1); 3.0(m, 1H, H$_b$-6); 3.20(m, 1H, H$_a$-6); 3.80(s, 3H, CH$_3$O—); 3.95(dd, 1H, H-3); 4.30(br. d, 1H, H$_a$-8); 4.55(t, 1H, H-12a); 5.35(t, 1H, H-2); 5.95(dd, 1H, H-3); 6.30(d, 1H, H-4); 6.90(s, 1H, H-10); 7.0(s, 1H, —OOC—NH—); 7.0–7.30(m, 5H, Ar—H).

$^{13}$C-NMR [CDCl$_3$; δ (ppm)]: 27.7(t, C-1); 34.2(t, C-5); 42.0(s, N—CH$_3$); 48.5(s, C-4a); 53.4(t, C-6); 56.0(q, CH$_3$O—); 58.6(t, C-8); 63.6(d, C-2); 86.6(d, C-12a); 113.9 (s, C-9); 115.7(d, C-3); 118.7(d, C-4);123.2, 123.5(d, 2 Ar—C); 127.9(s, C-8a); 128.9(d, C-10); 130.3(s, 3 Ar-C); 133.3(s, C-11b); 138.0(s, Ar—C);144.0(s, C-11a); 146.1(s, C-11); 153.3(s, —OOC—NH—).

(±)-Bromogalanthamine-R-α-methylbenzyl Carbamate (34)

Crude bromogalanthamine (510 mg, 1.39 mmoles) was dissolved in 20 mL of absolute THF, treated in an argon atmosphere with 615 mg (4.18 mmoles) of R-(+)-α-methylbenzyl isocyanate and stirred for 2 days under reflux. The reaction mixture was evaporated and the residue purified by column chromatography (EF: MeOH=4:1), 600 mg (84% of the theoretical yield) of colorless crystals being obtained.

TLC: EE: MeOH—4:1

$^1$H-NMR [(CDCl$_3$); δ (ppm)]: 1.40(s, 3H, CH$_3$—); 1.55 (m, 1H, H$_a$-5); 2.0(m, 1H, H$_a$-1); 2.05(m, 1H, H$_b$-5); 2.35(s, 3H, N—CH$_3$); 2.65(m, 1H, H$_b$-1); 2.95(m, 1H, H$_b$-6); 3.25(m, 1H, H$_a$-6); 3.75(s, 3H, CH$_3$O—); 3.95(d, 1H, H$_b$-8); 4.25(d; 1H, H$_a$-8); 4.50(t, 1H, H-12a); 4.80(m, —NH—CH—) 5.20(s, 1H, —NH—CH—); 5.22(t, 1H, H-2); 5.88(dd, 1H, H-3); 6.20(d, 1H, H-4); 6.90(s, 1H, H-10); 7.30(m, 5H, Ar—H).

$^{13}$C-NMR [(CDCl$_3$); δ (ppm)]: 22.1(q, —CH—CH$_3$); 22.1(s, —CH—CH$_3$); 27.5(t, C-1); 33.7(t, C-5); 41.4(q, N—CH$_3$); 48.1(s, C-4a); 52.8(t, C-6); 55.6(q, CH$_3$O—); 58.0(t, C-8); 62.7(d, C-2); 86.2(d, C-12a); 113.4(s, C-9); 115.3(d, C-4); 123.6; 125.6; 126.8(d, 3 Ar—C); 127.3(s, Ar-C); 128.1; 129.3(d, 2 Ar—C); 132.9(s, C-8a); 143.0(s, C-11b); 143.7(s, C-11a); 145.7(s, C-11); 155.0(s, —OOC—NH—).

(±)-N-Pentyl-demethylbromogalanthamine (35)

In an argon atmosphere at room temperature, 430 mg (2.84 mmoles) of n-pentyl bromide is added dropwise to a solution of 100 mg (2.84 mmoles) of crude demethylbromogalanthamine in 30 mL of absolute THF. Subsequently, the reaction mixture was stirred under reflux for 2 days. The reaction mixture was evaporated, the oily residue taken up in 10 mL of water and adjusted with concentrated ammonium hydroxide to a pH of 10, a yellow precipitate being formed. The precipitate is filtered off with suction, washed with a little water and, after drying (became viscous in air), purified by column chromatography (chloroform: acetone= 85:15), 510 mg (43% of the theoretical yield) of a brown oil being obtained.

TLC: chloroform: acetone=85:15

$^1$H-NMR [CDCl$_3$; δ (ppm)]: 0.90(t, 3H, —CH$_3$); 1.30(m, 4H, —CH$_2$—CH$_2$—CH$_3$); 1.50(t, 2H, —N—CH$_2$—); 1.55 (m, 1H, H$_a$-5); 1.98(m, 1H, H$_a$-1); 2.15(m, H$_b$-5); 2.30(s, OH); 2.50(sext., 2H, —CH$_2$—CH$_2$—CH$_3$); 2.65(dd, 1H, H$_b$-1); 3.05(m, 1H, H$_b$-6); 3.28(m, 1H, H$_a$-6); 3.80(s, 3H, CH$_3$O—); 3.95(br. d, 1H, H$_b$-8); 4.10(t, 1H, H-2); 4.35(br. d, 1H, H$_a$-8); 4.55(t, 1H, H-12a); 6.0(dd, 1H, H-3); 6.10(d, 1H, H-4); 6.85(s, 1H, H-10).

$^{13}$C-NMR [CDCl$_3$; δ (ppm)]: 13.9(q, —CH$_3$); 22.4(t, —CH$_2$—CH$_2$—CH$_3$); 27.1(t,—CH$_2$—CH$_2$—CH$_3$); 29.4(t, N—CH$_2$—CH$_2$—); 29.7(t, C-1); 33.1(t, N—CH$_2$—CH$_2$—); 48.8(s, C-4a); 52.5(t, C-5); 52.3(t, C-6); 56.0(q, CH$_3$O—); 56.0(t, C-8); 61.7(d, C-2); 88.7(d, C-12a); 114.3(s, C-9); 115.7(d, C-3); 126.7(d; C-4); 127.8(d, C-10); 128.1(s, C-8a); 134.1(s, C-11b); 144.0(s, C-11a); 145.3(s, C-11).

O-TBDMS-N-Demethylbromogalanthamine (36)

A solution of 200 mg (0.57 mmoles) of 4.63 mg (0.63 mmoles) of triethylamine, 38 mg (0.57 mmoles) of imidazole, 157 mg (1.14 mmoles) of potassium carbonate and 171 mg (1.14 mmoles) of t-butyldimethychlorosilane in 15 mL absolute tetrahydrofuran is refluxed for 12 hours. Subsequently, the tetrahydrofuran is removed in a rotary evaporator and the residue purified by column chromatography (15 g of silica gel, solvent: chloroform: MeOH=95:5), 30 mg (12% of the theoretical yield) of an oily substance (36) being obtained.

TLC: chloroform: MeOH=9:1

$^1$H-NMR (CDCl$_3$; δ (ppm)): 0.09 (s, 9H, C(CH$_3$)$_3$); 0.85 (s, 6H, Si(CH$_3$)$_2$); 1.82 (dd, 1H, H-9); 1.96–2.14 (m, 2H, H-9'/5); 2.34 (ddd, 1H, H-5'); 3.31 (ddd, 1H, H-10); 3.51 (ddd, 1H, H-10'); 3.80 (s, 3H, OCH$_3$); 3.86 (d, 1H, H-12); 4.46 (b, 1H, H-6); 4.60 (b, 1H, H-4a); 4.22 (d, 1H, H-12'); 5.98 (dd, 1H, H-8); 6.01 (d, 1H, H-7); 6.88 (s, 1H, H-2)

O-TMS-Bromogalanthamine (37)

A solution of 800 mg (2.19 mmoles) of rac. bromogalanthamine (1), 260 mg mmoles) of trimethylsilyl chloride and 243 mg (2.40 mmoles) of triethylamine in 30.$_1$ absolute tetrahydrofuran is refluxed. After 2 hours, a further 130 mg (1.2 mmoles) of trimethylsilyl chloride are added dropwise and refluxed for one hour. Subsequently, the reaction mixture is evaporated, taken up in a little dichloromethane and purified over a filter column, bright yellow crystals of 37, melting at 228°–230° C., being obtained quantitatively.

TLC: chloroform: MeOH=9:1

$^1$H-NMR (CDCl$_3$; δ (ppm)): 0.10 (s, 9H, Si(CH$_3$)$_3$); 1.75 (broad d, 1H, H-9); 2.00–2.20 (m, 2H, H-9'/5); 2.35–2.50 (broad d, 1H, H-5'); 2.50 (s, 3H, NCH$_3$); 3.0–3.15 (m, 1H, H-10); 3.50 (ddd, 1H, H-10'); 3.85 (s, 3H, OCH$_3$); 4.20 (d, 1H, H-12, J$_{(12,12')}$=16.0 Hz); 4.25 (b, 1H, H-6); 4.50 (d, 1H-12', J$_{(12,12')}$=16.0 Hz); 4.60 (dd, 1H, H-4a); 5.90 (dd, 1H, H-8, J$_{(7,8)}$=9.8 Hz); 6.00 (dd, 1H, H-7, J$_{(7,8)}$=9.8 Hz); 6.90 (s, 1H, H-2)

(−)-O-TBDMS-Bromogalanthamine (38)

A solution of 2.0 g (5.46 mmoles) of (−)-bromogalanthamine (3), 1.23 g (8.20 mmoles) of t-butyldimethylchlorosilane and 0.61 g (6.00 mmoles) of triethylamine in 50 mL of tetrahydrofuran is heated for 4 hours at 50° C. Subsequently, the tetrahydrofuran is evaporated in a rotary evaporator, the residue taken up in a little dichloromethane and purified over a 1 cm silica gel column, 1.8 g (69% of the theoretical yield) of amorphous, viscous substance (38) with a rotation of an α$_D^{20}$[CHCl$_3$]=−66° being obtained.

TLC: chloroform: MeOH=9:1

¹H-NMR (CDCl₃; δ (ppm)): 0.05 (s, 6H, Si(CH₃)₂); 0.90 (s, 9H, SiC(CH₃)₃); 1.75–1.90 (m, 1H, H-9); 1.95–2.10 (m, 2H, H-5/9', $J_{(5,5')}$=16.9 Hz); 2.55 (s, 3H, NCH₃); 2.65 (dd, 1H, H-5', $J_{(5,5')}$=16.9 Hz); 3.00–3.15 (m, 1H, H-10, $J_{(10,10')}$=12.5 Hz); 3.45 (ddd, 1H, H-10', $J_{(10,10')}$=12.5 Hz); 3.85 (s, 3H, OCH₃); 4.15 (dd, 1H, H-6); 4.20 (d, 1H, H-12, $J_{(12,12')}$=16.0 Hz); 4.45 (d, 1H, H-12', $J_{(12,12')}$=16.0 Hz); 4.60 (b, 1H, H-4a); 5.59, 6.05 (AB, 2H, H-7/8, $J_{(7/8)}$=10.7 Hz); 6.95 (s, 1H, H-2)

O-TBDMS-Galanthamine (39)

A solution of 500 mg (1.36 mmoles) of galanthamine hydrobromide, 1.37 mg (1.36 mmoles) of triethylamine, 224 mg (1.36 mmoles) of potassium carbonate and 244 mg (1.63 mmoles) of t-butyldimethylchlorosilane in 20 mL of absolute tetrahydrofuran and 5 mL of absolute N,N-dimethylformamide is stirred for 4 hours at 60° C. Subsequently, the reaction mixture is evaporated and purified over a silica gel column, 320 mg (59% of the theoretical yield) of a yellow, oily substance (39), being obtained.

TLC: chloroform : MeOH=9:1

¹H-NMR (CDCl₃; δ (ppm)): 0.05, 0.10 (2* s, 6H, Si(CH₃)₂); 0.85,0.90 (2* s, 9H, SiC(CH₃)₃); 1.55 (ddd, 14, H-9, $J_{(9,9')}$=14.2 Hz); 2.00–2.20 (m, 2H, H-5/9', $J_{(9,9')}$=14.2 Hz); 2.25–2.45 (m, 1H, H-5'); 2.35 (s, 3H, NCH₃); 3.00 (ddd, 1H, H-10, $J_{(10,10')}$=11.6 Hz); 3.30 (ddd, 1H, H-10', $J_{(10,10')}$=11.6 Hz); 3.60 (d, 1H, H-12, $J_{(12,12')}$=14.2 Hz); 3.85 (s, 3H, OCH₃); 4.15 (d, 1H, H-12', $J_{(12,12')}$=14.2 Hz); 4.25 (dd, 1H, H-6); 4.55 (dd, 1H, H-4a); 5.85 (dd, 1H, H-8, $J_{(7,8)}$=9.8 Hz); 6.10 (d, 1H, H-7, $J_{(7,8)}$=9.8 Hz); 6.50, 6.60 (AB, 2H, H-1/2, $J_{(1,2)}$=8.0 Hz)

N-Allyl-N-demethyl-narwedine (41)

A solution of 100 mg (0.29 mmoles) of demethylbromonarwedine (15), 38 mg (0.31 mmoles) of allyl bromide, 46 mg (0.31 mmoles) of sodium iodide and 85 mg (0.62 mmoles) of potassium carbonate in 10 mL of absolute acetone is refluxed for 12 hours. Subsequently, the solution is evaporated, taken up in 2N hydrochloric acid, made alkaline with concentrated ammonia solution and extracted with chloroform. The combined organic phases are washed once with saturated aqueous sodium chloride solution, dried (sodium sulfate), filtered and evaporated, 50 mg of crude product being obtained, which is purified by column chromatography (15 g of silica gel, solvent: chloroform: MeOH= 9: 1), 28 mg (25% of the theoretical yield) of colorless crystals (41) being obtained.

TLC: chloroform: MeOH=9:1

¹H-NMR (CDCl₃; δ (ppm)): 1.80–2.25 (m, 3H, H-5/9/9'); 2.75 (ddd, 1H, H-5'); 3.05–3.25 (m, 2H, H-10/10'); 3.78 (s, 2H, NCH₂); 3.84 (s, 3H, OCH₃); 4.00 (d, 1H, H-12); 4.55 (d, 1H, H-12'); 4.73 (b, 1H, H-4a); 5.18 (dd, 2H, =CH₂); 5.90 (dd, 1H, =CH); 6.04 (d, 1H, H-8); 6.90 (s, 1H, H-2); 7.03 (d, 1H, H-7)

(6R)-4a,5,9,10,11,12-Hexahydro-1-bromo-3-methoxy-1-(phenylmethyl)-6H-benzofuro-[3a,3,2-ef][2]benzazepin-6-one (44)

A solution of 500 mg (1.43 mmoles) of demethylbromonarwedine (15), 244 mg (1.43 mmoles) of benzyl bromide, 214 mg (1.43 mmoles) of sodium iodide and 400 mg (2.90 mmoles) of potassium carbonate in 40 mL of absolute acetone is refluxed for 4 hours. Subsequently, the solution is evaporated, taken up in 2N hydrochloric acid, made, alkaline with concentrated ammonia and extracted with trichloromethane. The combined organic phases are washed once with saturated, aqueous sodium chloride solution, dried (sodium sulfate), filtered and evaporated, 350 mg of crude product being obtained, which is purified by column chromatography (15 g of silica gel, solvent: EtOAc: PE=1:1), 280 mg (45% of the theoretical yield) colorless crystals of 44, with a melting point of 135°–138° C., being obtained.

TLC: chloroform : MeOH=9:1

¹H-NMR (CDCl₃; δ (ppm)): 1.88 (dd, 1H, H-9); 2.15 (ddd, 1H, H-9'); 2.55–2.80 (m, 2H, H-5/5'); 2.98–3.38 (m, 2H, H-10/10'); 3.77 (s, 2H, NCH₂); 3.86 (s, 3H, OCH₃); 4.03 (d, 1H, H-12); 4.31 (d, 1H, H-12'); 4.74 (b, 1H, H-4a); 6.04 (d, 1H, H-8); 6.93 (s, 1H, H-2); 7.08 (d, 1H, H-7), 7.21–7.46 (m, 5H, Ph)

¹³C-NMR (CDCl₃; δ (ppm)): 31.6 (t, C-5); 37.0 (t, C-9); 49.4 (d, C-8a); 51.1 (t, C-10); 54.8 (t, NCH₂); 56.1 (q, OCH₃); 56.8 (t, C-12); 88.1 (d, C-4a); 114.1 (d; C-1); 116.4 (d, C-8); 127.1, 127.3 (2 d, C-7, Ph-4); 128.3 (d, Ph-1/2/6); 128.7 (2 d, Ph-315); 131.7 (s, C-12a); 138.1 (s, C-12b); 143.9 (s, C-3a); 144.6 (d, C-2); 146.6 (s, C-3); 193.3 (s, C-6)

(6R)-4a,5,9,10,11,12-Hexahydro-11-acetyl-1-bromo-3-methoxy-6H-benzofuro-[3a,3,2-ef][2]benzazepin-6-ol acetate (48)

A solution of 300 mg (0.85 mmoles) of 4, 258 mg (2.55 mmoles) of triethylamine in 15 mL of absolute acetone is reacted slowly at 0° C. with 200 mg (2.55 mmoles) of acetyl chloride and subsequently refluxed for 24 hours. The solution is evaporated to dryness, taken up in 2N hydrochloric acid and shaken 3 times with 30 mL of ethyl acetate. The combined organic phases are washed once with saturated aqueous sodium chloride solution, dried (sodium sulfate), filtered and evaporated to dryness. The crude product, which is contaminated with 59, is obtained by MPLC (60 g silica gel, solvent: chloroform: MeOH=1:1), 190 mg (51% of the theoretical yield) of an oily substance (48) being obtained.

TLC: chloroform: MeOH=9:1

¹H-NMR (CDCl₃; δ (ppm)): 1.70 (ddd, 1H, H-9); 1.80 (dd, 1H, H-9'); 1.95 (ddd, 1H, H-5); 2.03, 2.12 (2s, 6H, 2 COCH₃); 2.02–2.18 (m, 1H, H-5'); 2.68 (ddd, 1H, H-10, $J_{(10,10')}$=14.3 Hz); 3.20 (ddd, 1H, H-10', $J_{(10,10')}$=14.3 Hz); 3.85 (s, 3H, OCH₃); 4.33 (d, 1H, H-12, $J_{(12,12')}$=16.9 Hz); 4.55 (b, 1H, H-6, $J_{(6,8)}$=4.8 Hz); 5.14 (d, 1H, H-12', $J_{(12,12')}$=16.9 Hz); 5.32 (dd, 1H, H-4a, $J_{(4a,5)}$=$J_{(4a,5')}$=5.2 Hz); 5.93 (dd, 1H, H-8, $J_{(7,8)}$=10.3 Hz, $J_{(6,8)}$=4.8 Hz); 6.15 (d, 1H, H-7, $J_{(7,8)}$=10.3 Hz); 6.92 (s, 1H, H-2)

Alkylation of N-demethylbromogalanthamine (4): ($R_7$, =/, Z=N)

| Substance No. | group $R_6$ | Name | empirical formula MG |
|---|---|---|---|
| 49 |  | (6R)-4a,5,9,10,11,12-Hexahydro-1-brom-3-methoxy-11-hexyl-6H-benzofuro[3a,3,2-ef][2]-benzazepin-6-ol | $C_{22}H_{30}BrNO_3$ [436.40] |
| 52 |  | (6R)-4a,5,9,10,11,12-Hexahydro-1-brom-3-methoxy-11-(cyanomethyl)-6H-benzofuro-[3a,3,2-ef][2]benzazepin-6-ol | $C_{18}H_{19}BrN_2O_3$ [391.27] |
| 51 |  | (6R)-4a,5,9,10,11,12-Hexahydro-1-brom-6-hydroxy-3-methoxy-6H-benzofuro[3a,3,2-ef][2]-benzazepin-11-essigsäure-ethylester | $C_{20}H_{24}BrNO_5$ [438.33] |
| 53 |  | (6R)-4a,5,9,10,11,12-Hexahydro-1-brom-6-hydroxy-3-methoxy-6H-benzofuro[3a,3,2-ef][2]-benzazepin-11-essigsaureamid | $C_{18}H_{21}BrN_2O_4$ [409.29] |
| 55 | 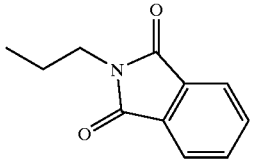 | (6R)-4a,5,9,10,11,12-Hexahydro-1-brom-3-methoxy-11-[2-(1H-isoindol-1,3(2H)-dion-2-yl)-ethyl]-6H-benzofuro[3a,3,2-ef][2]benzazepin-6-ol | $C_{26}H_{25}BrN_2O_5$ [525.41] |
| 50 |  | (6R)-4a,5,9,10,11,12-Hexahydro-1-brom-3-methoxy-11-(2-propinyl)-6H-benzofuro[3a,3,2-ef][2]benzazepin-6-ol | $C_{19}H_{20}BrNO_3$ [390.28] |
| 54 | 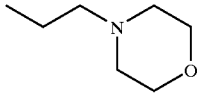 | (6R)-4a,5,9,10,11,12-Hexahydro-1-brom-3-methoxy-11-(2-morpholinoethyl)-6H-benzofuro[3a,3,2-ef][2]benzazepin-6-ol | $C_{22}H_{29}BrNO_3$ [465.39] |
| 56 | 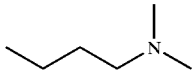 | (6R)-4a,5,9,10,11,12-Hexahydro-1-brom-3-methoxy-11-(3-dimethylaminopropyl)-6H-benzofuro[3a,3,2-ef][2]benzazepin-6-ol | $C_{21}H_{29}BrN_2O_3$ [437.39] |
| 58 | 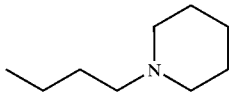 | (6R)-4a,5,9,10,11,12-Hexahydro-1-brom-3-methoxy-11-(3-piperidinopropyl)-6H-benzofuro[3a,3,2-ef][2]benzazepin-6-ol | $C_{24}H_{33}BrN_2O_5$ [477.45] |
| 57 | 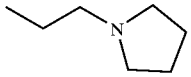 | (6R)-4a,5,9,10,11,12-Hexahydro-1-brom-3-methoxy-11-(2-pyrrolidinoethyl)-6H-benzofuro[3a,3,2-ef][2]-benzazepin-6-ol | $C_{22}H_{29}BrN_2O_3$ [449.40] |
| 42 |  | (6R)-4a,5,9,10,11,12-Hexahydro-1-brom-3-methoxy-11-(2-propen-yl)-6H-benzofuro[3a,3,2-ef][2]-benzazepin-6-ol | $C_{19}H_{22}BrNO_3$ [392.30] |
| 45 | 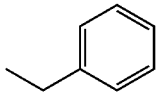 | (6R)-4a,5,9,10,11,12-Hexahydro-1-brom-3-methoxy-11-(phenyl-methyl)-6H-benzofuro[3a,3,2-ef][2]benzazepin-6-ol | $C_{23}H_{24}BrNO_3$ [442.36] |

Method: A mixture of 500 mg (1.42 mmoles) of N-demethylbromogalanthamine (4), 391 mg (2.84 mmoles) of potassium carbonate and 272 mg (1.70 mmoles) of potassium iodide are ground in a mortar and triturated. Subsequently, the mixture in 20 mL of absolute acetone is mixed with 1.2 equivalents of a halide reagent and refluxed. After the reaction is completed (TLC), the reaction mixture is evaporated and the residue taken up in 100 mL of 2N hydrochloric acid, washed with ethyl acetate, made alkaline with concentrated aqueous ammonia and either the precipitate is filtered off with suction or the solution is extracted three times with 30 mL of ethyl acetate. The precipitate is dried at 50° C./50 mbar, the combined organic phases are washed once with saturated, aqueous sodium chloride solution, dried (sodium sulfate, activated charcoal), filtered and evaporated. The product is purified further by column chromatography (15 g of silica gel; solvent: chloroform=≦chloroform: MeOH=9:1).

TLC: chloroform: MeOH=9:1

| Substance No. | Reagents | Reaction Time | Yield | Melting Point |
|---|---|---|---|---|
| 49 | 1-Bromhexane | 24 h | 67% oily substance | — |
| 52 | Chloroacetonitrile | 2 h | 89% colorless crystals | 150–153° C. |
| 51 | Ethyl chloroacetate | 1 h | quant. oily substance | — |

-continued

| Substance No. | Reagents | Reaction Time | Yield | Melting Point |
|---|---|---|---|---|
| 53 | Chloroacetamide | 1 h | 90% colorless crystals | 164–165° C. |
| 55 | N-(2-Bromethyl)-phthalimide | 48 h | quant. yellow crystals | 88–89° C. |
| 50 | Propargylbromide | 4 h | 57% oily substance | — |
| 54 | N-(2-Chlorethyl)-morpholin * HCl | 24 h | 98% oily substance | — |
| 56 | (3-Chlorpropyl)-dimethylamin * HCl | 72 h | 46% oily substance | — |
| 58 | N-(3-Chlorpropyl)-piperidin * HCl | 30 h | 85% oily substance | — |
| 57 | N-(2-Chlorethyl)-pyrrolidin * HCl | 24 h | 25% oily substance | — |
| 42 | Allylbromid | | 80% | |
| 45 | Benzylbromid | | 92% | |

| | $^1$H-NMR(CDCl$_3$ [*in DMSO-d$_6$]; δ(ppm)): | | | | |
|---|---|---|---|---|---|
| H-Atom | 49 | 52 | 51 | 53 | 55 |
| H-9 | 1.55(d) | 1.75(ddd) | 1.60(ddd) | 1.65(ddd) | 1.40(dd) |
| H-9' | 2.05(ddd | 2.05(ddd) | 1.90–2.05 | 1.90–2.10 | 1.90–2.30 |
| H-5 | 2.00(dd) | 2.55–2.75 | 1.90–2.05 | 1.90–2.10 | 1.90–2.30 |
| H-5' | 2.65(dd) | 2.55–2.75 | 2.20–2.30 | 2.70(dd) | 2.65(dd) |
| H-10 | 3.05(dd) | 3.10(ddd) | 2.65(dd) | 3.10(ddd) | 2.95(dd) |
| H-10' | 3.30(ddd) | 3.25(ddd) | 3.15(dd) | 3.40(ddd) | 3.25(dd) |
| NCH$_2$ | 2.50(dd) | 3.65(s) | 3.40(s) | 3.20(d) | 1.90–2.30 |
| OCH$_3$ | 3.85(s) | 3.85(s) | 3.80(s) | 3.85(s) | 3.75(s) |
| H-12 | 3.95(d) | 4.00(d) | 4.12(d) | 4.00(d) | 3.60(d) |
| H-12' | 4.40(d) | 4.30(d) | 4.45(d) | 4.40(d) | 4.35(d) |
| H-6 | 4.15(dd) | 4.15(b) | 4.16(s) | 4.15(b) | 4.05(b) |
| H-4a | 4.60(b) | 4.60(b) | 4.60(b) | 4.60(b) | 4.50(b) |
| H-8 | 6.00, 6.10(AB) | 6.05(b) | 6.00(dd) | 6.05(s) | 6.10(d) |
| H-7 | 6.00, 6.10(AB) | 6.05(b) | 6.10(dd) | 6.05(s) | 5.75(dd) |
| H-2 | 6.90(s) | 6.90(s) | 6.90(s) | 6.90(s) | 7.00(s) |
| additional H | 0.90(t, 3H, ω-CH$_3$); 1.20–1.35(m 6H γ/δ/ε-CH$_2$); 1.45–1.60(m, 2H, β-CH$_2$) | — | 1.30(t, 3H, OCH$_2$C$\underline{H}_3$); 4.20 (a. 2H. OC$\underline{H}_2$CH$_3$) | 5.70, 6.95(2* b, 2* 1H replace D$_2$O, NH$_2$) | 1.90–2.30(m, 6H, H-5/9'/ NCH$_2$—CH$_2$); 7.80–7.90(m, 4H, Ph) |
| J$_{(A,B)}$ (Hz) | 12, 12') = 16.9 | (9, 9') = 14.0 (10, 10') = 13.6 (12, 12') = 15.8 | (7, 8) = 10.3 (9, 9') = 13.4 (12, 12') = 16.1 | (5, 5') = 16.2 (9, 9') = 16.9 (10, 10') = 11.6 (12, 12') = 16.0 | (6, 8) = 4.5 (7, 8) = 9.8 |

| H-Atom | 50 | 54 | 56 | 58 | 57 |
|---|---|---|---|---|---|
| H-9 | 1.70(ddd) | 1.48–1.63 | 1.55(ddd) | 1.45(d) | 1.55(ddd) |
| H-9' | 1.95–2.01 | 1.92–2.13 | 2.00(ddd) | 1.95(dd) | 1.80–2.10 |
| H-5 | 1.95–2.01 | 1.92–2.13 | 1.65–1.85 | 1.95(dd) | 1.80–2.10 |
| H-5' | 2.63(dd) | 2.45–2.95 | 2.65(dd) | 2.58(dd) | 2.60–2.85 |
| H-10 | 3.10–3.35 | 3.12(ddd) | 3.10(dd) | 3.00(ddd) | 3.15(ddd) |
| H-10' | 3.10–3.35 | 3.35(ddd) | 3.30(dd) | 3.20(ddd) | 3.35(ddd) |
| NCH$_2$ | 3.48(d) | 2.45–2.95 | 2.50(dt) | 2.45(t) | 2.60–2.85 |
| OCH$_3$ | 3.33(s) | 3.82(s) | 3.85(s) | 3.80(s) | 3.30(s) |
| H-12 | 3.98(d) | 4.01(d) | 3.95(d) | 3.95(d) | 4.00(d) |
| H-12' | 4.36(d) | 4.39(d) | 4.45(d) | 4.35(d) | 4.40(d) |
| H-6 | 4.18(b) | 4.12(dd) | 4.15(b) | 4.13(b) | 4.13(dd) |
| H-4a | 4.59(b) | 4.59(b) | 4.60(b) | 4.58(b) | 4.60(b) |
| H-8 | 6.02(dd) | 6.02(dd) | 6.10(d) | 6.08(d) | 6.00, 6.08(AB) |

-continued

| | | | | | |
|---|---|---|---|---|---|
| H-7 | 6.08(dd) | 6.09(d) | 6.00(dd) | 5.98(dd) | 6.00, 6.08(AB) |
| H-2 | 6.92(s) | 6.90(s) | 6.85(s) | 6.90(s) | 6.90(s) |
| additional H | 2.29(t, 1H, ≡CH, $J_{(\equiv CH, NCH_2)}$ = 2.4 Hz) | 2.45–2.95(m, 9H, H-5'/NC$\underline{H}_2$C$\underline{H}_2$/morph-2/6); 3.72 (t, 4H, morph-3/5, $J_{(mo3/5, mo2/6)}$ = 4.8 Hz | 1.65–1.85(m, 3H, H-5, N-CH$_2$—CH$_2$); 2.18, 2.22(2* s, 6H, N(CH$_3$)$_2$); 2.30 (t, 2H, CH$_2$—NMe$_2$) | 1.35(ddd, 2H, Pip-4); 1.55 (ddd, 4H, Pip-3/5); 1.68(ddd, 2H, N—CH$_2$—C$\underline{H}_2$); 2.28(dd, 2H, C$\underline{H}_2$—N$_{Pip}$); 2.32(dd, 2H,). | 1.80–2.10(m, 6H, H-5/9$^2$/Pyr-3/4); 2.60–2.85(m, 9H, H-5'/NC$\underline{H}_2$C$\underline{H}_2$/Pyr-2/5) |
| $J_{(A,B)}$ (Hz) | (≡CH, NCH$_2$) = 2.4 (6, 8) = 4.5 (6, 7) = 1.3 (7, 8) = 10.0 (9, 9') = 13.4 (12, 12') = 15.4 | (mo3/5, mo2/6) = 4.8 (10, 10') = 13.4 (12, 12') = 16.1 | (12, 12') = 16.0 | (NC$\underline{H}_2$C$\underline{H}_2$) = 7.3 (5, 5') = 10.6 (6, 8) = 4.6 (7, 8) = 10.4 (10, 10') = 14.3 (12, 12') = 16.0 | (9, 9') = 13.4 (10, 10') = 12.5 (12, 12') = 16.0 |

| H-atom | 42 | 45 | | | |
|---|---|---|---|---|---|
| H-9 | 1.58(ddd) | 1.55(ddd) | | | |
| H-9' | 1.90–2.10 | 2.01(ddd) | | | |
| H-5 | 1.90–2.10 | 2.60–2.73 | | | |
| H-5' | 2.15–2.25 | 2.60–2.73 | | | |
| H-10 | 2.65(ddd) | 3.50(ddd) | | | |
| H-10' | 3.02–3.29 | 3.27(ddd) | | | |
| NCH$_2$ | 3.18(d) | 3.70(s) | | | |
| OCH$_3$ | 3.82(s) | 3.82(s) | | | |
| H-12 | 3.92(d) | 4.00(d) | | | |
| H-12' | 4.35(d) | 4.34(d) | | | |
| H-6 | 4.11(b) | 4.14(b) | | | |
| H-4a | 4.59(b) | 4.64(b) | | | |
| H-8 | 6.00(dd) | 6.02(ddd) | | | |
| H-7 | 6.09(d) | 6.14(dd) | | | |
| H-2 | 6.90(s) | 6.90(s) | | | |
| additional H | 5.16(dd, 2H, =CH$_2$); 5.88 (ddt, 1H, =CH) | 7.22–7.35(m, 5H, Ph) | | | |
| $J_{(A,B)}$ (Hz) | (NCH$_2$, =CH) = 7.0 (9, 9') = 14.0 (12, 12') = 16.5 | (6, 8) = 4.8 (7, 8) = 10.3 (9, 9') = 13.2 (10, 10') = 13.0 (12, 12') = 15.9 | | | |

| $^{13}$C-NMR(CDCl$_3$ [*in DMSO-d$_6$]; δ(ppm)): | | | | | |
|---|---|---|---|---|---|
| C-Atom | 49 | 52 | 51 | 53 | 54 |
| C-5 | 29.7(t) | 29.2(t) | 29.3(t) | 29.4(t) | (t) |
| C-9 | 33.1(t) | 34.5(t) | 33.6(t) | 33.9(t) | (t) |
| C-8a | 48.8(s) | 48.3(s) | 43.4(s) | 43.3(s) | (s) |
| C-10 | 51.5(t) | 51.6(t) | 51.2(t) | 51.8(t) | (t) |
| NCH$_2$ | 52.5(t) | 53.7(t) | 53.4(t) | 56.3(t) | (t) |
| OCH$_3$ | 55.9(q) | 56.1(q) | 55.7(q) | 55.8(q) | (q) |
| C-12 | 56.0(t) | 57.2(t) | 56.3(t) | 56.9(t) | (t) |
| C-6 | 61.7(d) | 61.6(d) | 61.3(d) | 61.3(d) | (d) |
| C-4a | 88.6(d) | 88.6(d) | 88.3(d) | 88.3(d) | (d) |
| C-1 | 114.3(s) | 113.9(s) | 113.9(s) | 114.2(s) | (s) |
| C-8 | 115.7(d) | 115.8(d) | 115.4(d) | 115.5(d) | (d) |
| C-2 | 126.7(d) | 126.3(d) | 126.2(d) | 125.6(d) | (d) |
| C-7 | 127.8(d) | 128.5(d) | 127.8(d) | 128.4(d) | (d) |
| C-12a | 128.1(s) | 130.2(s) | 127.3(s) | 126.5(s) | (s) |
| C-12b | 134.1(s) | 134.0(s) | 133.7(s) | 133.7(s) | (s) |
| C-3a | 144.0(s) | 144.5(s) | 143.9(s) | 144.2(s) | (s) |
| C-3 | 145.3(s) | 145.6(s) | 145.2(s) | 145.2(s) | (s) |
| additional C | 13.9(q, ω-CH$_3$); 22.5(t, ε-CH$_2$); 26.9, 27.4(2* t, γ/δ-CH$_2$); 31.6(t, β-CH$_2$) | 115.5(s, CN) | 13.3(q, OCH$_2$C$\underline{H}_3$); 60.3(t, OC$\underline{H}_2$CH$_3$); OCH$_2$CH$_3$); 170.3(s,CO) | 173(s, CO) | |

| C-Atom | 56 | 58 | 57 | | |
|---|---|---|---|---|---|
| C-5 | 29.4(t) | 29.4(t) | 29.6(t) | (t) | (t) |
| C-9 | 32.8(t) | 32.8(t) | 33.2(t) | (t) | (t) |
| C-8a | 48.6(s) | 48.5(s) | 48.9(s) | (s) | (s) |
| C-10 | 51.5(t) | 51.1(t) | 52.5(t) | (t) | (t) |
| NCH$_2$ | 55.6(t) | 55.8(t) | 54.7(t) | (t) | (t) |

-continued

| | | | | |
|---|---|---|---|---|
| OCH₃ | 55.7(q) | 55.7(q) | 56.0(q) | (q) | (q) |
| C-12 | 57.3(t) | 56.8(t) | 55.6(t) | (t) | (t) |
| C-6 | 61.4(d) | 61.4(d) | 61.7(d) | (d) | (d) |
| C-4a | 88.3(d) | 88.3(d) | 88.7(d) | (d) | (d) |
| C-1 | 114.0(s) | 113.9(s) | 114.3(s) | (s) | (s) |
| C-8 | 115.4(d) | 115.4(d) | 115.7(d) | (d) | (d) |
| C-2 | 126.6(d) | 126.4(d) | 126.3(d) | (d) | (d) |
| C-7 | 127.6(d) | 127.6(d) | 128.1(d) | (d) | (d) |
| C-12a | 127.7(s) | 127.8(s) | 127.6(s) | (s) | (s) |
| C-12b | 133.8(s) | 133.8(s) | 134.1(s) | (s) | (s) |
| C-3a | 143.8(s) | 143.7(s) | 144.3(s) | (s) | (s) |
| C-3 | 145.1(s) | 145.1(s) | 145.5(s) | (s) | (s) |
| additional C | 25.3(t, N—CH₂CH₂); 45.0(q, N(CH₃)₂); 53.4(t, CH₂—NMe₂) | 23.9, 24.2(2* t, NCH₂CH₂, Pip-4); 25.3(t, Pip-3/5); 50.2 (t, CH₂—N$_{Pip}$); 54.1(t,) | 23.2(t, Pyr-3/4); 53.7(t, CH₂—N$_{Pyr}$); 54.4(t, Pyr-2/5) | | |

Acylation of N-Demethylbromogalanthamine (4)

($R_7$=/, Z=N)

| Substance No. | Group: $R_6$ | Name | Empirical formula, MG |
|---|---|---|---|
| 59 |  | (6R)-4a,5,9,10,11,12-Hexahydro-1-bromo-3-methoxy-11-acetyl-6H-benzofuro[3a,3,2-ef][2]benzazepin-6-ol | C₁₈H₂₀BrNO₄ [394.27] |
| 60 | 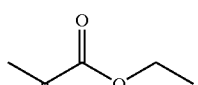 | Ethyl(6R)-4a,5,9,10,11,12-Hexahydro-1-bromo-6-hydroxy-3-methoxy-6H-benzofuro[3a,3,2-ef][2]benzazepin-11-α-oxo-acetate | C₂₀H₂₂BrNO₆ [452.31] |
| 62 |  | Methyl(6R)-4a,5,9,10,11,12-Hexahydro-1-bromo-6-hydroxy-3-methoxy-6H-benzofuro[3a,3,2-ef][2]benzazepin-11-carboxylate | C₁₈H₂₀BrNO₅ [410.27] |
| 61 |  | Methyl(6R)-4a,5,9,10,11,12-Hexahydro-1-bromo-6-hydroxy-3-methoxy-6H-benzofuro[3a,3,2-ef][2]benzazepin-11-γ-oxo-butyrate | C₂₁H₂₄BrNO₆ [466.34] |
| 64 |  | (6R)-4a,5,9,10,11,12-Hexahydro-1-bromo-3-methoxy-11-(1-oxohexadecyl)-6H-benzofuro-[3a,3,2-ef][2]benzazepin-6-ol | C₃₂H₄₈BrNO₄ [590.65] |

A solution of 500 mg (1.42 mmoles) of N-demethylbromogalanthamine, (4) and 156 mg (1.56 mmoles) of triethylamine in 20 mL of absolute acetone is treated with 0.9 equivalents of acid halide and refluxed. After the reaction is completed (TLC), the reaction mixture is evaporated, the residue taken up in 100 mL of 2N hydrochloric acid, washed with a little acetate, made alkaline with concentrated aqueous ammonia and either the precipitate is filtered off with suction or the solution extracted three times with 30 mL of ethyl acetate. The precipitate is dried at 50° C./50 mbar, the combined organic phases are washed with saturated, aqueous sodium chloride solution, dried (sodium sulfate, activated charcoal), filtered and evaporated. The product is purified further by column chromatography (7 g of silica gel; solvent: chloroform: MeOH=9:1)

TLC chloroform: MeOH=9:1

| Substance No. | Reagents | Reaction Time | Yield | Melting Point |
|---|---|---|---|---|
| 59 | Acetyl chloride | 3 h | 84% yellow crystals | 76–78° C. |

-continued

| Substance No. | Reagents | Reaction Time | Yield | Melting Point |
|---|---|---|---|---|
| 60 | Acid chloride of ethyl oxalate | 1.5 h | 54% yellow crystals | 66–69° C. |
| 62 | Metyl chloroformate | 1 h | 93% colorless crystals | 158–159° C. |
| 61 | Acid chloride of methyl succinate | 1.5 h | 35% colorless crystals | 53–57° C. |
| 64 | Palmityl chloride |  | 99% |  | drofuran is evaporated off in a rotary evaporator and the residue taken up in 50 mL of ethyl acetate. The organic phase is washed once with 2N hydrochloric acid, a saturated aqueous sodium hydrogen carbonate solution and a saturated, aqueous, sodium chloride solution, dried (sodium sulfate) and evaporated, colorless crystals of 63 being obtained quantitatively.

TLC: EtOAc: MeOH=4:1

$^1$H-NMR (CDCl$_3$; δ (ppm)): 1.45 (s, 9H, t-Bu); 1.80 (dd, 1H, H-9); 2.05 (dd, 1H, H-9'); 2.30 (ddd, 1H, H-5); 2.65

| | $^1$H-NMR(CDCl$_3$ [*in DMSO-d$_6$]; δ(ppm)): | | | | |
|---|---|---|---|---|---|
| H-Atom | 59 | 60 | 62* | 61 | 64 |
| H-9 | 1.79(ddd) | 1.92(ddd) | 1.60–1.90 | 1.75(ddd) | 1.74(ddd) |
| H-9' | 1.90(ddd) | 2.03(ddd) | 1.60–1.90 | 1.94(ddd) | 2.24(ddd) |
| H-5 | 1.97(dd) | 2.25(dd) | 2.05(dd) | 2.06(dd) | 1.95(dd) |
| H-5' | 2.05(dd) | 2.63(dd) | 2.40(dd) | 2.45–2.70 | 2.45(ddd) |
| H-10 | 2.67(ddd) | 3.38(ddd) | 3.40(dd) | 2.98(dd) | 2.68(ddd) |
| H-10' | 3.20(ddd) | 3.68(ddd) | 3.90(dd) | 3.22(ddd) | 3.20(ddd) |
| OCH$_3$ | 3.83(s) | 3.85(s) | 3.75(s) | 3.80(s) | 3.84(s) |
| H-12 | 4.33(d) | 4.25–4.45 | 4.20(d) | 4.33(d) | 4.31(d) |
| H-12' | 5.13(d) | 5.20(d, Conf$_A$), 5.75(d, Conf$_B$) | 5.20(d) | 5.22(d) | 5.18(d) |
| H-6 | 4.13(b) | 4.10(b) | 4.10(b) | 4.12(dd) | 4.13(dd) |
| H-4a | 4.60(b) | 4.45(b, Conf$_A$), 4.60(b, Conf$_B$) | 4.50(b) | 4.60(dd) | 4.60(b) |
| H-8 | 6.03(dd) | 5.90–6.15 | 5.85(dd) | 6.02(dd) | 6.05(dd) |
| H-7 | 5.90(d) | 5.90–6.15 | 6.00(dd) | 5.96(d) | 5.91(d) |
| H-2 | 6.94(s) | 6.90(s) | 6.85(s) | 6.90(s) | 6.90(s) |
| additional H | 2.11(s, 3H, OCH$_3$); 2.30(b, 1H simulates D$_2$O, OH) | 4.25–4.45(m, 3H, H-12Conf$_{A/B}$/COOCH$_2$); 1.10(t, 3H, OCH$_2$CH$_3$) | 3.55(s, 3H, COOCH$_3$) | 2.45–2.70(m, 5H, H-5/COCH$_2$CH$_2$); 3.65(s, 3H, COOCH$_3$) | 0.89(t, 3H, ω-CH$_3$); 1.18–1.40(m, 22H, CH$_2^{(4-14)}$); 1.45–1.67(m, 4H, CH$_2^{(2-3)}$); 2.18(t, 2H, COCH$_2$) |

| $^{13}$C-NMR(DMSO-d$_6$; δ(ppm)): |
|---|
| 59: 29.6(q, COCH$_3$); 30.3, 36.1(t, C-5$_{Conformer\ A/B}$); 37.9, 43.4(t, C-9$_{Conformer\ A/B}$); 46.5, 48.8(t, C-10$_{Conformer\ A/B}$); 48.4(s, C-8a); 51.4, 55.8(t, C-12$_{Conformer\ A/B}$); 55.9(q, OCH$_3$); 86.3, 86.5(d, C-4a$_{Conformer\ A/B}$); 115.4(d, C-8); 126.3, 126.4(d, C-2$_{Conformer\ A/B}$); 127.7(s, C-1); 128.5(s, C-12a); 128.7(d, C-7); 133.2, 133.4(s, C-12b$_{Conformer\ A/B}$); 144.0, 144.3(s, C-11a$_{Conformer\ A/B}$); 146.6, 147.0(s, C-3$_{Conformer\ A/B}$); 168.9, 169.2(s, CO$_{Conformer\ A/B}$) |
| 62: 30.2, 30.5(t, C-5$_{Conformer\ A/B}$); 36.5, 37.3(t, C-9$_{Conformer\ A/B}$); 44.7, 45.0(t, C-10$_{Conformer\ A/B}$); 48.4(s, C-8a); 49.7, 50.4(t, C-12$_{Conformer\ A/B}$); 52.2(q, COOCH$_3$); 55.7(q, OCH$_3$); 59.7(d, C-6); 86.8(d, C-4a); 111.8, 112.1(s, C-1$_{Conformer\ A/B}$); 115.2(d, C-8); 125.8, 126.0(d, C-2$_{Conformer\ A/B}$); 128.1, 128.3(s, C-12a$_{Conformer\ A/B}$); 128.5, 128.6(d, C-7$_{Conformer\ A/B}$); 133.1(s, C-12b); 143.9(s, C-3a); 146.4(s, C-3); 155.2(s, CO) |

60 rac.N-Boc-Bromogalanthamine (63)

To a solution of 1.0 g (2.84 mmoles) of rac. N-demethylbromogalanthamine (4) and 620 mg (2.84 mmoles) of di-t-butyl pyrocarbonate in 50 mL of absolute tetrahydrofuran, 286 mg (2.84 mmoles) of triethylamine are added dropwise and refluxed. After 15 minutes, the tetrahy- (ddd, 1H, H-5'); 3.30 (ddd, 1H, H-10); 3.85 (s, 3H, OCH$_3$); 4.05–4.30 (m, 2H, H-6/10'); 4.10 (d, 1H, H-12, J$_{(12,12')}$=15.1 Hz); 4.60 (dd, 1H, H-4a); 5.25 (d, 1H, H-12', J$_{(12,12')}$=15.1 Hz); 5.90 (d, 1H, H-8, J$_{(7,8)}$=8.9 Hz); 6.00 (dd, 1H, H-7, J$_{(7,8)}$=8.9 Hz); 6.90 (s, 1H, H-2)

Modification of N-Substituted Galanthamine Derivatives

| Substance No | Educt No. | $R_6$ Educt | $R_6$ Product | $R_1$ | Method |
|---|---|---|---|---|---|
| 66 | 61 | CH₂CH₂-C(=O)-CH₂CH₂-COOMe | CH₂CH₂-C(=O)-CH₂CH₂-COOH | Br | A |
| 67 | 60 | CH₂-C(=O)-COOEt | CH₂-C(=O)-COOH | Br | A |
| 71 | 51 | CH₂CH₂-COOEt | CH₂CH₂-COOH | Br | A |
| 68 | 51 | CH₂CH₂-COOEt | CH₂CH₂CH₂-OH | Br | B |
| 69 | 51 | CH₂CH₂-COOEt | CH₂CH₂CH₂-OH | H | C |
| 68 | 60 | CH₂-C(=O)-COOMe | CH₂CH₂CH₂-OH | Br | D |
| 70 | 55 | N-propyl phthalimide | CH₂CH₂CH₂-NH₂ | Br | E |
| 65 | 59 | CH₃-C(=O)-CH₃ | CH₂CH₂-Et (N-Et) | H | F |

Method A

An approximately 10% solution of the educt in 2N potassium hydroxide is refluxed. After 1 to 3 hours, the reaction is completed and the reaction solution is added dropwise to 2N hydrochloric acid and, in the case of amino acids, neutralized with concentrated aqueous ammonia. The aqueous phase is extracted subsequently three times with chloroform: ethanol 9:1. The organic phase is evaporated and the crude product optionally purified by column chromatography (15 g silica gel G60, solvent: MeOH/methylene chloride mixtures).

TLC: chloroform: MeOH=9:1

| Sub-stance No. | Name | SF, MG | Yield | Melting Point |
|---|---|---|---|---|
| 66 | (6R)-4a,5,9,10,11,12-Hexahydro-1-brom-6-hydroxy-3-methoxy-6H-benzofuro[3a,3,2-ef][2]-benzazepin-11-γ-oxo-butyric acid | $C_{20}H_{22}BrNO_6$ [452.31] | 89% yellow crystals | 107–109° C. |
| 67 | (6R)-4a,5,9,10,11,12-Hexahydro-1-brom-6-hydroxy-3-methoxy-6H-benzofuro[3a,3,2-ef][2]-benzazepin-11-α-oxo-acetic acid | $C_{18}H_{18}BrNO_6$ [424.26] | 22% red crystals | Decomposition >120° C. Decompo- |
| 71 | (6R)-4a,5,9,10,11,12-Hexahydro-1-brom-6-hydroxy-3-methoxy-6H-benzofuro[3a,3,2-ef][2]-benzazepin-11-acetic acid | $C_{18}H_{20}BrNO_5$ [410.27] | quant. colorless crystals | sition >200° C. |

Method B

An approximately 5% solution of the educt in absolute tetrahydrofuran is treated at 0° C. with two equivalents of a 10% solution of lithium aluminum hydride in tetrahydrofuran. After 1.5 hours, the reaction solution is hydrolyzed with a 1:1 solution of water in tetrahydrofuran, the tetrahydrofuran is evaporated off in a rotary evaporator and the residue dissolved in 2N hydrochloric acid. After the addition of 2.5 equivalents of tartaric acid, the solution is made alkaline with concentrated aqueous ammonia and extracted with ethyl acetate. The combined organic phases are washed once with a saturated, aqueous sodium chloride solution, dried (sodium sulfate), filtered and evaporated. The crude product is purified by column chromatography (15 silica gel G60, solvent: chloroform:MeOH=9:1).

TLC: chloroform: MeOH=9:1

| Substance No | Name | SF, MG | Yield | Melting Point |
|---|---|---|---|---|
| 68 | (6R)-4a,5,9,10,11,12-Hexahydro-1-brom-3-methoxy-11-(2-hydroxyethyl)-6H-benzofuro[3a,3,2-ef][2]-benzazepin-6-ol | $C_{18}H_{22}BrNO_4$ [396.29] | quantitative oily substance | — |

Method C

An approximately 5% solution of the theoretical yield educt in absolute tetrahydrofuran is treated at 0° C. with four equivalents of a 10% solution of lithium aluminum hydride in tetrahydrofuran. After 15 minutes, heat to reflux. After 24 hours, the reaction solution is hydrolyzed with a 1:1 solution of water in tetrahydrofuran, the tetrahydrofuran is evaporated off in a rotary evaporator, and the residue is dissolved in 2N hydrochloric acid. After adding five equivalents of tartaric acid, it is made basic with concentrated hydrous ammonia and extracted with ethyl acetate. The combined organic phases are washed once with saturated aqueous sodium chloride solution, dried ($Na_2SO_4$), filtered and evaporated. The crude product is cleaned by column chromatography (15 g silica gel G60, solvent: $CHCl_3$: MeOH=9:1).

DC: $CHCl_3$: MeOH=9:1

| Substance No. | Name | SF, MG | yield | Smp. |
|---|---|---|---|---|
| 69 | (6R-4a,5,9,10,11,12-Hexahydro-3-methoxy-11-(2-hydroxyethyl)-6H-benzofuro[3a,3,2-ef][2]-benzazepin-6-ol | $C_{18}H_{23}NO_4$ [317.39] | 81% oily Substance | — |

Method D 0.84 mL 10% lithium aluminum hydride solution (2.20 mmol) is heated in tetrahydrofuran to reflux. 100 mg (0.22 mmol) mt7 are then dissolved in absolute tetrahydrofuran and added dropwise to the boiling solution. After 15 minutes, the reaction mixture is cooled to 0° C. and hydrolyzed with water: tetrahydrofuran 1:1. Subsequently, the tetrahydrofuran is evaporated off in a rotary evaporator, the residue is absorbed in 50 mL 2 N hydrochloric acid, mixed with 0.80 g tartaric acid, made basic with concentrated aqueous ammonia and extracted three times with 30 mL ethyl acetate each. The combined organic phases are washed once with saturated aqueous sodium chloride solution, dried ($Na_2SO_4$), filtered and evaporated, whereby 100 mg crude product are obtained, which is cleaned by column chromatography (15 g silica gel, solvent: $CHCl_3$: MeOH=9:1).

DC: $CHCl_3$: MeOH=9:1

| Substance No. | Name | SF, MG | Yield | Melting Point |
|---|---|---|---|---|
| 68 | (6R)-4a,5,9,10,11,12-Hexahydro-1-brom-3-methoxy-11-(2-hydroxyethyl)-6H-benzofuro [3a,3,2-ef][2]benzazepin-6-ol | $C_{18}H_{22}BrNO_4$ [396.29] | 42% oily Substance | — |

Method E 170 mg (0.32 mmol) st80 and 80 mg (1.60 mmol) are heated to reflux in 10 mL absolute ethanol. After 30 minutes the reaction mixture is cooled and after 1 hour the resulting sediment is evaporated in a rotary evaporator. The sediment is washed once with ethanol and the ethanolic phase is subsequently spun in. The crude product is cleaned by column chromatography (15 g silica gel, solvent: $CHCl_3$: MeOH=9:1).

DC: $CHCl_3$:MeOH=9:1

| Substance No. | Name | SF, MG | Yield | Melt. pt. |
|---|---|---|---|---|
| 70 | (6R)-4a,5,9,10,11,12-Hexahydro-1-brom-3-methoxy-11-(2-aminoethyl)-6H-benzofuro-[3a,3,2-ef][2]benzazepin-6-ol | $CH_{18}H_{23}BrN_2O_3$ [395.30] | 70% colorless crystals | 116–117° C. |

Method F

To 2 mL 10% lithium aluminum hydride solution in tetrahydrofuran (5.26 mmol), 50 mg (0.381 mmol)st62 in 1.5 mL absolute tetrahydrofuran are added dropwise. Subsequently, the mixture is heated to reflux for 90 minutes. It is then hydrolyzed at 0° C. with water: tetrahydrofuran= 1:1 and the mixture is spun to dry. The residue is then absorbed in 2 N hydrochloric acid, mixed with 1.2 g tartaric acid and made basic with concentrated aqueous ammonia. Following that, it is extracted three times with 40 mL ethyl acetate each, the combined organic phases are washed once with saturated aqueous sodium chloride solution, dried ($Na_2SO_4$), filtered and evaporated. The crude product is cleaned by column chromatography (15 g silica gel, solvent: $CHCl_3$: MeOH=9:1).

DC: $CHCl_3$: MeOH=9:1

| Substance No. | Name | SF, MG | Yield | Melt. pt. |
|---|---|---|---|---|
| 65 | (6R)-4a,5,9,10,11,12-Hexahydro-1-brom-3- | $C_{18}H_{22}NO_3$ [300.38] | 76% oily substance | — |

| Substance No. | Name | SF, MG | Yield | Melt. pt. |
|---|---|---|---|---|
| | methoxy-11-ethyl-6H-benzofuro[3a,3,2-ef][2]-benzazepin-6-ol | | | |

$^1$H-NMR(CDCl$_3$ [*in DMSO-d$_6$]; δ(ppm)):

| H-Atom | 66 | 67 | 71 | 68 | 69 |
|---|---|---|---|---|---|
| H-9 | 1.70–2.10 | 1.85–2.35 | 1.80–2.10 | 1.60(ddd) | 1.60(ddd) |
| H-9' | 1.70–2.10 | 1.85–2.35 | 1.80–2.10 | 1.90–2.10 | 1.90–2.10 |
| H-5 | 2.40–2.80 | 1.85–2.35 | 2.25(dd) | 1.90–2.10 | 1.90–2.10 |
| H-5' | 2.90(ddd) | 3.30–3.70 | 3.00(ddd) | 2.60–2.75 | 2.60–2.75 |
| H-10 | 3.25(ddd) | 3.30–3.70 | 3.20–3.50 | 3.10(ddd) | 3.15(ddd) |
| H-10' | 3.40(d), 3.60(dd) | 3.30–3.70 | 3.20–3.50 | 3.45(ddd) | 3.40(ddd) |
| NCH$_2$ | — | — | 3.15(s) | 2.60–2.75 | 2.60–2.75 |
| OCH$_3$ | 3.80(s) | 3.80(s) | 3.75(s) | 3.80(s) | 3.82(s) |
| H-12 | 4.35(d) | 3.30–3.70 | 3.60(d) | 4.00(d) | 3.78(d) |
| H-12' | 5.20(d) | 4.10(d) | 4.20(d) | 4.40(d) | 4.17(d) |
| H-6 | 4.15(b) | 4.60(b) | 4.08(b) | 4.12(dd) | 4.12(dd) |
| H-4a | 4.60(b) | 4.90(b) | 4.50(b) | 4.60(b) | 4.60(b) |
| H-8 | 5.90(d) | 6.15(d) | 6.10(d) | 5.95–6.10 | 6.10(d) |
| H-7 | 6.05(dd) | 5.90(dd) | 5.80(dd) | 5.95–6.10 | 6.00(dd) |
| H-2 | 6.90(s) | 7.15(s) | 6.95(s) | 6.90(s) | 6.55–6.70 |
| additional H | 2.40–2.80(m, 5H, H-5'/COCH$_2$—CH$_2$CO) | 9.15(b, 1H replaces D$_2$O, (COOH)) | — | 2.45(b, 2H replace D$_2$O, (OH)); 3.55(t, 2H, CH$_2$OH) | 2.50(b, 2H replace D$_2$O, OH); 3.55(t, 2H, CH$_2$OH) 6.55–6.70 (m, 2H, H-1/2) |
| J$_{(A,B)}$ (Hz) | (4a, 7) = 4.0 (6, 8) = 7.1 (7, 8) = 10.4 (12, 12') = 17.0 | — | — | (10, 10') = 14.3 (12, 12') = 16.1 | (9, 9') = 14.1 (10, 10') = 15.1 (12, 12') = 15.6 |

| H-Atom | 70 |
|---|---|
| H-9 | 1.80–2.15 |
| H-9' | 1.80–2.15 |
| H-5 | 1.80–2.15 |
| H-5' | 2.40–2.70 |
| H-10 | 3.20(ddd) |
| H-10' | 3.60(ddd) |
| NCH$_2$ | 2.40–2.70 |
| OCH$_3$ | 3.80(s) |
| H-12 | 3.95(d) |
| H-12' | 4.50(d) |
| H-6 | 4.10(dd) |
| H-4a | 4.55(b) |
| H-8 | 5.95–6.05 |
| H-7 | 5.95–6.05 |
| H-2 | 6.90(s) |
| additional H | 2.40–2.70(m, 5H, H-5'/NCH$_2$CH$_2$) |
| J$_{(A,B)}$ (Hz) | — |

$^{13}$C-NMR(CDCl$_3$ [*in DMSO-d$_6$]; δ(ppm)):

| C-Atom | 66* | 68 | 69 | 70 | 65 |
|---|---|---|---|---|---|
| C-5 | 28.8, 30.2(t) | 29.4(t) | 29.7(t) | (t) | (t) |
| C-9 | 36.0, 37.8(t) | 33.2(t) | 33.2(t) | (t) | (t) |
| C-8a | 48.4(s) | 48.6(s) | 48.2(s) | (s) | (s) |
| C-10 | 43.6, 45.4(t) | 51.7(t) | 51.7(t) | (t) | (t) |
| NCH$_2$ | — | 54.9(t) | 52.0(t) | (t) | (t) |
| OCH$_3$ | 55.8(q) | 55.7(q) | 55.6(q) | (q) | (q) |
| C-12 | 48.8, 50.4(t) | 57.6(t) | 57.6(t) | (t) | (t) |
| C-6 | 59.3(d) | 61.4(d) | 61.7(d) | (d) | (d) |
| C-4a | 86.4, 86.6(d) | 88.3(d) | 88.4(d) | (d) | (d) |
| C-1 | 11.0, 112.1(s) | 114.3(s) | 121.8(d) | | |
| C-8 | 115.3(d) | 115.4(d) | 110.9(d) | (d) | (d) |
| C-2 | 128.4, 128.6(d) | 121.7(d) | 126.4(d) | (d) | (d) |
| C-7 | 126.3(d) | 127.9(d) | 127.5(d) | (d) | (d) |
| C-12a | 127.4(s) | 127.3(s) | 128.8(s) | (s) | (s) |
| C-12b | 133.2, 133.4(s) | 133.7(s) | 132.8(s) | (s) | (s) |
| C-3a | 143.8, 144.2(s) | 144.0(s) | 144.0(s) | (s) | (s) |
| C-3 | 146.5, 146.9(s) | 145.2(s) | 145.7(s) | (s) | (s) |
| additional C | 27.4(t, NCO—CH$_2$); 27.9(t, CH$_2$COOH); 170.0, 170.4(s, CON); 173.6, 173.8(s, COO) | 56.6(t, CH$_2$OH) | 56.7(t, CH$_2$OH) | | |

General Operating Rule for Splitting off Bromine with Zinc and Calcium Chloride

| Substance No. | Educt | R$_4$ | R$_5$ | R$_6$ | SF, MG |
|---|---|---|---|---|---|
| 112 | 4 | OH | H | 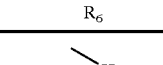 | C$_{16}$H$_{19}$NO$_3$ [273.22] |
| 73 | 52 | OH | H | 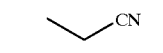 | C$_{18}$H$_{20}$N$_2$O$_3$ [312.37] |
| 74 | 54 | OH | H | 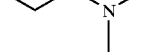 | C$_{22}$H$_{30}$N$_2$O$_4$ [386.50] |
| 43 | 42 | OH | H | 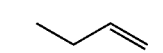 | C$_{19}$H$_{23}$NO$_3$ [313.40] |
| 46 | 45 | OH | H |  | C$_{23}$H$_{25}$NO$_3$ [363.46] |
| 72 | 64 | OH | H | 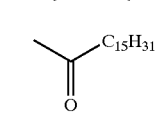 | C$_{32}$H$_{49}$NO$_4$ [511.75] |
| 47 | 44 | =O | |  | C$_{23}$H$_{23}$NO$_3$ [361.44] |

A solution of 500 mg educt and 1.0 g calcium chloride in 50 mL 50% ethanol is treated with 2.0 g freshly activated zinc powder and heated to reflux. Subsequently, the excess zinc is filtered off, washed with methanol and the residual solution is rotated. The residue is absorbed in 100 mL 1 N hydrochloric acid, made basic with concentrated aqueous ammonia and extracted with three times 50 mL ethyl acetate. The combined organic phases are washed once with a saturated aqueous sodium chloride solution, dried (Na$_2$SO$_4$), filtered and evaporated. The crude product is cleaned by column chromatography (15 g silica gel, solvent: CHCl$_3$: MeOH=9:1).

| Substance No. | Name | Reaction time | Yield | Melt. pt. |
|---|---|---|---|---|
| 112 | (6R)-4a,5,9,10,11,12-Hexahydro-1-brom-3-methoxy-6H-benzofuro[3a,3,2-ef][2]-benzazepin-6-ol | 1.5 h | 93% colorless crystals | 236–240° C. |
| 73 | (6R)-4a,5,9,10,11,12-Hexahydro-3-methoxy-11-(cyanomethyl)-6H-benzofuro[3a,3-ef][2]-benzazepin-6-ol | 3 h | 55% colorless crystals | 68–70° C. |
| 74 | (6R)-4a,5,9,10,11,12-Hexahydro-3-methoxy-11-(2-morpholinoethyl)-6H-benzofuro[3a,3,2-ef][2]benzazepin-6-ol | 3 h | 80% | |
| 72 | (6R)-4a,5,9,10,11,12-Hexahydro-3-methoxy-11-(1-oxohexadecyl)-6H-benzofuro[3a,3,2-ef][2]benzazepin-6-ol | 3 h | 84% colorless crystals | |
| 43 | (6R)-4a,5,9,10,11,12-Hexahydro-3-methoxy-11-(2-propenyl)-6H-benzofuro[3a,3,2-ef][2]-benzazepin-6-ol | 3 h | 96% | |
| 46 | (6R)-4a,5,9,10,11,12-Hexahydro-3-methoxy-11-(phenylmethyl)-6H-benzofuro[3a,3,2-ef][2]-benzazepin-6-ol | 3 h | 52% | |
| 47 | (6R)-4a,5,9,10,11,12-Hexahydro-3-methoxy-11-(phenylmethyl)-6H-benzofuro[3a,3,2-ef][2]-benzazepin-6-ol | 3.5 h | quantitative orange crystals | 159–162° C. |

$^1$H-NMR(CDCl$_3$ [*in DMSO-d$_6$]; δ(ppm)):

| H-Atom | 112 | 73 | 74 | 43 | 46 |
|---|---|---|---|---|---|
| H-9 | 1.70(dd) | 1.71(ddd) | 1.50(ddd) | 1.54(ddd) | 1.54(ddd) |
| H-9' | 1.70(dd) | 1.92–2.10 | 1.93–2.12 | 1.92–2.12 | 1.94–2.20 |
| H-5 | 2.05(dd) | 1.92–2.10 | 1.93–2.12 | 1.92–2.12 | 1.94–2.20 |
| H-5' | 2.30(dd) | 2.70(ddd) | 2.66(ddd) | 2.60–2.75 | 2.71(ddd) |
| H-10 | 3.00–3.20 | 3.12(ddd) | 3.16(ddd) | 2.60–2.75 | 3.17(ddd) |
| H-10' | 3.00–3.20 | 3.38(ddd) | 3.39(ddd) | 3.25(ddd) | 3.40(ddd) |
| NCH$_2$ | — | 3.58(s) | 2.40–2.66 | 3.16(d) | 3.68(s) |
| OCH$_3$ | 3.70(s) | 3.85(s) | 3.80(s) | 3.85(s) | 3.87(s) |
| H-12 | 3.75(d) | 3.78(d) | 3.81(d) | 3.80(d) | 3.80(d) |
| H-12' | 3.90(d) | 4.17(d) | 4.17(d) | 4.08(d) | 4.13(d) |
| H-6 | 4.10(b) | 4.14(b) | 4.12(b) | 4.13(b) | 4.15(dd) |
| H-4a | 4.45(b) | 4.60(b) | 4.58(b) | 4.61(b) | 4.66(b) |
| H-8 | 5.80(dd) | 6.00–6.04 | 5.98(dd) | 6.00(ddd) | 6.01(dd) |
| H-7 | 6.05(dd) | 6.00–6.04 | 6.08(d) | 6.10(dd) | 6.12(dd) |
| H-1 | 6.65(AB) | 6.61–6.70 | 6.62(AB) | 6.64(AB) | 6.66(AB) |
| H-2 | 6.55(AB) | 6.61–6.70 | 6.58(AB) | 6.57(AB) | 6.50(AB) |
| additional H | — | — | 2.40–2.66 | 5.12(dd, 2H, =CH$_2$); 5.82(ddt, 1H, =CH) | 7.20–7.39 (m, 5H, Ph) |
| | | | (m, 8H, NCH$_2$CH$_2$/Morph-2/6); 3.68(t, Morph-3/5) | | |
| J$_{(A,B)}$ (Hz) | (5, 5') = 13.4 (7, 8) = 9.8 (12, 12') = 15.1 | (9, 9') = 12.7 (10, 10') = 14.0 (12, 12') = 15.9 | — | (NCH$_2$, =CH) = 6.6 (6, 7) = 1.2 (6, 8) = 4.5 (7, 8) = 10.3 (12, 12') = 15.4 | (1, 2) = 8.2 (5, 5') = 15.6 (6, 8) = 4.8 (7, 8) = 10.2 (9, 9') = 13.6 (10, 10') = 14.1 (12, 12') = 15.3 |

| H-Atom | 72 | 47 |
|---|---|---|
| H-9 | 1.78(ddd) | 1.81(ddd) |
| H-9' | 2.18(ddd) | 2.16–2.48 |
| H-5 | 1.95(ddd) | 2.16–2.48 |
| H-5' | 2.42(ddd) | 2.77(dd) |
| H-10 | 2.68(ddd) | 3.10–3.42 |
| H-10' | 3.18(ddd) | 3.10–3.42 |
| NCH$_2$ | — | 3.71(s) |
| OCH$_3$ | 3.82(s) | 3.86(s) |
| H-12 | 3.93(d, Konf$_A$) 4.41(d, Konf$_B$) | 3.81(d) |
| H-12' | 4.68(d, Konf$_A$) 5.28(d, Konf$_B$) | 4.13(d) |
| H-6 | 4.14(b) | — |
| H-4a | 4.57(b) | 4.79(b) |
| H-8 | 5.93–6.08 | 7.01(dd) |
| H-7 | 5.93–6.08 | 6.06(d) |
| H-1 | 6.64–6.70, 6.81–6.88 | 6.70(d) |
| H-2 | 6.64–6.70, 6.81–6.88 | 6.52(d) |
| additional H | 0.89(t, ω-CH$_3$); 1.18–1.38(m, 22H, CH$_2$$^{(4-14)}$); 1.48–1.65(m, 4H, CH$_2$$^{(2-3)}$); 2.06(t, 2H, COCH$_2$) | 7.21–7.46(m, 5H, Ph) |
| J$_{(A,B)}$ (Hz) | — | (1, 2) = 8.1 (4a, 5/5') = 3.8 (4a, 8) = 1.9 (5, 5') = 17.8, (7, 8) = 10.4, (12, 12') = 15.6 |

$^{13}$C-NMR(CDCl$_3$ [*in DMSO-d$_6$]; δ(ppm)):

| C-Atom | 112 | | | | |
|---|---|---|---|---|---|
| C-5 | 30.6(t) | (t) | (t) | (t) | (t) |
| C-9 | 33.5(t) | (t) | (t) | (t) | (t) |
| C-8a | 48.1(s) | (s) | (s) | (s) | (s) |
| C-10 | 46.3(t) | (t) | (t) | (t) | (t) |
| NCH$_2$ | — | | | | |
| OCH$_3$ | 55.5(q) | (q) | (q) | (q) | (q) |
| C-12 | 52.8(t) | (t) | (t) | (t) | (t) |
| C-6 | 59.7(d) | (d) | (d) | (d) | (d) |
| C-4a | 86.7(d) | (d) | (d) | (d) | (d) |
| C-8 | 111.1(d) | (d) | (d) | (d) | (d) |
| C-7 | 119.5(d) | (d) | (d) | (d) | (d) |
| C-2 | 121.0(d) | (d) | (d) | (d) | (d) |
| C-1 | 127.4(d) | (d) | (d) | (d) | (d) |
| C-12a | 132.9(s) | (s) | (s) | (s) | (s) |
| C-12b | 133.8(s) | (s) | (s) | (s) | (s) |

-continued

| $^{13}$C-NMR(CDCl$_3$ [*in DMSO-d$_6$]; δ(ppm)): | | | | | |
|---|---|---|---|---|---|
| C-3a | 142.9(s) | (s) | (s) | (s) | (s) |
| C-3 | 146.3(s) | (s) | (s) | (s) | (s) |
| additional C | — | | | | |

| C-Atom | | | | | 47 |
|---|---|---|---|---|---|
| C-5 | (t) | (t) | (t) | (t) | 32.5(t) |
| C-9 | (t) | (t) | (t) | (t) | 36.9(t) |
| C-8A | (s) | (s) | (s) | (s) | 48.8(s) |
| C-10 | (t) | (t) | (t) | (t) | 51.5(t) |
| NCH$_2$ | | | | | 56.4(s) |
| OCH$_3$ | (q) | (q) | (q) | (q) | 55.6(q) |
| C-12 | (t) | (t) | (t) | (t) | 57.0(t) |
| C-6 | (d) | (d) | (d) | (d) | 194.0(s) |
| C-4a | (d) | (d) | (d) | (d) | 87.6(d) |
| C-8 | (d) | (d) | (d) | (d) | 111.5(d) |
| C-7 | (d) | (d) | (d) | (d) | 126.8(d) |
| C-2 | (d) | (d) | (d) | (d) | 144.1(d) |
| C-1 | (d) | (d) | (d) | (d) | 121.7(d) |
| C-12a | (s) | (s) | (s) | (s) | 129.3(s) |
| C-12b | (s) | (s) | (s) | (s) | 138.2(s) |
| C-3a | (s) | (s) | (s) | (s) | 143.6(s) |
| C-3 | (s) | (s) | (s) | (s) | 146.6(s) |
| additional C | | | | | 126.7(d, Ph-4); 127.8(s, Ph-1); 127.9(d, Ph-2/6); 128.5(d, Ph-3/5) |

O-TOS-Narwedine oxime (75)

A suspension of 1.05 g (3.51 mmol) narwedine oxime (76,77) in 20 mL absolute pyridine[ep] is treated with 1.33 g (7.03 mmol) p-toluolsulfonic acid chloride and stirred for 20 hours at room temperature. The reaction mixture is subsequently poured over 100 mL water and extracted with 50 mL ethyl acetate. The combined organic phases are washed once with a saturated aqueous sodium chloride solution, dried (Na$_2$SO$_4$, active carbon), filtered and evaporated. The crude product is cleaned by column chromatography (50 g silica gel, solvent CHCl$_3$=>CHCl$_2$: MeOH=9:1), whereby 1.27 g (80% of the theoretical yield.) yellow crystals with a melting point of 78–79° C. are obtained at 75.

DC: CHCl$_3$: MeOH=9:1

$^1$H-NMR (CDCl$_3$; δ (ppm)): 1.55–1.65, 1.80–1.95 (2* m, 2H, H-9/9'Conformer$_{A/B}$); 2.05–2.25 (m, 1H, H-5Conformer$_{A/B}$); 2.40, 2.43 (2* s, 6H, NCH$_3$, Ph-CH$_3$); 2.50–2.70 (m, 1H, H-5'Conformer $_{A/B}$); 2.95–3.25 (m, 1H, H-10Conformer $_{A/B}$); 3.60 3.85 (m, 2H, H-10'/12$_{Conformer\ A/B}$); 4.00–4.25 (m, 1H, H-12'$_{Conformer\ A/B}$); 4.55 (b, 1H, H-4a$_{Conformer\ A/B}$); 6.15, 7.10 (2* d, 1H, H-8$_{Conformer\ A/B}$); 6.40, 7.65 (2* d, 1H, H-7 $_{Conformer\ A/B}$); 6.50–6.70 (m, 2H, H-1/2$_{Conformer\ A/B}$); 7.20–7.35 (m, 2H, Ph-3/5$_{Conformer\ A/B}$); 7.75–7.90 (m, 2H, Ph-2/6$_{Conformer\ A/B}$)

$^{13}$C-NMR (DMSO-d$_6$; δ (ppm)): 21.1 (q, Ph-CH$_3$); 23.9 (t, C-5); 31.6 (t, C-9); 40.6 (q, NCH$_3$); 48.7 (s, C-8a); 52.9 (t, C-10); 55.5 (q, OCH$_3$); 59.2 (t, C-12); 84.3 (d, C-4a); 111.9 (d, C-2); 118.6, 121.6 (d, C-8$_{Conformer\ A/B}$); 125.5, 128.0 (d, C-7$_{Conformer\ A/B}$); 128.4 (d, Ph-2/6); 130.0 (d, Ph-3/5); 131.8 (s, C-12a); 136.1 (s, Ph-1); 137.5 (s, C-12b); 138.7 (d, C-1); 143.1 (s, C-3a); 145.4 (s, C-3); 145.8 (s, Ph-4); 159.8 (s, C-6)

rac., (−)- and (+)-)-methylnarwedine oxime (78, 79)

A solution of 300 mg (1.05 mmol) narwedine in 10 mL ethanol is treated with 88 mg (1.05 mmol) O-methylhydroxylamine and 53 mg (0.53 mmol) potassium bicarbonate and heated for 4 hours to reflux. Subsequently, the reaction mixture is evaporated, the residue is absorbed in 50 mL 1 N hydrochloric acid, made basic with concentrated aqueous ammonia and extracted 3 times with 30 mL ethyl acetate each. The combined organic phases are washed once with a saturated aqueous sodium chloride solution, dried (Na$_2$SO$_4$), filtered and evaporated, whereby quantitatively viscous substances (with a rotation of a$_D$$^{20}$[CHCl$_3$]=a$_D$$^{20}$ [CHCl$_3$]=−152° for 78 and/or a$_D$$^{20}$[CHCl$_3$]=+108° for 79) are obtained at 78/79.

DC: CHCl$_3$ : MeOH=9:1

$^1$H-NMR (CDCl$_3$; δ(ppm)): 1.70 (ddd, 1H, H-9); 2.20 (ddd, 1H, H-9'); 2.30–2.45 (m, 1H, H-5); 2.40 (s, 3H, NCH$_3$); 2.70 (ddd, 1H, H-5'); 3.00–3.35 (m, 2H, H-10/10'); 3.65, 3.70, 4.00, 4.10 (4* d, 2H, H-12$_{Conformer\ A/B}$/ 12'$_{Conformer\ A/B}$); 3.80 (s, 3H, OCH$_3$); 3.85, 3.90 (2* s, 3H, N—OCH$_{3\ Conformer\ A/B}$); 4.60 (b, 1H, H-4a); 6.15, 6.20, 6.75 (s, d, d, 2H, H-7/8$_{Conformer\ A/B}$); 6.55–6.70 (m, 2H, H-1/2)

Narwedine imine (80)

A solution of 100 mg (0.35 mmol) narwedine in 10 mL 7 N methanolic ammonia is heated to reflux in a glass autoclave for 10 hours at 100° C. Subsequently, the excess methanol is evaporated off in a rotary evaporator, whereby quantitatively colorless crystals with a melting point of 105–110° C. are obtained at 80.

DC: CHCl$_3$: MeOH=9:1

$^1$H-NMR (CDCl$_3$[formation of narwedine and decomposition products during measuring]δ (ppm)): 1.80 (ddd, 1H, H-9); 2.00–2.35 (m, 2H, H-5/9'); 2.45 (s, 3H, NCH$_3$); 2.80 (ddd, 1H, H-5'); 3.00–3.35 (m, 2H, H-10/10'); 3.70 (d, 1H. H-12); 3.80 (s, 2H, OCH$_3$); 4.05 (d, 1H, H-12'); 4.65 (b, 1H, H-4a); 6.15 (d, 1H, H-8); 6.45 (d, 1H, H-7); 6.55–6.70 (m, 2H, H-1/2)

rac, (+)- or (−)-narwedine oxime (76,77)

1.0 g (3.51 mmol) narwedine, 266 mg (3.86 mmol) hydroxylamine hydrochloride and 193 mg (1.93 mmol) potassium bicarbonate are heated to reflux in 30 mL 96% ethanol. The reaction mixture is spun in after 3 hours, the residue is absorbed in 50 mL 2 N hydrochloric acid and the product is precipitated with concentrated aqueous ammonia. After overnight crystallizing, a first fraction of 0.81 g (81% of the theoretical yield.) is obtained. After extraction of the theoretical yield mother fluid with three times 30 mL ethyl acetate a second fraction is obtained, whereby quantitatively colorless crystals with a melting point of 170–171° C. are obtained at 76, 77.

| | a$_D$$^{20}$[CHCl$_3$ | ee after CE* |
|---|---|---|
| (−)-Narwedine oxime (77) | −79° | 20% |
| (+)-Narwedine oxime (76) | +126° | 12% |
| DC: CHCl$_3$:MeOH = 9:1 | | |

*CE = Capillary electrophoresis $^1$H-NMR (CDCl$_3$; δ (ppm)): 1.70 (dd, 1H, H-9, J$_{(9,9')}$=13.4 Hz); 2.20 (ddd, 1H, H-9', J$_{(9,9')}$=13.4 Hz); 2.40 (s, 3H, NCH$_3$); 2.45 (dd, 1H, H-5, J$_{(5,5')}$=16.9 Hz); 3.10 (m, 2H, H-5', J$_{(5,5')}$=16.9 Hz); 3.30 (ddd, 1H, H-10, J$_{(10,10')}$=14.2 Hz); 3.75 (d, 1H, H-12, J$_{(12,12')}$=16.0 Hz); 3.80 (s, 3H, OCH$_3$); 3.85 (dd, 1H, H-10', J$_{(10,10')}$=14.2 Hz); 4.10 (d, 1H, H-12', J$_{(12,12')}$=16.0 Hz); 4.65 (b, 1H, H-4a); 6.20 (b, 2H, H-7/8); 6.55–6.65 (m, 2H, H-1/2)

$^{13}$C-NMR (DMSO-d$_6$; 22.3 (t, c-5); 32.8 (t, C-9); 41.2 (q, NCH$_3$); 48.7 (s, C-8a); 53.1 (t, C-10); 55.5 (q, OCH$_3$); 59.5 (t, C-12); 85.9 (d, C-4a); 111.6 (d, C-8); 121.1 (d, C-2); 122.5 (d, C-7); 129.5 (s, C-12a); 130.7 (d, C-1); 132.5 (s, C-12b); 143.1 (s, C-3a); 145.8 (s, C-3); 150.1 (s, C-6)

Conversion of narwedine with hydrazines and hydrazides:

| Substance No. | Rest $R_4$, $R_5$ | Name | Empirical formula, MG. |
|---|---|---|---|
| 81 | =N–NH–CH₃ | 4a,5,9,10,11,12-Hexahydro-3-methoxy-11-methyl-6H-benzofuro[3a,3,2-ef][2]benzazepin-6-on 2-Methylhydrazone | $C_{18}H_{23}N_3O_2$ [313.40] |
| 84 | =N–NH–C(O)H | formic acid-2-{4a,5,9,10,11,12-hexahydro-3-methoxy-11-methyl-6H-benzofuro[3a,3,2-ef][2]-benzazepin-6-yliden}hydrazide | $C_{18}H_{21}N_3O_3$ [327.39] |
| 83 | =N–NH–CH₂CH₂OH | 4a,5,9,10,11,12-Hexahydro-3-methoxy-11-methyl-6H-benzofuro[3a,3,2-ef][2]benzazepin-6-on 2-(2-Hydroxyethyl)hydrazone | $C_{19}H_{25}N_3O_3$ [343.43] |
| 86 | =N–NH–SO₂–C₆H₄–CH₃ | 4-methylbenzenesulfonic acid-2-{4a,5,9,10,11,12-hexahydro-3-methoxy-11-methyl-6H-benzofuro[3a,3,2-ef][2]-benzazepin-6-yliden}hydrazide | $C_{24}H_{27}N_3O_4S$ [453.56] |
| 85 | =N–NH–C(O)–O–C(CH₃)₃ | pyrocarbonic acid-t-butylester-2-{4a,5,9,10,11,12-hexahydro-3-methoxy-11-methyl-6H-benzofuro[3a,3,2-ef][2]-benzazepin-6-yliden}hydrazide | $C_{22}H_{29}N_3O_4$ [399.49] |
| 89 | =N–NH–C(O)–COOH | pyrocarbonic acid-2-{4a,5,9,10,11,12-hexahydro-3-methoxy-11-methyl-6H-benzofuro[3a,3,2-ef][2]-benzazepin-6-yliden}hydrazide | $C_{19}H_{21}N_3O_5$ [371.40] |
| 82 | =N–N(CH₃)₂ | 4a,5,9,10,11,12-Hexahydro-3-methoxy-11-methyl-6H-benzofuro[3a,3,2-ef][2]-benzazepin-6-on 2,2-Dimethylhydrazone | $C_{19}H_{25}N_3O_2$ [327.43] |
| 88 | =N–NH–C(=NH)–NH₂ | 2-{4a,5,9,10,11,12-Hexahydro-3-methoxy-11-methyl-6H-benzofuro[3a,3,2-ef][2]-benzazepin-6-yliden}-hydrazincarboximidamide | $C_{18}H_{23}N_5O_2$ [341.42] |
| 90 | =N–NH₂ | 4a,5,9,10,11,12-Hexahydro-3-methoxy-11-methyl-6H-benzofuro[3a,3,2-ef][2]benzazepin-6-on Hydrazone | $C_{17}H_{21}N_3O_2$ [299.38] |
| 87 | =N–NH–C(O)–NH₂ | carbamic acid-2-{4a,5,9,10,11,12-hexahydro-3-methoxy-11-methyl-6H-benzofuro[3a,3,2-ef][2]-benzazepin-6-yliden}hydrazide | $C_{18}H_{22}N_4O_3$ [342.40] |

Method: A solution of 500 mg (1.75 mmol) narwedine and 1.1 to 1.2 equivalents N-alkylhydrazone or acid hydrazide, respectively, in 10 mL ethanol is treated with 0.25 equivalents (43 mg, 0.44 mmol) concentrated sulfuric acid and heated to reflux. The reaction mixture is then evaporated, the residue is absorbed in 50 mL 1 N hydrochloric acid, made basic with concentrated aqueous ammonia and the resulting precipitate is evaporated in a rotary evaporator or the aqueous phase is extracted three times with 30 mL each of ethyl acetate The precipitate is dried at 50° C./50 mbar, the combined organic phases are washed once with a saturated aqueous sodium chloride solution, dried ($Na_2SO_4$), filtered and evaporated.

DC: $CHCl_3$: MeOH=9:1

| Substance No. | Reagent equ. $H_2SO_4$ | Reaction time | Yield | Melting point |
|---|---|---|---|---|
| 81 | Methylhydrazin; 0.25 | 4 h | 76% yellow crystals | 97–99° C. |
| 84 | Ameisensäurehydrazide; 0.0 | 48 h | 63% yellow crystals | 145–148° C. |
| 83 | 2-Hydrazinoethanol; 0.0 | 30 h | 61% yellow crystals | 100–105° C. |

-continued

| Substance No. | Reagent equ. $H_2SO_4$ | Reaction time | Yield | Melting point |
|---|---|---|---|---|
| 86 | p-Toluolsulfonsäurehydrazid; 0.25 | 6 h | 97% colorless crystals | 210–212° C. |
| 85 | t-Butylcarbazat; 0.25 | 4 h | quantitative colorless crystals | Tranformation at 155–160° C., decomposition >200° C. |
| 89 | Oxalsäureethylesterhydrazide; 0.25* | 30 h | 64% yellow crystals | 189–191° C. |

-continued

| Substance No. | Reagent equ. $H_2SO_4$ | Reaction time | Yield | Melting point |
|---|---|---|---|---|
| 82 | N,N-Dimethylhydrazin; 0.25 | 12 h | 78% oily substance | — |
| 88 | Aminoguanidin Hydrogencarbonat; 0.0 | 20 h | quantitative yellow crystals | 112–113° C. |
| 90 | 10 Äqu. Hydrazinhydrat; 2.5 | 2 h | 94% oily substance | — |
| 87 | Semicarbazid Hydrochlorid; 0.5 Äqu. $KHCO_3$ | 4 h | 88% colorless crystals (Lit. [] % d. Th.) | decomposition ab 225° C. (Lit. [] Zers. at ° C.) |

$^1$H-NMR($CDCl_3$ [*in DMSO-$d_6$]; δ(ppm)):

| H-Atom | 81 | 84 | 83 | 86 | 85 |
|---|---|---|---|---|---|
| H-9 | 1.75(ddd) | 1.70(dd) | 1.70(ddd) | 1.30(ddd) | 1.70(ddd) |
| H-9' | 2.10–2.35 | 2.20(dd) | 2.20(ddd) | 2.15(ddd) | 2.20(ddd) |
| H-5 | 2.10–2.35 | 2.50(dd) | 2.35(dd) | 2.50(b) | 2.35–2.45 |
| H-5' | 2.90–3.30 | 3.00–3.30 | 2.70(ddd) | 3.15(dd) | 2.75(ddd) |
| H-10 | 2.90–3.30 | 3.00–3.30 | 3.00–3.40 | 3.25–3.45 | 3.00–3.35 |
| H-10' | 2.90–3.30 | 3.40(dd) | 3.00–3.40 | 3.25–3.45 | 3.00–3.35 |
| $NCH_3$ | 2.45(s) | 2.45(s) | 6.65(s) | 2.40(s) | 2.40(s) |
| $OCH_3$ | 3.85(s) | 3.85(s) | 3.80(s) | 4.10(s) | 3.80(s) |
| H-12 | 3.70(d) | 3.70(d) | 3.68(d) | 3.58(d) | 3.70(d) |
| H-12' | 4.10(d) | 4.05(d) | 4.07(d) | 4.30(d) | 4.10(d) |
| H-4a | 4.70(b) | 4.70(b) | 4.70(b) | 4.60(b) | 4.15(b) |
| H-8 | 5.96(d) | 6.10–6.40 | 6.16(d) | 6.00(d) | 6.35(d) |
| H-7 | 6.98(dd) | 6.10–6.40 | 5.98(dd) | 6.32(d) | 6.20(dd) |
| H-1/2 | 6.48–6.68 | 6.50–6.70 | 6.55–6.65 | 6.55–6.78 | 6.55–6.70 |
| additional H | 2.50(s, 3H, N—$NCH_3$); more conform B: 5.80–6.06(m, 2H, H-7/8) | 8.65(b, 1H, (CHO); 10.40 (b, 1H, replaces $D_2O$, NH) | 3.00–3.40(m, 6H, H-10/10', N—$CH_2$—$CH_2$—O); more conform B: 4.07, 4.14(2* d, 2H, H-12/12'); 6.38(dd, 1H, H-8); 6.70(dd, 1H, H-7) | 3.70(s, 3H, $PhCH_3$); 7.36 (d, 2H, Ph-3/5); 7.76(d, 2H, Ph-2/6) | 1.50(s, 9H, $C(CH_3)_3$); 7.70 (b, 1H replaces $D_2O$, NH) |
| $J_{(A,B)}$ (Hz) | (7, 8) = 10.2 | (12, 12') = 14.2 | (7, 8) = 14.4; (12, 12') = 15.2; ($12_B$, $12_B'$) = 7.2 | (7, 8) = 10.2; (12, 12') = 16.0 | (7, 8) = 8.9; (12, 12') = 13.4 |

| H-Atom | 89 | 82 | 88 | 90 | 87 |
|---|---|---|---|---|---|
| H-9 | 1.85(ddd) | 1.80(ddd) | 1.65(dd) | 1.70(dd) | 1.65(dd) |
| H-9' | 2.30(ddd) | 2.20(ddd) | 2.00–2.40 | 2.15–2.40 | 2.20(ddd) |
| H-5 | 2.75(dd) | 2.35 2.50 | 2.00–2.40 | 2.15–2.40 | 2.50(dd) |
| H-5' | 3.05–3.35 | 2.75(ddd) | 2.75(ddd) | 2.65(ddd) | 2.70(dd) |
| H-10 | 3.05–3.35 | 3.00–3.35 | 2.95(dd) | 3.05(ddd) | 2.95–3.20 |
| H-10' | 3.05–3.35 | 3.00–3.35 | 3.10–3.30 | 3.25(ddd) | 2.95–3.20 |
| $NCH_3$ | 2.45(s) | 2.55(s) | 2.25(s) | 2.40(s) | 2.35(s) |
| $OCH_3$ | 3.85(s) | 3.85(s) | 3.70(s) | 3.80(s) | 3.75(s) |
| H-12 | 3.75(d) | 3.70(d) | 3.58(d) | 3.70(d) | 3.55–3.70 |
| H-12' | 4.10(d) | 4.10(d) | 4.06(d) | 4.08(d) | 3.95–4.15 |
| H-4a | 4.70(b) | 4.65(b) | 4.58(b) | 4.20(b) | 4.60(b) |
| H-8 | 6.05(d) | 6.15–6.40 | 6.00–6.15 | 6.05(d) | 5.95(d) |
| H-7 | 6.95(d) | 6.15–6.40 | 6.00–6.15 | 6.20(d) | 6.90(d) |

-continued

| | | | | | |
|---|---|---|---|---|---|
| H-1/2 additional H | 6.60–6.75 | 6.55–6.75 2.40, 2.50(2*s, 6H, N(CH$_3$)$_2$) | 6.55, 6.68(AB) 5.55–5.90(b, 4H replace D$_2$O, NH); more conform B: 6.95(d, 1H, H-7) | 6.55–6.70 5.30(b, 2H replace D$_2$O, NH$_2$); more conform B: 6.35(d, 1H, H-8); 6.95(d, 1H, H-7) | 6.50–6.65 more conform B: 3.55–3.70(m, 1H, H-12$_{A/B}$); 3.95–4.15(m, 1H, H-12'$_{A/B}$); 4.65(b, 1H, H-4a$_B$); 6.10(s, 1H, H-8$_B$); 6.50–6.65(m, 3H, H-1/2/7$_B$) |
| J$_{(A,B)}$ (Hz) | (5, 5') = 17.8; (7, 8) = 10.5; (9, 9' = 13.7; (12, 12') = 15.4 | (12, 12') = 16.0 | (1, 2) = 8.2; (12, 12') = 15.3 | (12, 12') = 15.1 | (5, 5') = 16.9 (7$_A$, 8$_A$) = 9.8 |

$^{13}$C-NMR(CDCl$_3$ [*in DMSO-d$_6$]; d(ppm))

86: 24.8(t, C-5); 31.7(t, C-9); 41.2(q, NCH$_3$); 53.0(t, C-10); 47.8(s, C-8a); 55.5(q, OCH$_3$); 58.8(t, C-12); 85.5(d, C-4a); 111.9(d, C-8); 122.3(d, C-2); 125.0(d, C-7); 125.2(s, Ph-1); 127.5(d, Ph-2/6); 129.5(d, Ph-3/5); 132.2(d, (C-1); 132.3(s, C-12a); 136.2(s, C-12b); 143.3(s, C-3a); 143.8(s, Ph-4); 145.8(s, C-3); 149.8(s, C-6)

85*: 24.5(t, C-5); 28.1(q, C(CH$_3$)$_3$); 32.4(t, C-9); 41.2(q, NCH$_3$); 48.2(s, C-8a); 53.1(t, C-10); 55.5(q, OCH$_3$); 59.3(t, C-12); 79.4(s, C(CH$_3$)$_3$); 86.0(d, C-4a); 111.7(d, C-8); 121.5(d, C-2); 125.5(d, C-7); 131.2(d, C-1); 128.5(s, C-12a); 132.5(s, C-12b); 143.3(s, C-3a); 145.6(s, C-3); 145.8(s, C-6); 153.0(s, CO)

(–)-Alkyl galanthamine halogenide

| Product | Empirical Formula | Designation | R |
|---|---|---|---|
| | C$_{23}$H$_{31}$BrNO$_3$ [401.95] | (–)-Pentylgalanthaminium-bromide | –CH$_2$CH$_2$CH$_2$CH$_2$CH$_3$ |
| 91 | C$_{21}$H$_{30}$ClN$_2$O$_3$ [358.49] | (–)-2-Dimethylaminoethylgalanthaminium-chloride | –CH$_2$CH$_2$N(CH$_3$)$_2$ |
| 92 | C$_{23}$H$_{32}$ClN$_2$O$_3$ [419.97] | (–)-2-Pyrrolidin-N-ethylgalanthaminium-chloride | –CH$_2$CH$_2$-pyrrolidinyl |
| 93 | C$_{23}$H$_{32}$ClN$_2$O$_4$ [435.97] | (–)-2-Morpholin-N-ethylgalanthaminium-chloride | –CH$_2$CH$_2$-morpholinyl |
| 94 | C$_{24}$H$_{34}$ClN$_2$O$_3$ [434.0] | (–)-2-Piperidin-N-ethylgalanthaminium-chloride | –CH$_2$CH$_2$-piperidinyl |
| 95 | C$_{25}$H$_{36}$ClN$_2$O$_3$ [448.03] | (–)-3-Piperidin-N-propylgalanthaminium-chloride | –CH$_2$CH$_2$CH$_2$-piperidinyl |
| | C$_{20}$H$_{25}$BrNO$_3$ [407.33] | (–)-Allylgalanthaminium-bromide | –CH$_2$CH=CH$_2$ |

General Procedure 800 mg (2.78 mmol) (–)-galanthamine and 3.84 g (27.8 mmol) potassium carbonate were presented in 100 mL acetone. After adding 1.5 equivalents of halogenide and a spatula tip of potassium iodide, the reaction mixture was stirred under reflux for 24–36 hours. The potassium carbonate was then evaporated in a rotary evaporator and the filtrate was evaporated. The oily residue was finally cleaned by column chromatography in a mixture of trichloromethane and ammoniacal methanol (9:1).

DC: CHCl$_3$ : MeOH(10% NH$_3$)=9:1

| Product | Yield [% d. Th.] | *α$_D$ (25° C., c = 1) | Melting Point [° C.] |
|---|---|---|---|
| | 71 | –83.7° | 130–132 |
| 91 | 72 | –46.6° | 143–150 |
| 92 | 43 | –62.5° | 120–125 |
| 93 | 94 | –52.3° | 225–229 |
| 94 | 48 | –70.8° | 136–140 |
| 95 | 70 | –71.5° | 126–131 |
| | 41 | –74.3° | 188–192 |

| $^1$H—NMR [DMSO-d$_6$; δ (ppm)]: | | | |
|---|---|---|---|
| Proton | 91 | 92 | 93 |
| H$_a$-5 | 2.10; m | 2.10; m | 2.00; m | 2.00; m |
| H$_a$-1 | 2.20; m | 2.30; m | 2.50; m | 2.20; m |
| H$_b$-5 | 2.30; m | 2.45; m | 2.55; m | 2.50; m |
| CH$_3$—N— | 3.50; s | 2.85; s | 2.95; s | 3.00; s |
| H$_b$-1 | 2.70; br.d | 2.50; m | 2.65; m | 2.90; m |
| H$_b$-6 | 4.25; m | 3.10; m | 3.10; m | 3.50; m |
| H$_a$-6 | 4.30; m | 3.25; m | 3.80; m | 3.60; m |
| H$_b$-8 | 4.90; br.d | 4.50; br.d | 4.15; br.d | 4.15; br.d |
| CH$_3$—O— | 3.85; s | 3.80; s | 3.75; s | 3.80; s |
| H$_a$-8 | 5.25; br.d | 5.05; br.d | 5.15; br.d | 5.10; br.d |
| H-12a | 4.70; t | 4.70; t | 4.65; t | 4.70; t |
| H-2 | 4.20; m | 4.10; m | 3.90; m | 3.90; m |
| H-3 | 6.15; dd | 5.95; dd | 6.00; dd | 6.05; dd |
| H-4 | 6.45; d | 6.20; d | 6.15; d | 6.20; d |
| H-9 | 6.70; d | 6.80; d | 6.70; d | 6.75; d |
| H-10 | 7.10; d | 6.90; d | 6.85; d | 6.85; dd |
| diverse H | 0.95 (t, 3H, CH$_3$—) 1.35–1.50 (m, 4H, 2 × —CH$_2$—) 1.70 (m, 2H, —CH$_2$—) 2.0 (t, 2H, —N—CH$_2$—) | 3.35 (s, 6H, 2 × CH$_3$—N—) 3.40 (t, 2H, —CH$_2$—N—) 3.90 (t, 2H, —N—CH$_2$—) | 1.75 (m, 4H, 2 × CH$_2$*) 2.60 (m, 2H, —CH$_2$—N—) 3.10 (m, 4H, 2 × —CH$_2$—N—*) 3.80 (m, 2H, —N—CH$_2$—) *)Pyrrolidin | 2.50–2.60 (m, 6H, 2 × —CH$_2$—N—*) 2.55 (m, 2H, —CH$_2$—N—) 3.0–3.20 (m, 6H, 3 × —O—CH$_2$—*) *)Morpholin |

| Proton | 94 | 95 | |
|---|---|---|---|
| H$_a$-5 | 2.00; m | 1.45; m | 2.13; m |
| H$_a$-1 | 2.20; m | 2.00; m | 2.25; m |
| H$_b$-5 | 2.50; m | 2.15; m | 2.50; m |
| CH$_3$—N— | 3.15; s | 2.85; s | 2.75; s |
| H$_b$-1 | 2.65; br.d | 2.45; br.d | 2.50; m |
| H$_b$-6 | 3.00; m | 3.30; m | 3.35; m |
| H$_a$-6 | 3.10; m | 3.60; m | 3.35; m |
| H$_b$-8 | 5.15; br.d | 4.45; br.d | 4.50; m |
| CH$_3$—O— | 3.85; s | 3.80; s | 3.75; s |
| H$_a$-8 | 5.40; br.d | 5.05; br.d | 5.05; br.d |
| H-12a | 4.65; t | 4.65; t | 4.65; t |
| H-2 | 4.15; m | 4.10; m | 4.15; m |
| H-3 | 6.15; dd | 5.95; dd | 5.90; dd |
| H-4 | 6.40; d | 6.20; d | 6.20; d |
| H-9 | 6.70; d | 6.75; d | 6.85; d |
| H-10 | 7.05; d | 6.85; d | 6.90; d |
| diverse H | 1.40–1.60 (m, 6H, 3 × —CH$_2$—*) 2.40 (m, 4H, 2 × —CH$_2$—N—*) 2.95 (m, 2H, —N—CH$_2$—CH$_2$—N—) 4.35 (m, 2H, —N—CH$_2$—CH$_2$—N—) *)Piperidin | 1.50–1.65 (m, 6H, 3 × —CH$_2$—*) 2.50 (m, 2H, —CH$_2$—CH$_2$—CH$_2$—) 3.10–3.45 (m, 6H, 3 × —CH$_2$—N—*) 3.75 (t, 2H, —N—CH$_2$—CH$_2$—CH$_2$— *)Piperidin | 4.35 (d, 2H, —N—CH$_2$—) 5.70 (d, 2H, —CH=CH$_2$) 6.30 (m, 1H, —CH=CH$_2$) |

| $^{13}$C—NMR [DMSO-d$_6$; δ (ppm)]: | | | |
|---|---|---|---|
| C-Atom | 91 | 92 | 93 |
| C-1 | 27.9; t | 31.0; t | 30.8 | 28.0; t |
| C-5 | 29.6; t | 32.1; t | 31.9 | 30.6; t |
| CH$_3$—N— | 46.2; q | 44.5; q | 43.6 | 52.8; q |
| C-4a | 46.2; s | 45.9; s | 45.9 | 45.9; s |
| C-6 | 60.1; t | 51.6; t | 49.2 | 50.2; t |
| CH$_3$—O | 55.7; q | 55.6; q | 55.6 | 66.0; q |
| C-8 | 60.1; t | 60.3; t | 60.1 | 59.7; t |
| C-2 | 60.8; d | 59.5; d | 59.5 | 59.7; d |
| C-12a | 88.0; d | 86.5; d | 86.6 | 86.8; d |
| C-3 | 112.0; d | 121.1; d | 112.0 | 111.8; d |
| C-4 | 124.9; d | 123.8; d | 123.9 | 123.8; d |
| C-9 | 130.0; d | 125.2; d | 125.1 | 124.8; d |
| C-10 | 132.3; d | 130.1; d | 129.8 | 130.0; d |
| C-8a | 116.0; s | 117.9; s | 118.0 | 117.5; s |
| C-11b | 132.3; s | 132.7; s | 132.6 | 132.5; s |
| C-11a | 146.0; s | 145.4; s | 145.4 | 145.5; s |
| C-11 | 146.1; s | 146.4; s | 146.3 | 146.2; s |
| diverse C | 13.5 (q, CH$_3$—) 21.9 (t, CH$_3$—$\underline{C}$H$_2$—) | 27.5 (q, CH$_3$—N—) 29.5 (q, CH$_3$—N—) | 23.1 (t, C-3* u. C-4*) 53.4 (t, C-2* u. C-5*) | 51.8 (t, —N—CH$_2$—$\underline{C}$H$_2$—) 55.4 (t, 2 × —CH$_2$—N—*) |

-continued

| | $^{13}$C—NMR [DMSO-d$_6$; δ (ppm)]: | | | |
|---|---|---|---|---|
| | 21.9 (t, CH$_2$—CH$_2$—CH$_2$—) | 49.7 (t, —CH$_2$—N—) | 65.0 (t, —CH$_2$—N—) | 58.5 (t, —N—CH$_2$—CH$_2$—) |
| | 22.3 (t, —N—CH$_2$—CH$_2$—) | 64.9 (t, —N—CH$_2$—) | 65.9 (t, —N—CH$_2$—) | 60.1 (t, 2 × —O—CH$_2$—*) |
| | 60.1 (t, —N—CH$_2$—CH$_2$—) | | *)Pyrrolidine | *)Morpholine |

| C-Atom | 94 | 95 |
|---|---|---|
| C-1 | 25.9; t | 30.8; t |
| C-5 | 30.0; t | 40.0; t |
| CH$_3$—N— | 46.6; q | 45.9; q |
| C-4a | 46.6; s | 54.8; s |
| C-6 | 53.8; t | 55.6; t |
| CH$_3$—O— | 56.2; q | 53.6; q |
| C-8 | 60.8; t | 59.6; t |
| C-2 | 61.4; d | 59.9; t |
| C-12a | 88.5; d | 86.7; d |
| C-3 | 112.4; d | 112.0; d |
| C-4 | 123.4; d | 123.9; d |
| C-9 | 125.4; d | 125.0; d |
| C-10 | 129.8; d | 125.0; d |
| C-8a | 117.6; s | 130.0; s |
| C-11b | 133.0; s | 132.5; s |
| C-11a | 146.1; s | 145.4; s |
| C-11 | 146.4; s | 146.4; s |
| diverse C | 23.1 (t, C-4*) | 19.3 (t, N—CH$_2$—CH$_2$—CH$_2$—N—) |
| | 23.9 (t, C-3* u. C-5*) | 23.5 (t, C-4*) |
| | 24.7 (t, —N—CH$_2$—CH$_2$—N—) | 25.0 (t, C-3* u. C-5*) |
| | 54.5 (t, C-2* u. C-6*) | 53.6 (t, C-2* u. C-6*) |
| | 60.8 (t, —N—CH$_2$—CH$_2$—N—) | |
| | *)Piperidin | *)Piperidin |

(+)-Alkyl galanthamine halogenide

| Product | Empirical Formula | Name | R |
|---|---|---|---|
| 96 | C$_{23}$H$_{32}$ClN$_2$O$_4$ [435.97] | (−)-2-Morpholin-N-ethylgalanthaminium-chloride | 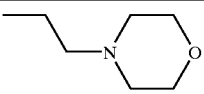 |
| 97 | C$_{25}$H$_{36}$ClN$_2$O$_3$ [448.03] | (−)-3-Piperidin-N-propylgalanthaminium-chloride | 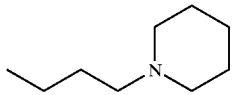 |

General Procedure 800 mg (2.78 mmol) (−)-galanthamine and 3.84 g (27.8 mmol) potassium carbonate were presented in 100 mL acetone. After adding 1.5 equivalents of halogenide and a spatula tip of potassium iodide, the reaction mixture was stirred under reflux for 24–36 hours. The potassium carbonate was then evaporated in a rotary evaporator and the filtrate was evaporated. The oily residue was finally cleaned by column chromatography in a mixture of trichloromethane and ammoniacal methanol (9:1).

DC: CHCl$_3$: MeOH (10% NH$_3$)=9:1

| Products | Yield [% d. Th.] | α$_D$ (25° C., c = 1) | Melting Point [° C.] |
|---|---|---|---|
| 96 | 44 | +48.6° | 185–190 |
| 97 | 65 | +64.0° | 118–194 |

N-Propargyl-galanthamine bromide (99)

IR (KBr): 3489 s br; 3218 s; 3014 w; 2915 s br; 2133 w; 1619 s; 1507 m; 1440 s; 1274 s; 1203 m; 1070 s; 1012 m; 951 m; 865 w; 791 s cm$^{-1}$ $^1$H-NMR (D$_2$O) δ: 6.95 (m, 2H); 6.12 (m, 2H); 5.08 (d, 1H); 4,70 (m, 2H); 4.46 (m, 2H); 4.29 (m, 2H); 4.11 (m, 1H); 3.80 (s, 3H); 3.69 (m, 1H); 3.00 (s, 3H); 2.41 (m, 2H); 2.20 (m, 2H).

$^{13}$C-NMR (D$_2$O) δ: 148.1 (s); 147.9 (s); 134.5 (s); 130.2 (d); 127.7 (d); 127.0 (d); 119.4 (q); 114.7 (d); 89.6 (d); 85.0 (d); 72.6 (s); 67.5 (t); 63.3 (t); 62.4 (d); 61.0 (t); 58.1 (q); 48.1 (s); 46.3 (q); 33.5 (t); 31.3 (t).

N-Acetamido-galanthamine bromide (100)

$^1$H-NMR (D$_2$O) δ: 6.95 (m, 2H); 6.13 (m, 2H); 5.18 (d, 1H); 4.70–4.28 (m, 7H); 3.83 (s, 3H); 3.08 (s, 3H); 2.50 (d, 1H); 2.39 (d, 1H); 2.18 (m, 2H).

$^{13}$C-NMR (D$_2$O) δ: 168.7 (s); 148.2 (s); 148.0 (s); 134.7 (s); 130.2 (d); 128.2 (d); 127.2 (d); 119.5 (s); 114.8 (d); 89.7 (d); 68.3 (t); 64.0 (t); 62.5 (d); 59.6 (t); 58.2 (q); 48.2 (q); 33.5 (t); 31.3 (t); 18.9 (q).

(−)-Galanthamine-N-oxide (98)

1.5 g (4.08 mmol) (−)-galanthamine hydrobromide are dissolved in 50 mL water, precipitated with concentrated aqueous ammonia and extracted with three times 25 mL trichloromethane. The organic phase is compressed to 30 to 50 mL and treated with 1.4 g (4.08 mmol) 50% metachloroperbenzoic acid. After 30 minutes, the reaction mixture is evaporated and placed on a pan column. The major part of the theoretical yield metachloroperbenzoic acid is then separated with trichloromethane, and the N-oxide is then washed out with trichloromethane: methanol=1:1. The further cleaning of the theoretical yield N-oxide is effected by means of MPLC (60 g $SiO_2$, LM: $CHCl_3$: MeOH=2:1), whereby quantitatively colorless crystals with a melting point of 80–85° C. and a rotation of $a_D^{26}$[MeOH]=−102.9° at 98.

DC: $CHCl_3$: MeOH=8:2

$^1$H-NMR DMSO-$d_6$; δ (ppm)): 1.75–1.95 (m, 1H, H-9); 2.00–2.40 (m, 3H, H-5/5'/9'); 2.95 (s, 3H, $NCH_3$); 3.30–3.75 (m, 2H, H-10/10'); 3.75 (s, 3H, $OCH_3$); 4.10 (b, 1H, H-12); 4.35 (d, 1H, H-12'); 4.60 (b, 1H, H-6); 4.95 (breites d, 1H, H-4a); 5.90 (dd, 1H, H-8); 6.15 (b, 1H, H-7); 6.75–6.90 (m, 2H, H-1/2)

$^{13}$C-NMR (DMSO-$d_6$; δ (ppm)): 31.2 (t, C-5); 34.3 (t, C-9); 45.6 (s, C-8a); 52.5 (q, $NCH_3$); 55.5 (q, $OCH_3$); 59.5 (d, C-6); 69.0 (t, C-10); 73.9 (t, C-12); 86.6 (d, C-4a); 112.0 (d, C-8); 120.0 (s, C-12a); 122.9 (d, C-7); 125.1 (d, C-2); 130.3 (d, C-1), 132.0 (s, C-12b); 144.9 (s, C-3a); 146.5 (s, C-3)

(6R)-4a,5,9,10,11,12-hexahydro-1-bromo-3-methoxy-11-methyl-12-oxo-6H-benzofuro[3a,3,2-ef][2]benzazepin-6-ol (102)

A suspension of 450 mg (1.19 mmol) 4a,5,9,10,11,12-hexahydro-1-bromo-3-methoxy-11-methyl-12-oxo-6H-benzofuro[3a,3,2-ef][2]benza-zepin-6-on (101) in 10 mL absolute tetrahydrofuran is treated at 0° C. with 3.6 mL (3.6 mmol) 1 N L-Selectride solution in tetrahydrofuran. After 30 minutes, it is hydrolyzed with 5 mL water : tetrahydrofuran 1:1. The reaction mixture is then evaporated, the residue is absorbed in 80 mL 2N hydrochloric acid and stirred for 1 hour at room temperature. Subsequently, it is extracted three times with 40 mL each of ethyl acetate. The combined organic phases are washed once with saturated aqueous sodium chloride solution, dried ($Na_2SO_4$), filtered and condensed by evaporation, whereby a quantitative crude product is obtained, which is cleaned by column chromatography (15 g silica gel, flow agent: $CHCl_3$: MeOH=9:1), whereby quantitative colorless crystals are obtained with a melting point of 188–189° C. at 102.

DC: $CHCl_3$: MeOH=8:2

$^1$H-NMR ($CDCl_3$; δ (ppm)): 1.73 (ddd, 1H, H-9, $J_{(9,9')}$=15.1 Hz); 2.03 (ddd, 1H, H-9', $J_{(9,9')}$=15.1 Hz); 2.27 (ddd, 1H, H-5, $J_{(5,5')}$=14.3 Hz); 2.64 (ddd, 1H, H-5', $J_{(5,5')}$=14.3 Hz); 3.18 (s, 3H, $NCH_3$); 3.19 (ddd, 1H, H-10, $J_{(10,10')}$=14.8 Hz); 3.75 (ddd, 1H, H-10', $J_{(10,10')}$=14.8 Hz); 3.86 (s, 3H, $OCH_3$); 4.10 (b, 1H, H-6); 4.69 (b, 1H, H-4a); 5.48 (d, 1H, H-8, $J_{(7,8)}$=10.0 Hz); 5.88 (dd, 1H, H-7, $J_{(7,8)}$=10.0 Hz); 7.10 (s, 1H, H-2)

$^{13}$C-NMR ($CDCl_3$; δ (ppm)): 29.8 (t, C-5); 34.1 (q, $NCH_3$); 38.2 (t, C-9); 48.3 (s, C-8a); 48.8 (t, C-10); 56.3 (q, $OCH_3$); 60.9 (d, C-6); 89.9 (d, C-4a); 113.8 (s, C-1); 118.0 (d, C-8); 123.3 (s, C-12a); 126.3 (d, C-7); 130.8 (d, C-2); 132.1 (s, C-12b); 144.8 (s, C-3); 146.2 (s, C-3a); 165.1 (s, C-12)

Manufacture of Products 105, 107

Method: A mixture of 500 mg (1.42 mmol) N-demethyl-bromo-galanthamine (4), 391 mg (2.84 mmol) potassium carbonate and 272 mg (1.70 mmol) potassium iodide is thoroughly ground in a mortar. The mixture is then treated in 20 mL absolute acetone with 1.2 equivalents of halogenide reagent and heated to reflux. After complete conversion (DC), the reaction mixture is condensed by evaporation, the residue is absorbed in 100 ml 2 N hydrochloric acid, washed with ethyl acetate, made basic with concentrated aqueous ammonia and the precipitate is their evaporated in a rotary evaporator or extracted three times with 30 mL each of ethyl acetate. The precipitate is dried at 50° C./50 mbar, the combined organic phases are washed once with saturated aqueous sodium chloride solution, dried ($Na_2SO_4$, active carbon), filtered and evaporated. Additional cleaning is effected by column chromatography (15 g silica gel, flow agent: $CHCl_3$>>>$CHCl_3$: MeOH=9:1). DC: $CHCl_3$: MeOH=8:2

105:

Educt: (4) and (136). Yield: 62.3% of the theoretical yield. colorless foam $^1$H-NMR ($CDCl_3$; δ (ppm)): 2.36–1.36 (m, 12 H); 2.62 (ddd, 1H); 2.89–3.35 (m, 7H); 3.60 (2H, m), 3.80 (s, 3H); 3.85 (d, 1H); 4.10 (dd, 1H); 4.29 (H, b), 4.48 (d, 1H); 4.56 (b, 1H), 5.90–6.05 (m, 2H); 6.85–6.69 (4H, m), 7.23 (2H, m)

107:

Educt: (4) and (137). Yield: 44.9% of the theoretical yield. colorless foam.

$^1$H-NMR ($CDCl_3$; δ (ppm)): 1.65–1.85 (4H, m), 2.20–1.90 (m, 6 H); 2.60–2.28 (2H, m) 2.62 (ddd, 1H); 2.89–3.35 (m, 5H); 3.60 (2H, m), 3.80 (s, 3H); 3.85 (d, 1H); 4.10 (dd, 1H); 4.20 (H, b), 4.48 (d, 1H); 4.56 (b, 1H), 5.90–6.05 (m, 2H); 6.65–6.30 (4H, m), 7.05–6.83 (2H, m)

Procedure for Product 109

1.25 g (139) are heated to reflux temperature in 10 mL thionyl chloride, the excess thionyl chloride is distilled off, the residue is absorbed in 40 mL water-free THF and added dropwise to a solution of 2.0 g (4) in 20 mL THF and stirred for 1 hour at reflux temperature. The reaction mixture is evaporated and the crude product is purified by column chromatography ($CHCl_3$/MeOH, 2–5%): 1.75 g (57% of the theoretical yield.) colorless foam (109).

$^1$H-NMR ($CDCl_3$; δ (ppm)): 1.65–1.85 (m, 4H), 1.98 (ddd, 1H); 2.25 (b, 2H); 2.67–2.58 (m, 3H); 2.75–2.71 (2H, m), 2.87 (H, dd), 3.05–3.35 (m, 5H); 3.55 (2H, m), 3.67–3.74 (2H, d), 3.80 (s, 3H); 3.85 (d, 1H); 4.10 (dd, 1H); 4.40 (d, 1H); 4.56 (b, 1H); 5.90–6.05 (m, 2H); 6.85 (s, 1H), 7.30 (5H, m)

Procedure for Product 108

1.0 g (144) are heated for 2 hours to reflux temperature in 10 mL thionyl chloride, the excess thionyl chloride is distilled off, the residue is absorbed in 20 mL water-free THF and added dropwise to a solution of 1.33 g (4) in 20 mL THF and stirred for 1 hour at room temperature. The reaction mixture is evaporated, absorbed in a $NaHCO_3$ solution and extracted with ether (3×40 mL). The ether phase is evaporated and the crude product is purified by column chromatography ($CHCl_3$/MeOH, 5%): 1.22 g (56% of the theoretical yield.) colorless foam (108).

$^1$H-NMR ($CDCl_3$; δ (ppm)): 1.63–1.80 (m,4H), 1.98 (ddd, 1H); 2.20 (b, 2H); 2.61–2.48 (m, 3H); 2.69–2.74 (2H, m), 2.90 (H, dd), 3.02–3.45 (m, 3H); 3.59 (2H, m), 3.60–3.72 (2H, d), 3.87 (s, 3H); 3.95 (d, 1H); 4.22 (dd, 1H); 4.45 (d, 1H); 4.76 (b, 1H); 5.68–6.00 (m, 2H); 6.95 (s, 1H), 7.10–7.42 (5H, m)

"Maritidinon-Type" 4,4a-dihydro-7-bromo-9-methoxy-3-oxo (3H,6H) (5,10b) ethanophenanthridine-10-ol (113)

A solution of 4.70 g (13.4 mmol) N-demethyl-bromonarwedine (15) and 2.35 g calcium chloride are heated to reflux for 3.5 hours in 200 mL 70% ethanol. The reaction mixture is subsequently rotated, the residue is absorbed in 80 mL 1 N hydrochloric acid and the product is precipitated with concentrated aqueous ammonia. After overnight cooling (+4° C.) the precipitate is sucked off and dried at 50° C./50 mbar. The aqueous phase is extracted three times with ethyl acetate, the combined organic phases are washed once with a saturated aqueous sodium chloride solution, dried ($Na_2SO_4$), filtered and evaporated, whereby 4.37 g (93% of the theoretical yield.) colorless crystals of 113 with a melting point of 185–190° C. are obtained.

DC: EtOAc: MeOH=8:2

$^1$H-NMR (DMSO-$d_6$; δ (ppm)): 1.95 (ddd, 1H, H-11); 2.15 (ddd, 1H, H-11'); 2.30 (dd, 1H, H-4, $J_{(4,4')}$=16.0 Hz); 2.65 (dd, 1H, H-4', $J_{(4,4')}$=16.0 Hz); 2.80 (ddd, 1H, H-12, $J_{(12,12')}$=15.1 Hz); 3.05 (ddd, 1H, H-12', $J_{(12,12')}$=15.1 Hz); 3.30 (dd, 1H, H-4a); 3.55 (d, 1H, H-6, $J_{(6,6')}$=16.9 Hz); 3.75 (s, 3H, O—$CH_3$); 3.90 (d, 1H, H-6', $J_{(6,6')}$=16.9 Hz); 5.80 (d, 1H, H-2, $J_{(1,2)}$=9.3 Hz); 7.00 (s, 1H, H-8); 7.90 (d, 1H, H-1, $J_{(1,2)}$=9.3 Hz)

$^{13}$C-NMR (DMSO-$d_6$; δ (ppm)): 38.0 (t, C-11); 39.8(t C-4); 42.8 (s, C-10b); 53.1 (t, C-12); 55.9 (t, C-6); 56.0 (q, $OCH_3$); 64.1 (d, C-4a); 109.6 (s, C-7); 113.6 (d, C-2); 123.2 (s, C-6a); 126.6 (d, C-8); 129.1 (s, C-10a); 142.9 (s, C-10); 147.5 (s, C-9); 155.3 (d, C-1); 197.4 (s, C-3)

35-4,4a-dihydro-7-bromo-9-methoxy-10-hydroxy (3H,6H) (5,10b) ethanophenanthridine-3-ol (114):

To a solution of 1.0 g (2.86 mmol) maritidinon-type (113) in 5 mL absolute tetrahydrofuran, 10 mL of a 1 N L-Selectrid-solution in tetrahydrofuran are added dropwise at 0° C.; it is then quickly heated to reflux. After 1.5 hours, hydrolyze at 0° C. with 10 mL tetrahydrofuran: water 1:1 and the tetrahydrofuran is spun off. The residue is absorbed in 80 mL 1 N hydrochloric acid, made basic with concentrated aqueous ammonia and extracted with ethyl acetate. The combined organic phases are washed with a saturated aqueous sodium chloride solution, dried ($Na_2SO_4$), filtered and evaporated, whereby quantitative yellow crystals of 114 with a melting point of 165–167° C. are obtained. DC: $CHCl_3$: MeOH=9:1.

114 and 3R-2,3,4,4a-tetrahydro-7-bromo-9-methoxy-10-hydroxy (1H,6H) (5,10b) ethanophenanthridine-10-ol (116)

To a solution of 1.0 g (0.29 mmol) maritidinon-type (113) in 1 mL absolute tetrahydrofuran, 1 mL of a 1 N L-Selectrid-solution in tetrahydrofuran is added dropwise and agitated at 0° C. After 1 hour, an additional 1 mL a 1 N L-Selectrid-solution in tetrahydrofuran is added dropwise and agitated for 2.5 hours at 0° C. and for 3.5 hours at room temperature. It is subsequently hydrolyzed with 2 mL of a 1:1 mixture of tetrahydrofuran and water, made basic with concentrated aqueous ammonia after agitation and extracted with ethyl acetate. The combined organic phases are washed with a saturated aqueous sodium chloride chromatography ($Na_2SO_4$), filtered and evaporated. The two products are separated by column chromatography (7 g silica gel, flow agent: $CHCl_3$: MeOH=8:2), yielding 30 mg (30% of the theoretical yield) colorless crystals of 114 and 20 mg (20% of the theoretical yield) of colorless crystals of 116.

DC: $CHCl_3$: MeOH=9:1

114:

$^1$H-NMR ($CDCl_3$; δ (ppm)): 1.50 (ddd, 1H, H4); 1.80 (ddd, 1H, H-11); 2.20 (ddd, 1H, H-11'); 2.45 (ddd, 1H, H-4'), 2.60–2.80 (m, 2H, H-4a/12); 3.30 (ddd, 1H, H-12'); 3.60 (d, 1H, H-6, $J_{(6,6')}$=17.8 Hz); 3.75 (s, 3H, $OCH_3$); 4.00 (d, 1H, H-6', $J_{(6,6')}$=17.8 Hz); 4.30 (dd, 1H, H-3); 5.55 (dd, 1H, H-2, $J_{(2,3)}$=9.8 Hz); 6.75 (dd, 1H, H-3, $J_{(2,3)}$=9.8 Hz); 6.80 (s, 1H, H-8)

$^{13}$C-NMR ($CDCl_3$; δ (ppm)): 26.9 (t, C-11); 35.7 (t, C-4); 37.7 (s, C-10b); 47.7 (t, C-12); 50.7 (t, C-6); 51.0 (q, $OCH_3$); 58.8 (d, C-4a); 62.8 (d, C-3); 105.3 (s, C-7); 107.4 (d, C-2); 118.3 (s, C-6a); 124.8 (d, C-8); 125.5 (s, C-10a); 127.4 (d, C-1); 137.9 (s, C-10); 141.3 (s, C-9)

116:

$^1$H-NMR ($CDCl_3$; δ (ppm)): 1.55–1.95 (m, 4H, H-1/1'/4/11); 2.15 (m, 1H, H-11'); 2.35 (m, 1H, H-2); 2.60 (dd, 1H, H-4'); 2.75–2.95 (m, 2H, H-4a/12); 3.15 (dd, 1H, H-2'); 3.40 (ddd, 1H, H-12'); 3.70 (d, 1H, H-6, $J_{(6,6')}$=6.2 Hz); 3.85 (d, 3H, $OCH_3$); 4.00 (d, 1H, H-6', $J_{(6,6')}$=6.2 Hz); 4.15 (ddd, 1H, H-3); 6.90 (s, 1H, H-8)

35-4,4a-dihydro-9-methoxy-10-hydroxy (3H,6H) (5,10(b) ethanophenanthridine-3-ol (115)

A solution of 1.0 g (2.84 mmol) maritidinon-type (114) and 2.0 g calcium chloride are treated in 50 mL 50% ethanol with 4.0 g freshly activated zinc powder and heated to reflux for 2 hours. Subsequently, the excess zinc is filtered off, washed with methanol and the residual solution is spun off. The residue is absorbed in 80 mL 1 N hydrochloric acid, made basic with concentrated aqueous ammonia and extracted with three times ethyl acetate. The combined organic phases are washed with a saturated aqueous sodium chloride solution, dried ($Na_2SO_4$, active carbon), filtered and evaporated, yielding 450 mg crude product which is cleaned by column chromatography (7 g silica gel, flow agent initially $CHCl_3$ : MeOH=8:2, then $CHCl_3$ : MeOH: $NH_4OH$=49.9: 49.9: 0.2), from which 270 mg (35% of the theoretical yield) red crystals of 115 are obtained, with a melting point of 59–60° C. are obtained.

DC: $CHCl_3$: MeOH=9:1

$^1$H-NMR (DMSO-$d_6$; δ (ppm)): 1.40 (ddd, 1H, H-4); 1.65 (ddd, 1H, H-11); 2.00 (ddd, 1H, H-11'); 2.20 (ddd, 1H, H-4'); 2.65 (dd, 1H, H-4a); 3.10 (ddd, 1H, H-12); 3.30–3.50 (m, 1H, H-12'); 3.45 (d, 1H, H-6, $J_{(6,6')}$=15.1 Hz); 3.75 (s, 3H, $OCH_3$); 4.05 (d, 1H, H-6', $J_{(6,6')}$=15.1 Hz); 4.20 (dd, 1H, H-3); 5.45 (d, 1H, H-2, $J_{(1,2)}$=8.9 Hz); 6.40 (d, 1H, H-1, $J_{(1,2)}$=8.9 Hz); 6.65–6.75 (m, 2H, H-7/8); 8.40 (b, 1H tauscht $D_2O$, Ph—OH)

$^{13}$C-NMR (DMSO-$d_6$; δ (ppm)): 32.2 (t, C-11); 41.1 (t, C-4); 42.7 (s, C-10b); 52.3 (t, C-12); 54.6 (t, C-6); 55.8 (q, $OCH_3$); 64.1 (d, C-4a); 67.1 (d, C-3); 109.4 (d, C-7); 115.8 (d, C-2); 124.9 (s, C-6a); 129.9 (s, C-10a); 130.2 (d, C-8); 132.5 (d, C-1); 143.7 (s, C-10); 146.0 (s, C-9)

[4aS-(4aα, 6B, 8aR*)]-4a,5,9,10,11,12-hexahydro=3-methoxy-11-methyl-1-nitro-6H-benzofuro[3a,3,2-ef][2]benzazepin-6-ol (117)

To a solution of 250 mg (0.87 mmol) galanthamine in 10 mL glacial acetic acid, a mixture of 0.5 mL smoking nitric acid and 2 mL glacial acetic acid is added dropwise at 15–20° C. After one hour of agitation at room temperature, additional 0.25 mL smoking nitric acid in 1 mL glacial acetic acid is added dropwise and agitated for 1 additional hour. Subsequently, it is poured on 80 mL water and made basic with a 40% sodium hydroxide solution. The aqueous phase is extracted three times with 30 mL each of ethyl acetate. The combined organic phases are washed once with saturated aqueous sodium chloride solution, dried ($Na_2SO_4$), filtered and evaporated, yielding 252 mg (87% of the theoretical yield.) yellow crystals of 117 with a melting point of 48–50° C.

DC: $CHCl_3$: MeOH=9:1

$^1$H-NMR ($CDCl_3$; δ (ppm)): 1.67 (ddd, 1H, H-9); 1.95–2.30 (m, 2H, H-5/9'); 2.20 (ddd, 1H, H-5'); 2.44 (s, 3H. $NCH_3$); 2.91 (ddd, 1H, H-10); 3.18 (ddd, 1H, H-10'); 3.87 (s, 3H, $OCH_3$); 4.01 (d, 1H, H-12); 4.16 (dd, 1H, H-6); 4.32 (d, 1H, H-12'); 4.68 (b, 1H, H-4a); 6.04 (dd, 1H, H-8); 6.16 (d, 1H, H-7); 7.35 (s, 1H, H-2)

$^{13}$C-NMR ($CDCl_3$; δ (ppm)): 29.6 (t, C-5); 33.3 (t, C-9); 43.6 (q, $NCH_3$); 48.5 (s, C-8a); 53.4 (t, C-10); 54.4 (t, C-12); 56.1 (q, $OCH_3$); 61.4 (d, C-6); 89.6 (s, C-4a); 108.9 (d, C-8); 126.5 (,); 126.9 (,); 128.3 (d, C-7); 134.8 (,); 143.0 (,); 143.4 (,); 149.8 (,)

[4aS-(4aα, 6β, 8aR*)]-4a.5,9,10,11,12-Hexahydro-1-amino-3-methoxy-11-methyl-6H-benzofuro[3a,3,2-ef][2]benzazepin-6-ol (118):

To a solution of 200 mg (0.60 mmol) 117 in 10 mL methanol a solution of 420 mg (2.4 mmol) sodium dithionite in 10 mL water is added dropwise at room temperature and agitated for 1 hour. The methanol is subsequently spun out, the residue is absorbed in 50 mL water, made basic with concentrated aqueous ammonia and extracted five times with 30 mL each of trichloromethane. The combined organic phases are washed once with saturated aqueous sodium chloride solution, dried ($Na_2SO_4$), filtered and evaporated, yielding 148 mg (82% of the theoretical yield.) yellow crystals of 118 with a melting point of 151–153° C.

DC: $CHCl_3$:MeOH=9:1

$^1$H-NMR ($CDCl_3$; δ (ppm)): 1.59 (ddd, 1H, H-9); 1.90–2.10 (m, 2H, H-5/9'); 2.43 (s, 3H, $NCH_3$); 2.62 (ddd, 1H, H-5'); 2.96 (ddd, 1H, H-10); 3.20 (ddd, 1H, H-10'); 3.70 (d, 1H, H-12); 3.79 (s, 3H, $OCH_3$); 4.10 (d, 1H, H-12'); 4.52 (b, 1H, H-4a); 5.98 (dd, 1H, H-8); 6.08 (d, 1H, H-7); 6.16 (s, 1H, H-2)

New, substituted, bridged-over bases:

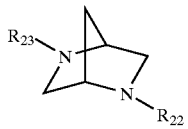

| Substance No. | J-No. | $R_{23}$ | $R_{23}$ |
|---|---|---|---|
| 120 | | Benzyl | p-Nitro-phenyl- |
| 121 | | Benzyl | p-Amino-phenyl |
| 122 | | Benzyl | p-Chlorphenyl |
| 123 | | Benzyl | p-Hydroxyphenyl |
| 124 | | Benzyl | o-Nitrophenyl |
| 125 | | Benzyl | o-Aminophenyl |
| 126 | | Benzyl | o-Chlorphenyl |
| 127 | | Benzyl | o-Dimethylaminophenyl |
| 128 | | p-Ts | Phenyl |
| 129 | | H | Phenyl |
| 130 | | p-Ts | p-Methylphenyl |

-continued

New, substituted, bridged-over bases:

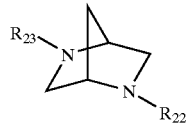

| Substance No. | J-No. | $R_{23}$ | $R_{23}$ |
|---|---|---|---|
| 131 | | H | p-Methylphenyl |
| 132 | | p-Ts | p-Chlorphenyl |
| 133 | | H | p-Chlorphenyl |
| 134 | | p-Ts | p-Fluorphenyl |
| 135 | | H | p-Fluorphenyl |
| 136 | | —$CH_2$—$CH_2$—$CH_2$—Cl | Phenyl |
| 137 | | —$CH_2$—$CH_2$—Cl | p-Fluorphenyl |
| 138 | | —$CH_2$—$CH_2$—OH | t-BOC |
| 139 | | —$CH_2$—$CH_2$—OH | Benzyl |
| 140 | | —$CH_2$—CN | Benzyl |
| 141 | | —$CH_2$—$CH_2$—$NH_2$ | Benzyl |
| 142 | | —$CH_2$—$CH_2$—CN | Benzyl |
| 143 | | —$(CH_2)_3$—$NH_2$ | Benzyl |
| 144 | | —$CH_2$—COOEt | Benzyl |
| 145 | | t-BOC | —$CH(Ph)_2$ |

5-Benzyl-2-(4-nitophenyl)-2,5-diazabicyclo[2.2.1] heptane (120)

To a solution of 5.30 g 2-benzyl-2,5-diazabicyclo[2.2.1] heptane×2 HBr in 20 mL anhydrous DMSO, 3.97 dried, fine ground $K_2CO_3$ and 2.03 g 4-nitrobenzene fluoride were added. It was then agitated magnetically at 80° C. for 3 hours, poured on 100 mL water, the precipitated crystals were sucked off, washed with diisopropyl ether and dried in vacuum: 4.10 g (120) as colorless crystals (92% of the theoretical yield.), melting point 170–173° C. DC: toluene/acetone (1:1) or $CHCl_3$.

$^1$H-NMR ($CDCl_3$): 8.10 (2H, d), 7.35–7.2 (5H, m), 6.45 (2H, d), 4.40 (1H, m), 3.75 (2H, s), 3.65 (1H, b), 3.45 (2H, dd), 2.95, 2.30 (2H, dd), 2.10, 1.85 (2H, dd)

$^{13}$C-NMR ($CDCl_3$): 151.14, 139.01, 136.55, 128.26, 126.97, 126.35, 110.42, 60.42, 58.28, 58.191, 53.17, 35.78.

5-Benzyl-2-(4-aminophenyl)-2,5-diazabicyclo[2.2.1] heptane (121)

4.1 g (120) in 360 mL ethanol and 20 mL water with 5 g $NH_4Cl$ and 7 iron powder were heated to reflux temperature under 4 hours of mechanical agitation. The reaction solution is filtered over Celite and active carbon, evaporated, absorbed in 100 mL water, brought to pH 10 with $K_2CO_3$ and extracted with ether (4×50 mL). The combined organic phases were dried with $Na_2SO_4$, evaporated and distilled in a bulb tube (Kp: 5 mBar; 160–170° C.): 3.0 g (81% of the theoretical yield.) (121) as colorless oil.

DC: $CHCl_3$/methanol (9:1).

$^1$H-NMR ($CDCl_3$): 7.35–7.15 (5H, m), 6.65 (2H, d), 6.45 (2H, d), 4.15 (1H, m), 3.70 (2H, s), 3.50 (H, m) 3.40, 3.30 (2H, dd), 3.20 (2H, b), 2.90, 2.70 (2H, dd), 2.05–1.85 (2H, dd)

5-Benzyl-2-(4-chlorophenyl)-2,5-diazabicyclo[2.2.1] heptane (122)

1.5 g (121) were dissolved in 20 mL concentrated HCl and added dropwise at 0–5° C. to a solution of 0.38 g $NaNO_2$ in 3 mL water, so that the temperature remained under 5° C. The solution was the added dropwise to a solution produced from 1.61 g CuSO$_3$×5 H$_2$O, 0.41 g NaCl, 0.39 g NaHSO$_3$ and 0.23 g NaOH and CuCl in 10 mL HCl and heated for 4 hours to 50° C. It was then poured on 100 mL water, made alkaline with K$_2$CO$_3$ and extracted with ether (5×100 mL). Concentration by evaporation and bulb tube distillation (Kp: 5 mbar; 135° C.) yielded 0.6 g(37% of the theoretical yield.) (122) as a colorless oil.

DC: CHCl$_3$/methanol (9:1).

$^1$H-NMR (CDCl$_3$): 7.40–7.15 (7H, m), 6.90–6.50 (2H, m), 4.25 (1H, m), 3.70 (2H, s), 3.60–3.45 (H, m), 3.45–3.30 (2H, m), 2.95, 2.70 (2H, dd), 2.10–1.80 (2H, m).

5-Benzyl-2-(4-hydroxyphenyl)-2,5-diazabicyclo [2.2.1]heptane (123)

To a solution of 1.17 g (122) in 17 mL concentrated HCl 0.35 g NaNO$_2$ in 5 mL water were added slowly dropwise, so that the temperature remained below 5° C. The solution was agitated for 2 hours at 60° C., neutralized with NaHSO$_3$ and extracted with ether (4×50 mL). The combined organic phases were dried with Na$_2$SO$_4$, evaporated and distilled in a bulb tube (Kp: 0.05 mbar; 140° C.): 0.1 g (123) (123) as colorless oil. DC: CHCl$_3$/methanol (9:1).

$^1$H-NMR (CDCl$_3$): 7.50–7.00 (8 H, m), 6.85–6.40 (2H, m), 4.25 (11H, m), 3.80–3.30 (5H, m), 3.05–2.65 (2H, m), 2.05, 1.90 (2H, dd).

5-Benzyl-2-(2-nitrophenyl)-2,5-diazabicyclo[2.2.1] heptane (124)

To a solution of 22.3 g 2-benzyl-2,5-diazabicyclo[2.2.1] heptane ×2 HBr in 110 mL anhydrous DMSO, 17.6 g dried, finely ground K$_2$CO$_3$ and 9.0 g 2-nitrobenzene fluoride were added. It was then agitated magnetically at 80° C. for 3 hours, poured on 300 mL water, the precipitated crystals were sucked off, washed with diisopropyl ether and dried in vacuum: 19.1 g (124) as colorless crystals (96.9% of the theoretical yield.), melting point 107–108° C.

DC: toulene/acetone (1:1) or CHCl$_3$.

$^1$H-NMR (CDCl$_3$): 7.75 (H, d), 7.35 (H, d), 7.30–7.15 (5H, m), 6.85–6.70 (2H, m), 4.30 (H, m), 3.65 (2H, s), 3.55 (2H, m), 2.90 (2H, dd), 2.85 (H, m), 2.00 (2H, dd).

5-Benzyl-2-(2-aminophenyl)-2,5-diazabicyclo[2.2.1] heptane (125)

5.0 g (124) in 360 mL ethanol and 20 mL water with 4 g NH$_4$Cl and 6.7 iron powder were heated to reflux temperature under 4 hours of mechanical agitation. The reaction solution is filtered over Celite and active carbon, evaporated, absorbed in 100 mL water, brought to pH 10 by means of K$_2$CO$_3$ and extracted with ether (4×50 mL). The combined organic phases were dried with Na$_2$SO$_4$, evaporated and distilled in a bulb tube (Kp: 5 mbar; 160–170° C.): 2.20 g (48.8% of the theoretical yield.) (125) as colorless oil. DC: CHCl$_3$/methanol (9:1).

$^1$H-NMR (CDCl$_3$): 7.45–7.20 (5H, m), 7.05–6.65 (4H, m), 3.95–3.65 (5H, m), 3.60–3.40 (2H, m),3.20–3.00 (H, m), 2.95–2.75 (2H, m), 2.00–1.85 (2H, m).

5-Benzyl-2-(2-chlorophenyl)-2,5-diazabicyclo[2.2.1] heptane (126)

Procedure analogous to (122).

Yield after bulb tube distillation (Kp: 5 mbar, 135° C.): 0.60 g (37.5% of the theoretical yield.) (126) as colorless oil.

DC: CHCl$_3$/methanol (9:1).

$^1$H-NMR (CDCl$_3$): 7.50–7.20 (6H, m), 6.85–6.55 (3H, m), 4.25 (H, m), 3.85–3.70 (2H, s), 3.65–3.50 (H, b), 3.45–3.30 (2H, m), 3.00, 2.75 (2H, dd), 2.15–1.80 (2H, m)

5-Benzyl-2-(2-dimethylaminophenyl)-2,5-diazabicyclo[2.2.1]heptane (127)

5-Benzyl-2-(2-methylaminophenyl)-2,5-diazabicyclo [2.2.1]heptane (127a)

0.95 g (125) with 0.5 g PO(OMe)$_3$ were heated for 3 hours to 160–180° C., cooled, hydrolyzed with 5 mL 30% NaOH, 10 mL water were added, and them extracted with ether (3×10 mL). Concentration by evaporation and color chromatography (CHCl$_3$/methanol 3%) yielded 0.15 g colorless oil (127-a) (15.6% of the theoretical yield.) and 0.09 g colorless oil (107) (8.5% of the theoretical yield.).

$^1$H-NMR (CDCl$_3$) (127-b): 7.45–7.20 (5H, m), 7.10–6.95 (2H, t), 6.80–6.00 (2H, dd), 3.90–3.65 (4H, m), 3.65–3.40 (2H, dd), 3.50–2.60 (6H, m), 2.0–1.80 (2H, m)

$^1$H-NMR (CDCl$_3$) (127): 7.40–7.20 (5H, m), 6.70–6.55 (3H, m), 6.40 (H, m), 3.75 (2H, s), −3.80–3.65 (H, m), 3.60–3.55 (2H, dd), 3.45–3.20 (3H, m), 2.90–2.75 (6H, s,s,), 2.30–2.15 (2H, dd).

Production of phenyl-substituted 2.5-diazabicyclo [2.2.1] heptane

| No. | Yield | Melting Point/Kp | DC | Method |
|---|---|---|---|---|
| 128 | 62.5% | 139–143° C. | Petrolether/EtOAc (7:3) | A |
| 129 | 71% | 0.05 mbar/120–130° | DC: CHCl$_3$/Methanol (9:1) | B |
| 130 | 46% | 149–151° C. | DC: Petrolether/EtOAc (7:3) | A |
| 131 | 65% | 0.05 mbar/ 130–140° C. | DC: CHCl$_3$/Methanol (9:1) | B |
| 132 | 69% | 214–217° C. | DC: Petrolether/EtOAc (7:3) | A |
| 133 | 56% | 0.05 mbar/ 120–130° C. | DC: CHCl$_3$/Methanol (9:1) | B |
| 134 | 55% | Melting 180–184° C. Point: | DC: Petrolether/EtOAc (7:3) | A |
| 135 | 74% | 0.05 mbar/ 120–130° C. | DC: CHCl$_3$/Methanol (9:1) | B |

Method (A) for cyclization of tritosyl-4-hydroxyprolinol 20 g (35 mmol) tritosyl-4-hydroxyprolinol with 75 mL toluene, 9.8 g (100 mmol) triethylamine and 35 mmol of the theoretical yielde appropriately substituted aniline (freshly distilled or uncrystallized) are heated in a steel autoclave for 3 hours to 160–170° C. After cooling and opening of the theoretical yielde autoclave, the product is rinsed out from the autoclave with 100 mL toluene, shaken once with 100 m; NaCl solution and once with 100 NaHCO$_3$, and the organic phase is dried by means Na$_2$SO$_4$ and evaporated. The crystalline product is digested with isopropyl; filtered oil.

Method (B) for Splitting Off the p-Ts Protective Group 2.5 g educt in 40 mL glacial acetic acid and 20 mL concentrated sulfuric acid are agitated for 2 hours at 80° C. Subsequently, it is poured on 200 mL ice/water, extracted with EtOAc (2 times 100 mL) EtOAc phase is discarded), the aqueous phase is treated with 30% NaOH to ph 12 and extracted with EtOAc (6×50 mL). The Ethyl acetate phase is evaporated and bulb-tube distilled: colorless oil.

NMR Spectra

5-Phenyl-2-p-tosyl-2,5-diazabicyclo[2.2.1]heptane (128)

$^1$H-NMR (CDCl$_3$): 7.68 (2H, d), 7.29 (2H, d), 7.18 (2H, m), 6.72 (H, t), 6.4 (2H, dd), 4.51 (H, b) 4.32 (H, b), 3.52 (2H, dd), 3.24 (2H, dd), 2.42 (3H, s), 1.86 (H, d), 1.40 (H, d).

$^{13}$C-NMR (CDCl$_3$): 146.18, 143.49, 135.27, 129.66, 129.10, 127.18, 116.84, 112.39, 59.98, 56.52, 52.25, 36.50, 21.37.

2-Phenyl-2,5-diazabicyclo[2.2.1]heptane (129)

$^1$H-NMR (CDCl$_3$): 7.23 (2H, m), 6.71 (3H, m), 4.30 (H, b), 3.78 (H, b), 3.66 (H, dd), 3.18–2.89 (3H, m), 2.06–1.78 (3H, m).

$^{13}$C-NMR (CDCl$_3$): 146.92, 129.09, 116.08, 112.41, 59.78, 56.62, 56.22, 49.65, 37.18

5-(4-Methylphenyl)-2-p-tosyl-2,5-diazabicyclo [2.2.1]heptane (130)

$^1$H-NMR (CDCl$_3$): 7.68 (2H, d), 7.27 (2H, d), 7.00 (2H, d), 6.36 (2H, d), 4.49 (H, s), 4.25 (H, s), 3.53 (H, d), 3.46 (H, dd), 3.26 (H, dd), 3.17 (H, d), 2.41 (3H, s), 2.24 (3H, s), 1.83 (H, d),1.38(H, d).

$^{13}$C-NMR (CDCl$_3$): 144.09, 143.44, 135.35, 129.63, 127.30, 125.96, 112.55, 60.02, 57.06, 56.73, 51.99, 36.46, 21.36, 20.16.

2-(4-Methylphenyl)-2,5-diazabicyclo[2.2.1]heptane (131)

$^1$H-NMR (CDCl$_3$): 7.05 (2H, d), 6.48 (2H, d), 4.25 (H,s), 3.77 (H,s), 3.68 (H,dd), 3.16 (H,dd) 3.02 (H, dd), 2.92 (H, dd), 2.24 (3H, s), 1.95 (H, d), 1.82 (H, b), 1.80, (H,d).

5-(4-Chlorophenyl)-2-p-tosyl-2,5-diazabicyclo [2.2.1]heptane (132)

$^1$H-NMR (CDCl$_3$): 7.52 (2H, d), 7.13 (2H, d), 6.96 (2H, d), 6.22 (2H, d), 4.38 (H, s), 4.12 (H, s), 3.40–3.29 (2H, m), 3.12 (H, dd), 3.03 (H, dd), 2.30 (3H, s), 1.73 (H, d), 1.28 (H, d).

$^{13}$C-NMR (CDCl$_3$/DMSO): 144.70, 143.30, 134.58, 129.44, 128.40, 126.77, 120.58, 113.34, 59.60, 56.73, 56.44, 51.81, 36.09, 21.00

2-(4-Chlorophenyl)-2,5-diazabicyclo[2.2.1]heptane (133)

$^1$H-NMR (CDCl$_3$): 7.14 (2H, d), 6.45 (2H, d), 4.23 (H, s), 3.76 (H, s), 3.62 (H, d), 3.08 (H, d), 3.00 (H, d), 2.89 (H, d), 1.92 (H, d), 1.81 (H, d), 1.56 (H, b).

$^{13}$C-NMR (CDCl$_3$): 145.53, 128.78, 120.56, 113.44, 59.77, 56.83, 56.19, 49.50, 37.26

5-(4-fluorophenyl)-2-p-tosyl-2,5-diazabicyclo[2.2.1] heptane (134)

$^1$H-NMR (CDCl$_3$): 7.68 (2H, d), 7.27 (2H, d), 6.82–6.95 (2H, m), 6.40–6.29 (2H, m), 4.49 (H, s), 4.23 (H, s), 3.52 (H, d), 3.46 (H, dd), 3.25 (H, dd), 3.13 (H, d) 2.41 (3H, s), 1.86 (H, d), 1.41 (H, d).

$^{13}$C-NMR (CDCl$_3$): 157.63, 152.96, 143.56, 142.80, 142.77, 135.21, 129.65, 127.17, 115.73, 115.29, 113.20, 113.05, 59.97, 57.35, 56.93, 51.79, 36.60, 21.34.

5-(4-fluorophenyl)-2,5-diazabicyclo[2.2.1]heptane (135)

$^1$H-NMR (CDCl$_3$): 7.05–6.83 (2H, m ), 6.52–6.28 (2H, m), 4.20 (H, s), 3.76 (H, s) 3.64 (H, dd), 3.10 (H, d), 3.00 (H, dd), 2.88 (H, d), 1.96 (H, d), 1.81 (H, d), 1.76 (H, b).

$^{13}$C-NMR (CDCl$_3$): 157.27, 152.63, 143.61, 115.67, 115.32, 113.13, 112.98, 60.21, 57.04, 56.27, 49.21, 37.29.

5(3-Chloropropyl)-2-phenyl-2,5-diazabicyclo[2.2.1] heptane (136)

129 (1.0 g, 5.7 mmoles), 0.23 g (5.7 mmoles) of sodium amide and 20 mL of toluene are refluxed for 1 hour. After that, 0.93 g (5.7 mmoles) of 1-bromo-3-chloropropane in 10 mL of toluene are added dropwise over a period of 20 minutes and refluxed for 2 hours. After cooling, the reaction mixture is extracted with 2N HCl (2×50 mL) and the aqueous phase made alkaline with 30% sodium hydroxide and extracted with toluene (3×40 mL). Evaporation and bulb tube evaporation (boiling point at 0.05 mbar: 120°–130° C.) resulted in 0.97 g (70.4% of the theoretical yield) of 136 as a colorless oil.

TLC: chloroform: MeOH=9:1

$^1$H-NMR (CDCl$_3$): 7.19 (2H, m) 6.69 (3H, m), 4.27 (H, b), 3.68 (H, b), 3.60 (H, dd), 3.18–2.89 (5H, m), 2.36–1.36 (7H, m).

5-(2-Chloroethyl)-2-(4-fluorophenyl)-2,5-diazabicyclo[2.2.1]heptane (137)

135 (1.0 g, 5.2 mmoles), 0.21 g (5.3 mmoles) of sodium amide and 20 mL of toluene are refluxed for 1 hour. After that, 0.77 g (5.2 mmoles) of 1-bromo-3-chloroethane in 10 mL of toluene are added dropwise over a period of 20 minutes and refluxed for 2 hours. After cooling, the reaction mixture is extracted with 2N HCl (2×50 mL) and the aqueous phase made alkaline with 30% sodium hydroxide and extracted with toluene (3×40 mL). Evaporation and bulb tube evaporation (boiling point at 0.05 mbar: 100° -120° C.) resulted in 0.76 g (56.7% of the theoretical yield) of 137 as a colorless oil.

TLC: chloroform: MeOH=9:1

$^1$H-NMR (CDCl$_3$): $^1$H-NMR (CDCl$_3$): 7.05–6.83 (2H, m), 6.52–6.28 (2H, m), 4.20 (H, s), 3.76 (H, s), 3.64 (H, dd), 3.10 (H, d), 3.00 (H, dd), 2.88 (H, d), 2.66–2.28 (2H, m), 2.20–1.90 (2H, m) 1.96 (H, d), 1.81 (H, d), 1.76 (H, b).

2-t-Boc-5-(2-Hydroxyethyl)-2,5-diazabicyclo[2.2.1] heptane (138)

Gaseous ethylene oxide is introduced slowly for 1.5 hours at 20° C. and with stirring into a solution of 2.5 g of 2-t-Boc-2,5-diazabicyclo[2.2.1]heptane in 50 mL of methanol, the temperature increasing to 35° C. The solution was evaporated and the oily crude product distilled using a bulb tube (boiling point 0.05 mbar, 90°–100° C.); 1.60 g of 138 as a colorless oil (52.5% of the theoretical yield).

$^1$H-NMR (CDCl$_3$): 4.31 (H, d), 3.54 (2H, t), 3.40 (H, d), 3.18 (H, dd), 2.92 (H, dd), 2.73 (2H, m), 2.56 (H, d), 1.84 (H, d), 1.72 (H, d), 1.54 (9H, s)

$^{13}$C-NMR (CDCl$_3$): 157.80, 79.21, 61.76, 61.24, 59.82, 59.68, 56.40, 56.09, 55.73, 55.43, 49.95, 49.21, 36.01, 35.36, 28.27

2-Benzyl-5-(2-hydroxyethyl)-2,5-diazabicyclo[2.2.1]heptane (139)

Procedure: See 138

Yield: 83.3% of the theoretical yield of 139, as a colorless oil with a boiling point of 120°–130° C. at 0.005 mbar.

$^1$H-NMR (CDCl$_3$): 7.30 (5H, m), 3.67–3.74 (2H, d), 3.55 (2H, m), 3.30 (2H, b), 3.20 (H, b), 2.87 (H, dd), 2.75 (H, dd), 2.71 (H, t), 2.67 (2H, m), 1.78 (H, m), 1.68 (H, m).

$^{13}$C-NMR (CDCl$_3$): 139.63, 128.29, 128.09, 126.65, 62.49, 61.16, 59.80, 58.19, 56.45, 56.26, 56.19, 33.64

2-Benzyl-5-cyanomethyl-2,5-diazabicyclo[2.2.1]heptane (140)

Finely ground potassium carbonate, as well as 1.3 mL of freshly distilled chloroacetonitrile were added to a solution of 3 g of 2-benzyl-2,5-diazabicyclo[2.2.1]heptane in 40 mL of anhydrous toluene and refluxed for 10 hours with vigorous stirring. The solution was cooled, filtered and evaporated. Bulb tube distillation (boiling point: 110°–120° C. at 0.01 mbar) resulted in 3.57 g of 140 as a colorless oil (97% of the theoretical yield).

$^1$H-NMR (CDCl$_3$): 7.41–7.18 (5H, m), 3.65, 3.75 (2H, d), 3.53, 3.46 (2H, d), 3.45 (H, b), 3.37 (H, b), 3.04 (H, d), 2.73 (H, d), 2.71 (H, dd), 2.68 (H, d), 1.82 (H, d), 1.77 (H, d).

$^{13}$C-NMR (CDCl$_3$): 139.41, 128.08, 127.92, 126.51, 117.03, 62.47, 61.39, 57.97, 57.09, 55.97, 41.23, 33.00.

2-Benzyl-5-(2-aminoethyl)-2,5-diazabicyclo[2.2.1]heptane (141)

A solution of 5.74 g (25.3 mmoles) of 140 and 50 mL of NH$_3$ were hydrogenated with 2 g of Raney nickel in a steel autoclave at 100 bar H$_2$ and 100° C. for 2 hours. The catalyst was filtered off with suction and the solution was evaporated and distilled using a bulb tube (boiling point: 135°–145° C. at 0.01 mbar): 5.02 g of 141 as a colorless oil (87% of the theoretical yield).

$^1$H-NMR (CDCl$_3$): 7.18 (5H, m), 3.70 (2H, d), 3.23 (2H, b), 2.69–2.42 (8H, m), 1.71 (H, ddd), 1.65 (H, ddd), 1.70 (2H, b).

$^{13}$C-NMR (CDCl$_3$): 139.62, 127.92, 127.65, 126.19, 62.15, 61.15, 57.92, 57.30, 56.19, 55.91, 40.80, 33.32

2-Benzyl-5-cyanoethyl-2,5-diazabicyclo[2.2.1]heptane (142)

Freshly distilled acrylonitrile (2.5 g) is added to a solution of 3 g of 2-benzyl-2,5-diazabicyclo [2.2.1]heptane in 40 mL of anhydrous toluene and refluxed with vigorous stirring. The solution was cooled, filtered and evaporated. Bulb tube distillation (boiling point: 120°–130° C. at 0.01 mbar) resulted in 3.43 g of 142 as a colorless oil (88% of the theoretical yield).

$^1$H-NMR (CDCl$_3$):7.39–7.17 (5H, m), 3.70 (2H, d), 3.30 (H, b), 3.26 (H, b), 2.88–2.59 (4H, m), 2.74 (H, d) 2.63 (H, dd), 2.42 (2H, t), 1.75 (H, dd), 1.64 (H, dd).

$^{13}$C-NMR (CDCl$_3$): 139.50, 128.17, 127.99, 126.57, 118.64, 62.40, 61.15, 58.68, 56.59, 55.91, 49.77, 33.66, 18.21

2-Benzyl-5-(2-aminopropyl)-2,5-diazabicyclo[2.2.1]heptane (143)

Analog: Similar to 141

Yield: 83.7% of the theoretical, colorless oil, boiling point: 120°–130° C. at 0.01 mbar $^1$H-NMR (CDCl$_3$): 7.18 (5H, m), 3.70 (2H, d), 3.31 (H, b), 3.16 (H, b), 2.91–2.48 (8H, m), 2.22 (2H, b), 1.71 (2H, m), 162 (H, d), 1.49 (H, d)

$^{13}$C-NMR (CDCl$_3$): 139.46, 127.76, 127.54, 126.03, 61.55, 60.90, 57.76, 56.08, 55.32, 51.58, 39.99, 33.05, 31.97

Ethyl 2-(5-benzyl-2,5-diazabicyclo[2.2.1]heptane)-acetate (144)

Ethyl bromoacetate (2.5 g) and 3 g of dried, finely ground potassium carbonate are added to a solution of 3 g of 2-benzyl-2,5-diazabicyclo[2.2.1]heptane in 40 mL of toluene and refluxed for 8 hours with vigorous stirring. The solution was cooled, filtered and concentrated. Bulb tube distillation (boiling point: 125°–130° C. at 0.01 mbar) resulted in 1.79 g of 144 as a colorless oil (40% of the theoretical yield).

$^{13}$C-NMR (CDCl$_3$): 170.96, 139.44, 128.14, 128.03, 126.62, 62.31, 61.64, 60.36, 58.06, 56.90, 55.47, 55.33, 33.74, 14.03

2-tBoc-5-diphenylmethyl-2,5-diazabicyclo[2.2.1]heptane (145)

Triethylamine (0.8 g) and 1.55 g of diphenylmethyl chloride are added to a solution of 1.5 g of 2-tBoc-2,5-diazabicyclo[2.2.1]heptane in anhydrous THF and refluxed with stirring for 4 hours. The THF was then evaporated off, taken up in 50 mL of saturated sodium hydrogen carbonate solution and extracted 3 times with 30 mL of ether. Evaporation resulted in 2.2 g of yellowish crystals of 145 (78% of the theoretical yield).

$^1$H-NMR (CDCl$_3$): 7.48–7.11 (10 H, m), 4.81 (H, b), 4.31 (H, d), 3.40 (H, d), 3.18 (H, dd), 2.92 (H, dd), 2.56 (H, d), 1.84 (H, d), 1.72 (H, d), 1.54 (9H, s)

Literature List (1) S. Y. Han, J. E. Sweeney, E. S. Bachman, E. J. Schweiger, J. T. Coyle, B. M. Davis, M. M. Joullie, Eur. J. Med. Chem. 27, 673–687 (1992)

(2) T. Kametani, K. Yamaki, S. Yaki, K. Fukumoto, J. Chem. Soc. (C), 2602 (1969)

(3) T. Kametani, K. Shishido, E. Hayashi, J. Org. Chem., 36, 1259 (1971)

(4) T. Kametani, C. Seino, K. Yamaki, S. Shibuya, K. Fukumoto, J. Chem. Soc., 1043–1047 (1971)

(5) T. Kametani, K. Yamaki, T. Terui, S. Shibuya, K. Fukumoto, J. Chem. Soc. Perkin I, 1513–1516 (1972)

(6) T. Kametani, K. Yamaki, T. Terui, J. Het. Chem. 10, 35–37 (1973)

(7) J. Szewczyk, A. Lewin, F. I. Caroll, J. Het. Chem 25, 1809–1811 (1988)

(8) R Vlahov, D. Krikorian, G. Spassov, M. Chinova, I. Vlahov, G. Parushev, G. Snatzke, L. Ernst, K. Kieslich, W. Abraham, W. Shedrick, Tetrahedron 45, 3329 (1989)

(9) P. Strehlke, G. A. Hoyer, E. Schröder, E. Arch. Pharm. 388 (2), 94–109 (1975)

(10) M. Ishizaki, K. Ozaki, A. Kanematsu, T. Isoda, O. Hoshino, J. Org. Chem. 58, 3877–3885 (1993)

(11) C. Nogueiras, W. Döpke, G. Lehmann, tetrahedron Letters 35, 3249–3250 (1971)

(12) H. H. Wassermann, R. J. Gambale, Tertrahedron 48 (35), 7059–7070 (1992)

(13) J. M. Pons, A Pommier, J. Lerpiniere, P. Kocienski, J. Chem. Soc., Perkin Trans I 14, 1549–1551 (1993)

(14) T. Kioshi, Yakugaku Zhassi, 104, 1009 (1984)

(15) B. M. Davsis, Pat WO 88/08708 A1 (1988)

(16) Stichting Biomed. Res., Pat NL 88000350 A1 (1989)
(17) J. Bastida; F. Viladomat; J. M. Llabres, S. Quiroga, C. Codina, M. Rubiralta, Planta Med. 56, 123, 1990
(18) S. J. Han, S. C. Mayer, E. J. Schweiger, B. M. Davis, M. M. Joullie, Boorg. Med. Chem. Lett. 1, 579, 1991
(19) D. Albrigt, N. Goldman, Pat. 64219 (1968)
(20) H. G. Boit, W. Döpke, A. W. Beitner, Chem. Ber. 90, 2197 (1957)
(21) R. Matusch, M. Kreh, U. Müller, Helv. Chim. Acta 77, 1611 (1994)
(22) H. M. Fales, L. D. Gioffrida, W. C. Wildman, J.Am. Chem. Soc. 78, 4145 (1956)
(23) S. Kobayashi, K. Satoh, S. Numata.; T. Hingu, M. Kihara, Phytochemistry 30, 675 (1991)
(24) R. W. Kosley, L. Davis, V. Taberna, Pat. EP 653427 A1 (1995), US 93-137440
(25) R. W. Kosley, L. Davis, V. Taberna, Pat. EP 649846 A1 (1995), US 93-137444
(26) R. W. Kosley, L. Davis, V. Taberna, Pat. EP 648771 A1 (1995), US 93-137443
(27) W. S. K. Kaisha, EP 393400 (1990), JP 82321 (1989), JP 238064 (1989)
(28) D. L. Romero e.y., Pat WO 91–09849 (1991), US 90–07390 (1990)
(29) J. E. Arrowsmith, Pat. EP 324543 (1989), GB 8800694 (1988)
(30) D. G. Hutchinson, Pat. WO 9323384 (1993), US 92-880432 (1992)
(31) P. S. Portoghese, A. A. Mikhail, J. Org. Chem. 31, 1059 (1966)
(32) T. F. Braish, D. E. Fox, J. Org. Chem., 55, 1684–1687 (1990)
(33) S. Ziklova, K. Ninov, Tr. Nauchniozsled. Khim. Farm. Inst. 12, 35–46 (1982)
(34) K. Fujii, K. Tomino, H. Watanabe, J. Pharm. Soc. Japan 74, 1049–51 (1954)
(35) H. G. Morren, R. Danayer, R. Linz, J. Mathieu, H. Strubbe, S. Trolin, Ind. Chim. Belge 22, 409–416 (1957)
(36) D. C. Jones, M. A. Wirter, K. S. Hirsch, N. Stamm, H. M. Taylor, J. Med. Chem. 33 (1), 416–429 (1990)
(37) G. L. Regnier, C. G. Guillonneau, J. L. Duhault, F. P. Tisserand, G. Saint-Romas, S. M. Holstorp, Eur. J. Med. Chem 22, 243–250 (1987)
(38) G. E. Martin e.a., J. Med. Chem. 32, 1056 (1989)
(39) Z. Budai, Hpat. HU 61737 (1991)
(40) D. W. Smith, Pat. EP 345808 (1988), US 204845 (1988), US 338253 (1989)
(41) J. P. Yevich, EP 400661 (1990), US 360657 (1989), US 503197 (1990)
(42) T. F. Braish, Pat. EP 397351 (1990), US 350423 (1989), US 423063 (1989)
(43) am 15, Oktober 1995 bekaantgemachte österr. Patentanmeldung 1980/94 vom Oct. 21, 1994.
(44) G. L. Ellmanm, K. D. Courtney, V. Andres, R. M. Fetherstone, Biochem. Pharmacol. 7, 88 (1961). Sanochemia Ltd. 1996.04.19 vertreten durch:

What is claimed is:
1. A compound of formula (1)

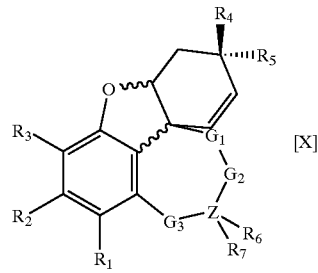

Formula (I)

in which $R_1$, $R_2$ either are the same or different and represent
hydrogen, F, Cl, Br, I, CN, NC, OH, SH, $NO_2$, $SO_3H$, $NH_2$, $CF_3$, or
straight or branched lower ($C_1$–$C_6$) alkyl or alkoxy or
an amino group substituted by one or more straight or branched lower ($C_1$–$C_6$) alkyl or alkyl carbonyl or alkoxy carbonyl group or
a COOH, COO alkyl, $CONH_2$, $CON(alkyl)_2$ group or
$R_1$-$R_2$ may together form —CH=CH—CH=CH—, —O—$(CH_2)_n$—O—,
with n=1 to 3;
$R_3$ is the same as $R_1$, or
$R_2$-$R_3$ can jointly form: —O—$(CH_2)_n$—O—, with n=1 to 3;
$R_4$, $R_5$: are each independently hydrogen or an alkyl, alkenyl, alkinyl, or
S—$R_8$, wherein $R_8$ is hydrogen or a straight or branched lower ($C_1$–$C_{10}$) alkyl group
SO—$R_8$, $SO_2R_8$
OH, or OH substituted for H with an O-protective group
O—CS—N—$R_8$
O—CO—N—$R_9$, wherein $R_9$ has the following meaning:

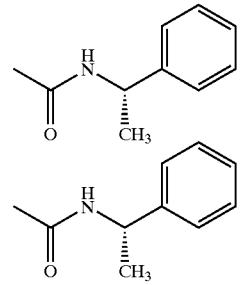

O—CO—$R_8$, or

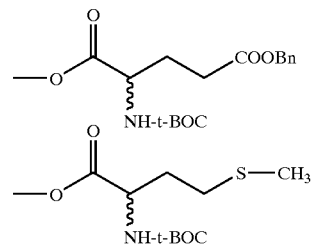

-continued

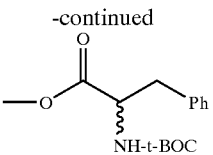

$R_4$, $R_5$ may jointly be $=N-NH-R_{10}$, $=N-NR_{10}R_{11}$, or $=N-O-R_{11}$, wherein $R_{10}$ is hydrogen, straight or branched lower ($C_1-C_6$) alkyl or alkyl carbonyl or alkyl carbonyloxy group or $-SO_3H$, and $R_{11}$ is hydrogen, straight or branched lower ($C_1-C_6$) alkyl or alkyl carbonyl group, or $-SO_3H$;

$R_4$ and $R_5$ may also be:

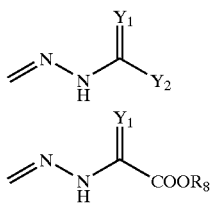

wherein $Y_1$ is O, S, NH or N—$R_{10}$ and $Y_2$ is —OH, —SH, —$NH_2$ or —$NHR_{10}$ $G_1$, $G_2$: jointly or separately have the meaning:
—C($R_{13}$, $R_{14}$)—, wherein $R_{13}$, $R_{14}$ can be hydrogen, OH, a straight or branched lower alkyl, aryl, alkoxy or aryloxy group or jointly as an alkyl spiro system ($C_3$ to $C_7$ spiro ring)

$G_1$ and $G_2$ may jointly represent

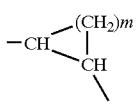

with m=1 to 7

$G_3$: represents $CH_2$ or =CO $R_6$ represents a group $—(G_4)_p—(G_5)_q—G_6$ with p, q=0–1, in which $G_4$ satisfies the following definition
—($CH_2$)$_r$—, —C($R_{15}R_{16}$)—($CR_2$)$_r$—, with r=1 to 6 and $R_{15}$, $R_{16}$=hydrogen, or straight or branched lower alkyl, cycloalkyl, or aryl groups
—O— or —$NR_{15}$

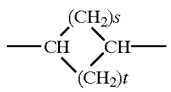

wherein s=1–4, and t=0–4

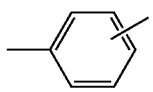

wherein $G_7=NR_{15}$, O or S, $G_5$ can be identical with or different from $G_4$ and, in the event that p=1, additionally represents —S—, $G_6$ fulfills the following definition:

wherein
$R_{17}$, $R_{18}$, $R_{19}$ and $R_{20}$ individually or jointly are the same or different, and are hydrogen, straight or branched lower alkyl, cycloalkyl or aryl groups, where $R_{17}$ and $R_{18}$ and $R_{19}$ and $R_{20}$ can jointly form a cycloalkyl group (with a ring size of 3–8)

$G_8$=O, S, NH, $NR_{21}$—($CH_2$)$_n$—, $R_{21}$=CHO, $COOR_{17}$ or a heteroaryl group selected from the group consisting of 2-pyridyl, 4-pyridyl, and 2-pyrimidinyl, which is unsubstituted or substituted identically or differently by one or several F, Cl, Br, I, $NO_2$, OH, alkyl, alkyloxy, CN, NC or $CF_3$, CHO, COOH, COO alkyl, $SO_3H$, SH or S-alkyl groups, or a methyl group, which is substituted by 1–3 phenyl groups, which are unsubstituted or substituted identically or differently by one or more F, Cl, Br, I, $NO_2$ alkyl, alkyloxy, CN, NC or $CF_3$ groups, wherein $G_8$ can also be:

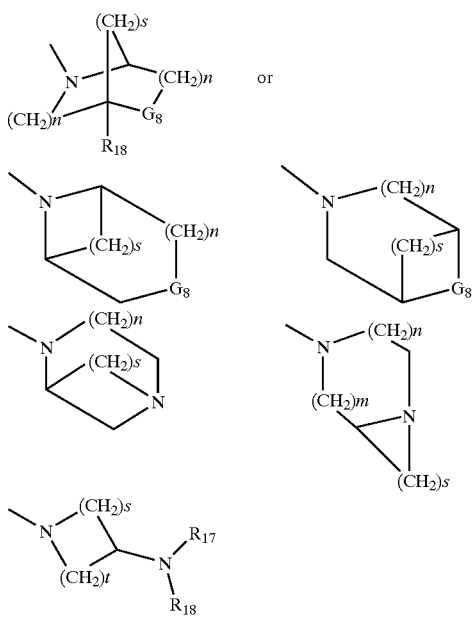

—CHO, $COOR_{17}$, —$CONR_{17}$ a straight or branched lower arylalkyl, arylalkenyl, arylalkinyl, cycloalkyl or aryl groups, —O—$R_{17}$, —$NR_{17}R_{18}$, phthalamid o, —CN or —NC;

$R_7$ is identical with $R_6$ or represents —O—$^{(-)}$ (N-oxide) or a free electron pair (e-pair), wherein $R_6$ and $R_7$ can also form a common ring, 3 to 8 carbon atoms in size and X exists only if, and represents an ion of a pharmacologically unstable inorganic or organic acid, where $R_6$ and $R_7$ are present and the nitrogen atom thus carries a positive charge; and Z=N or $N^+$ in the event that $R_6$ and $R_7$ are present jointly and $R_7$ is not $O^-$.

2. A composition consisting essentially of a compound according to claim 1, in admixture with a pharmaceutically acceptable excipient.

3. A method for treating Alzheimer's disease, comprising administering to a human patient in need thereof a pharmaceutically acceptable amount of a compound as claimed in claim 1.

* * * * *